(12) United States Patent
Lowy et al.

(10) Patent No.: US 7,220,419 B2
(45) Date of Patent: *May 22, 2007

(54) SELF-ASSEMBLING RECOMBINANT PAPILLOMAVIRUS CAPSID PROTEINS

(75) Inventors: Douglas R. Lowy, Washington, DC (US); John T. Schiller, Silver Spring, MD (US); Reinhard Kirnbauer, Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 650 days.

This patent is subject to a terminal disclaimer.

(21) Appl. No.: 10/371,846

(22) Filed: Feb. 21, 2003

(65) Prior Publication Data

US 2003/0219873 A1   Nov. 27, 2003

Related U.S. Application Data

(63) Continuation of application No. 09/832,065, filed on Apr. 9, 2001, now abandoned, which is a continuation of application No. 09/316,487, filed on May 21, 1999, now abandoned, which is a continuation of application No. 08/484,503, filed on Jun. 7, 1995, now Pat. No. 5,985,610, which is a continuation of application No. 08/032,869, filed on Mar. 16, 1993, now Pat. No. 5,437,951, which is a continuation-in-part of application No. 07/941,371, filed on Sep. 3, 1992.

(51) Int. Cl.
*A61K 39/12* (2006.01)

(52) U.S. Cl. .............. 424/204.1; 435/69.1; 435/69.3; 530/300

(58) Field of Classification Search ............... 435/69.1, 435/69.3, 235.1, 239, 471; 424/204.1; 530/350
See application file for complete search history.

(56) References Cited

U.S. PATENT DOCUMENTS

| | | | |
|---|---|---|---|
| 4,368,149 A | | 1/1983 | Masuho et al. |
| 4,520,113 A | | 5/1985 | Gallo et al. |
| 4,551,270 A | | 11/1985 | Danos et al. |
| 4,671,958 A | | 6/1987 | Rodwell et al. |
| 4,748,109 A | | 5/1988 | Baird |
| 4,777,239 A | | 10/1988 | Schoolnik et al. |
| 4,816,397 A | | 3/1989 | Boss et al. |
| 4,983,728 A | | 1/1991 | Herzog et al. |
| 5,039,607 A | | 8/1991 | Skold et al. |
| 5,045,447 A | | 9/1991 | Minson |
| 5,057,411 A | | 10/1991 | Lancaster et al. |
| 5,071,757 A | | 12/1991 | Kreider et al. |
| 5,081,029 A | | 1/1992 | Zarling et al. |
| 5,180,806 A | | 1/1993 | Dillner et al. |
| 5,186,933 A | | 2/1993 | Estes |
| 5,437,951 A | * | 8/1995 | Lowy et al. ............... 435/69.1 |
| 5,618,536 A | * | 4/1997 | Lowy et al. ............. 424/192.1 |
| 5,709,996 A | | 1/1998 | Lowy et al. |
| 5,716,620 A | | 2/1998 | Lowy et al. |
| 5,744,142 A | | 4/1998 | Lowy et al. |
| 5,756,284 A | | 5/1998 | Lowy et al. |
| 5,855,891 A | * | 1/1999 | Lowy et al. ............. 424/192.1 |
| 5,871,998 A | * | 2/1999 | Lowy et al. ............. 435/235.1 |
| 5,874,089 A | | 2/1999 | Schlegel et al. |
| 5,888,516 A | | 3/1999 | Jansen et al. |
| 5,985,610 A | * | 11/1999 | Lowy et al. ............... 435/69.3 |
| 6,331,415 B1 | | 12/2001 | Cabilly et al. |
| 6,485,728 B2 | | 11/2002 | Schlegel et al. |

FOREIGN PATENT DOCUMENTS

| | | |
|---|---|---|
| EP | 0133123 | 7/1984 |
| EP | 0 133 123 | 2/1985 |
| EP | 0 256 321 | 2/1988 |
| EP | 0 343 783 | 11/1989 |
| EP | 0 390 252 | 10/1990 |
| EP | 0 451 550 | 10/1991 |
| WO | WO 90/10459 | 9/1990 |
| WO | WO 90/10867 | 9/1990 |
| WO | WO 9010459 | 9/1990 |
| WO | WO 91/04330 | 4/1991 |
| WO | WO 91/18118 | 11/1991 |

(Continued)

OTHER PUBLICATIONS

Andrews and Pereira. 1978. "Reovirus" in *Viruses of Vertebrates*, third edition. Bailliere Tyndall London p. 57-60.

(Continued)

*Primary Examiner*—Ali R. Salimi
(74) *Attorney, Agent, or Firm*—Knobbe, Martens, Olson & Bear, LLP

(57) ABSTRACT

Recombinant papillomavirus capsid proteins that are capable of self assembly into capsomer structures and viral capsids that comprise conformational antigenic epitopes are provided. The capsomer structures and viral capsids, consisting of the capsid proteins that are expression products of a bovine, monkey or human papillomavirus L1 conformational coding sequence proteins, can be prepared as vaccines to induce a high titer neutralizing antibody response in vertebrate animals. The self assembling capsid proteins can also be used as elements of diagnostic immunoassay procedures for papillomavirus infection.

18 Claims, 3 Drawing Sheets

FOREIGN PATENT DOCUMENTS

| WO | WO 91/18294 | 11/1991 |
| --- | --- | --- |
| WO | WO 9118118 | 11/1991 |
| WO | WO 93/02184 | 1/1993 |
| WO | WO 93/02184 | 2/1993 |
| WO | WO 9302184 | 2/1993 |
| WO | WO 94/00152 | 1/1994 |
| WO | WO 9400152 | 1/1994 |
| WO | WO 94/20137 | 9/1994 |
| WO | WO 9420137 | 9/1994 |
| WO | WO 99/01557 | 1/1999 |
| WO | WO 00/23955 | 4/2000 |
| WO | WO 03/001208 | 1/2003 |

OTHER PUBLICATIONS

Bachmann et al. (1997) Neutralizing Antiviral B Cell Responses, Annual Rev. Immunol., 15:235-270.
Baker (1987) Sequence Analysis of Papillomavirus Genomes, in *The Papovaviridae*, Plenum Press, New York, pp. 321-385.
Baker et al. (1991) Structures of Bovine and Human Papillomaviruses, Analysis by cryoelectron microscopy and three-dimensional image reconstruction, Biophys. J. 60:1445-1456.
Baisley et al. (2000) Progress in the Development of Human Papillomavirus Vaccine for HPV-11 and HPV-16/18 and Mapping of a Critical Neutralizing Epitope, 18th International Papillomavirus Conference 2000 (Abstract).
Beiss et al. (1991) Type-specific and cross-reactive epitopes in human papillomavirus type 16 capsid proteins, Virology 184:460-464.
Bernard et al. (1994) Evolution of Papillomaviruses. Curr. Top. Micro. and Immuno. 186:33-54.
Bertioli et al. (1991) Transgenic plants and insect cells expressing the coat protein of arabis mosaic virus produce empty virus-like particles, J. Gen. Virol. 72:1801-1809.
Bonnez et al. (1990) Neutralization of HPV-11 Infection by Specific Polyclonal Antiserum Directed Against HPV-11 Viral Particles, Abstract at the Papillomavirus Workshop, Heidelberg, Germany May 12-17, 1990.
Bonnez et al. (1990) Use of HPV-11 Viral Particles in an ELISA to Detect Antibodies (Ab) in Humans with or without *Condylomata acuminata* (CA), Abstract at the Papillomavirus Workshop, Heidelberg, Germany May 12-17, 1990.
Bonnez et al. (1990) The PstI-XhoII Restriction Fragment of the HPV-6b L1 ORF Lacks Immunliogical Specificity as Determined by Sera From HpvB *Condyloma acuminatum* Patients and Controls. Papillomaviruses p. 77-80.
Bonnez et al. (1991) Use of Human Papillomavirus Type 11 Virions in an ELISA to Detect Specific Antibodies in Humans with *Condylomata acuminata*, J. Gen. Virol. 72:1343-47.
Bonnez et al. (1992) Antibody Response to Human Papillomavirus (HPV) Type 11 in Children with Juvenile-Onset Recurrent Respiratory Papillomatosis (RRP), Virology 188:384-387.
Bonnez et al. (1992) Antibody-Mediated Neutralization of Human Papillomavirus Type 11 (HPV-11) Infection in the Nude Mouse: Detection of HPV-11 mRNAs, J. Infectious Diseases 165:376-80.
Bradley et al. (1980) Antigen-induced T cell proliferative responses, In Vitro Immune Responses, pp. 164-166.
Breitburd et al. (1981) Detection and Characterization of Viral Genomes and Search for Tumoral Antigens in Two Hamster Cell Lines Derived from Tumors Induced by Bovine Papillomavirus Type 1, Int. J. Cancer 27:693-702.
Breitburd (1987) Cell Culture Systems for the Study of Papillomaviruses, in Papillomaviruses and Human Disease 371-92 (Syrjänen et al., eds.).
Breitburd et al. (1995) Immunization with Viruslike Particles from Cottontail Rabbit Papillomavirus (CRPV) Can Protect against Experimental CRPV Infection, J. of Virol., 69:3959-3963.
Breitburd et al. (1997) The Rabbit Viral Skin Papillomas and Carcinomas: A Model for the Immunogenetics of HPV-Associated Carcinogenesis, Clinics in Dermatology, 15:237-247.
Broker (1987) Structure and Genetic Expression of Papillomaviruses, Obstet. Gynecol. Clin. North Am. 14:329-348.
Brown et al. (1991) Assembly of Empty Capsids by Using Baculovirus Recmbinants Expressing Human Parvovirus B19 Structural Proteins. J. Virol. 65: 2702-2706.
Brown et al. (2001) Neutralization of Human Papillomavirus Type 11 (HPV-11) by Serum from Women Vaccinated with Yeast-Derived HPV-11 L1 Virus-like Particles: Correlation with Competitive Radioimmunoassay Titer. J. Infect. Dis. 184:1183-86.
Brown et al (2001) 19th International Papillomavirus Conference, Brazil, Abstract O-51.
Browne et al. (1988) Analysis of the L1 Gene Product of Human Papillomavirus Type 16 by Expression in a Vaccinia Virus Recombinant. J. Gen. Virol. 69: 1263-1273.
Burnette et al. (1990) Induction of Bovine Papillomavirus E2 Gene Expression and Early Region Transcription by Cell Growth Arrest: Correlation with Viral DNA Amplification and Evidence for Differential Promoter Induction, J. Virol. 64:5529-5541.
Campo (1991) Vaccination against Papillomavirus, Cancer Cells 3(11):421-426.
Campo et al. (1993) Prophylactic and Therapeutic Vaccination Against a Mucosal Papillomavirus, J. Gen. Virol. 74:945-53.
Campo (1997) Vaccination against Papillomavirus in Cattle, Clinics in Dermatology 15:275-283.
Carter et al. (1991) Expression of Human Papillomavirus Proteins in Yeast *Saccharomyces cerevisiae*. Virology 182: 513-21.
Carter et al. (1993) HPV-1 Capsids Expressed in Vitro Detect Human Serum Antibodies Associated with Foot Warts. Virology 195: 456-62.
Carter et al. (1994) Use of HPV 1 Capsids Produced by Recombinant Vaccinia Viruses in an ELISA to Detect Serum Antibodies in People with Foot Warts. Virology 199: 284-291.
Carter et al. (1995) Use of Human Papillomavirus Type 8 Capsids to Detect Antibodies in People with Genital Warts. J. Infect. Dis. 172:11-18.
Carter et al. (1996) The Natural History of Human Papillomavirus Type 16 Capsid Antibodies among a Cohort of University Women, J. of Infect. Diseases, 174:927-936.
Carter et al. (1997) Humoral Immune Repsonse to Human Papillomavirus Infection. Clinics in Dermatology 15:249-259.
Cason, et al. (1989) Identification of Immunogenic Regions of the Major Coat Protein of Human Papillomavirus Type 16 that Contain Type-restricted Epitopes. J. Gen. Virol., 70:2973-2987.
Cason et al. (1992) Detection of Antibodies to a Linear Epitope on the Major Coat Protein (L1) of Human Papillomavirus Type-15 (HPV-16) in Sera from Patients with Cervical Intraepithelial Neoplasia and Children, Int'l J. Cancer 50:349-355.
Cason et al. (1994) Detection of protein aggregates, but not virus-like particles, when the major (L1) coat protein of a wild-type human papillomavirus type 16 (HPV-16) is expressed in insect cells. Biochem. Soc. Trans. 22(3):335S.
Chackerian et al. (1999) Induction of Autoantibodies to Mouse CCR5 with Recombinant Papillomavirus Particles. Proc. Nat'l Acad. Sci., USA 96: 2373-78.
Chan et al. (1992) Phylogenetic Analysis of 48 Papillomavirus Types and 28 Subtypes and Variants: a Showcase for the Molecular Evolution of DNA Viruses, J. of Virol., 66:5714-5725.
Chandrachud et al. (1995) Vaccination of Cattle with the N-terminus of L2 is Necessary and Sufficient for Preventing Infection by Bovine Papillomavirus-4, Virology, 211:204-208.
Charvat et al., (1994) Serum antibodies to papillomavirus-like particles type 6, 11 and 16 in patients with recurrent respiratory papillomatosis, Programme & Abstract Book, 13th Intl. Papillomavirus Conf., Amsterdam, p. 316.
Chen et al. (1982) The primary structure and genetic organization of the bovine papillomavirus type 1 genome, Nature 299:529-534.
Chen et al. (1997) Mutant Canine Oral Papillomavirus L1 Proteins Form Virus-Like Particles but Lack Conformational Epitopes. 16th International Papillomavirus Conference, Sep. 5-11, 1997, University of Siena (Italy), p. 484.
Chen et al. (1996) Mutant canine oral papillomavirus L1 capsid proteins which form virus-like particles but lack native conformational epitopes, J. of Gen. Virol., 79:2137-2146.

Chen et al. (2000) Structure of Small Virus-like Particles Assembled from the L1 Protein of Human Papillomavirus 16. Molecular Cell 5:557-567.

Cheng et al. (1994) Sero-reactivity of women to virus-like particles made with a Zaire strain of HPV16: comparison with virus-like particles made with a german strain of HPV16, Abstract presented at the NIH Summer Student Poster Day Session.

Cheng et al. (1995) Divergent Human Papillomavirus Type 16 Variants are Serologically Cross-Reactive, J. of Infect. Diseases, 172:1584-1587.

Christensen et al. (1990) Antibody-Mediated Neutralization in vivo of infectious Papillomaviruses, J. Virol. 64(7):3151-56.

Christensen et al. (1990) Monoclonal Antibody-Mediated Neutralization of Infectious Human Papillomavirus Type 11, J. Virol. 64:5678-5681.

Christensen et al. (1991) The open reading frame L2 of cottontail rabbit papillomavirus contains antibody-inducing neutralizing epitopes, Virology 181:572-579.

Christensen et al. (1994) Assembled baculovirus-expressed human papillomavirus type 11 L1 capsid protein virus-like particles are recognized by neutralizing monoclonal antibodies and induce high titres of neutralizing antibodies, J. of Gen. Virol. 75:2271-2276.

Christensen et al. (1994) Human Papillomavirus Types 6 and 11 Have Antigenically Distinct Strongly Immunogenic Conformationally Dependent Neutralizing Epitopes, Virol. 205:329-335.

Christensen et al. (1995) Induction of Neutralizing Antibodies to Papillomaviruses by Anti-Idiotypic Antibodies, Virol. 210:292-301.

Christensen et al. (1996) Surface Comformational and Linear Epitopes on HPV-16 and HPV-18 L1 Virus-like Particles and Defined by Monoclonal Antibodies, Virology 223: 174-184.

Christensen et al. (1996) Monoclonal Antibodies to HPV-6 L1 Virus-like Particles Identify Conformational and Linear Neutralizing Epitopes on HPV-11 in Addition to Type-Specific Epitopes on HPV-6, Virology 224:477-486.

Christensen et al. (2001) Hybrid Papillomavirus L1 Molecules Assemble into Virus-like Particles That Reconstitute Conformational Epitopes and Induce Nuetralizing Antibodies to Distinct HPV Types, Virology 291:324-334.

Cole and Danos. (1987) Nucleotide Sequence and Comparative Analysis of The Human Papillomavirus Type 18 Genome, J. Mol. Biol. 193: 559-608.

Committee on New and Emerging Models for Biomedical and Behavioral Research et al (1998) What is a Model? *Biomedical Models and Resources Current Needs and Future Opportunities*, Appendix C, pp. 1-13.

Cook et al. (1999) Purification of Virus-like Particles of Recombinant Human Papillomavirus Type 11 Major Capsid Protein L1 from *Saccharomyces cerevisiae*, Protein Expression & Purification 17:477-484.

Cowsert et al. (1987) Topographical and Conformational Epitopes of Bovine Papillomavirus Type 1 Defined by Monoclonal Antibodies, J. Nat'l. Cancer Institute, 79:1053-1057.

Crawford et al. (1963) A comparative study of polyoma and papilloma viruses, Virology 21:258-263.

Davies et al. (1990) Definition of murine T helper cell determinants in the major capsid protein of human papillomavirus type 16, J. Gen. Virol. 71:2691-2698.

Debuf (ed) 1994. *The Veterinary Formulary Handbook of Medicine Used in Veterinary Practice*, 2nd Edition, The Pharmaceutical Press, London, pp. 385-386.

de Gruijl et al. (1997) Immunoglobulin G Responses Against Human Papillomavirus Type 16 Virus-Like Particles in a Prospective Nonintervention Cohort Study of Women with Cervical Intraepithelial Neoplasia, J. Nat'l Cancer Institute, 89:630-637.

de Villiers (1989) Heterogeneity of the Human Papillomavirus Group, J. Virol. 63(11):4898-4903.

Development of second generation of HPV vaccines, report from The current status of development of prophylactic vaccines against human papillomavirus infection, presented at the World Health Organization Technical Meeting in Geneva, Switzerland (1999).

Dillner et al. (1990) Mapping of Linear Epitopes of Human Papillomavirus Type 16: The L1 and L2 Open Reading Frames, Int. J. Cancer 45:529-35.

Dillner et al. (1991) Antigenic and Immunogenic Epitopes Shared by Human Papillomavirus Type 16 and Bovine, Canine, and Avian Papillomaviruses. J. Virol. 65:6862.

Dillner (1992) Immunobiology of papillomavirus. Prospects for vaccination, Cancer J. 5:181-187.

Dillner et al. (1995) Antibodies against linear and conformational epitopes of human papillomavirus type 16 that independently associate with incident cervical cancer. Int. J. Cancer 60(3):377-382.

Donnelly et al. (1998) Protection against Papillomavirus with a Polynucleotide Vaccine, J. of Infectious Diseases 713:314-320.

Doorbar et al. (1986) Identification of the human papillomavirus virus-1a E4 gene products. EMBO J. 5(2):355-362.

Doorbar et al. (1987) Identification of Proteins Encoded by the L1 and L2 Open Reading Frames of Human Papillomavirus 1a, J. Virol. 61(9):2793-2799.

Durst et al. (1983) A papillomavirus DNA from a cervical carcinoma and its prevalence in cancer biopsy samples from different geographic regions, Proc. Nat'l Acad. Sci., USA 80:3812-15.

Dvoretzky et al. (1980) A Quantitative in Vitro Focus Assay for Bovine Papilloma Virus, Virol. 103:369-375.

Elsinger et al. (1976) Propagation of human wart virus in tissue culture, Nature 256:432-434.

Ellis et al. (1997) Antithrombotic and antifibrinolytic effects of antithrombin III replacement in liver cirrhosis, The Lancet 349:1069-1070.

Fairlie et al. (1998) Towards Protein Surface Mimetics, Curr. Med. Chem. 5:29-62.

Fang et al. (1999) Post Translational Modifications of Recombinant Human Papillomavirus Type 6b Major Capsid Protein, Virus Res. 60(2):113-121.

Fang et al. (2000) Differences in the Post-Translational Modifications of Human Papillomavirus Type 6b Major Capsid Protein Expressed from a Baculovirus System Compared with a Vaccinia Virus System, Biotechnol. Appl. Biochem. 32:27-33.

Fenner and White (1976) *Medical Virology Second Edition*, Academic Press, New York, NY pp. 359-374.

Fey et al. (1989) Demonstration of in vitro synthesis of human papilloma viral proteins from hand and foot warts, J. Invest. Dermatol. 92(6):817-824 (Abstract).

Fields et al. (1985) *Fields Virology* Third Edition pp. 475.

Fife et al. (2000) A Dose-Ranging Study of the Safety and Immunogenity Profiles of an HPV 11 L1 VLP Candidate vaccine in Young Health Women, Abstract 364.

Finch and Klug (1965) The Structure of Viruses of the Papillomapolyoma Type III. Structure of Rabbit Papilloma Virus, J. Mol. Biol., 13:1-12.

Forghani 1991 "Enzyme Immunoassay Systems" in *Laboratory Diagnosis of Viral Infections*, 2nd Edition, E.H. Lenette ed., Marcel Dekker NY, pp. 102-125.

French et al. (1990) Assembly of Double-Shelled, Viruslike Particles of Bluetongue Virus by the Simultaneous Expression of Four Structural Proteins. J. Virol. 64(12): 5694-5700.

French and Roy (1990) Synthesis of Bluetongue Viru (BTV) Corelike Particles by Recombinant Baculovirus Expressing the Two Major Structural Core Proteins of BTV, J. Virol. 66:1530-1536.

Frommhagen (1965) The Separation and Physiochemical Properties of the C and D Antigens of Coxsackievirus, J. Immunol., 95:818-22.

Galloway (1992) Serological assays for the detection of HPV antibodies, IARC Sci. Publ. 119:147-161.

Galloway (1994) Papillomavirus Capsids: a New Approach to Identify Serological Markers of HPV Infection, J. Nat'l Canc. Inst. 86:474-475.

Gardas and Lewartowska. (1988) Coating of proteins to polystyrene ELISA plates in the presence of detergents, J. Immunol. Methods 106: 251-255.

Ghadially, (1997) The Nuclear Matrix and Interchromatin and Perichromatin Granules and Intranuclear Viral Inclusions and Virus-like Particles in *Ultrastructural Pathology of the Cell and Matrix*, vol. 1:30-35 and 136-145 (4th ed.).

Gheysen et al. 1989. Assembly and Release of HIV-1 precursor Pr55$^{gag}$ Virus-like Particles from Recombinant Baculovirus-Infected Insect Cells. Cell 59:103-112.

Ghim et al. (1991) Comparison of Neutralization of BPV-1 Infection of C127 Cells And Bovine Fetal Skin Xenografts, Int. J. Cancer 49:285-289.

Ghim et al. (1992) HPV-1 L1 Protein Expressed in cos Cells Displays Conformational Epitopes Found on Intact Virions, Virology 190:548-552.

Ghim and Jenson (1993) Identification of Conformational Epitopes of the BPV-1 Capsid Recognized by Competitive Inhibition of Sera from Infected or Immunized Animals, Pathobiology 61:138-44.

Ghim et al. (1994) Papilloma extracts and recombinant L1 protein protect completely against mucosal papillomavirus infection: a canine model, Programme & Abstract Book, 13th Intl. Papillomavirus Conf., Amsterdam, p. 56.

Gigler et al. (1999) Generation of Neutralizing Human Monoclonal Antibodies against Parvovirus B19 Proteins, J. Virol. 73:1974-79.

Giri et al. (1986) Papillomavirus genomes: from sequence data to biological properties, Trends Genet. 2:227-232.

Gissmann et al. (1987) Human Papillomaviruses and Cervical Cancer. Cancer Cells 5:275-280.

Grubman et al. (1985) Capsid Intermediates Assembled in a Foot-and-Mouth disease Virus Genome RNA-Programmed Cell-Free Translation System and in Infected Cells, J. Virol. 56:120-126.

Hagansee et al. (1993) Self-assembly of human papillomavirus type 1 capsids by expression of the L1 protein alone or by coexpression of the L1 and L2 capsid proteins, J. Virol. 67(1):315-322.

Hagensee et al. (1994) Three-Dimensional Structure of Vaccinia Virus-Produced Human Papillomavirus Type I Capsids, J. Virol. 68:4503-4505.

Hagensee et al. (1995) Immunization of Mice with HPV Vaccinia virus Recombinants Generates Serum IgG, IgM, and Mucosal IgA Antibodies, Virology 206:174-182.

Hagensee et al. (2000) Detection of Cervical Antibodies to Human Papillomavirus Type 15 (HPV-16) Capsid Antigens in Relation to Detection of HPV-16 DNA and Cervical Lesions, J. Infect. Dis. 181:1234-1239.

Harrison (2001) Principles of Virus Structures, in *Fields Virology*, Forth Ed. pp. 53-54.

Harro et al. (2000) A Safety and Immunogenicity Trial of Human Papillomavirus Type 16 L1 Virus-like Particle Vaccine in Healthy Young Adult Human Volunteers, 18th International Papillomavirus Conference (Abstract).

Hartig (1991) Generation of recombinant baculovirus via liposome-mediated transfection, Biotechniques 11:310-312.

Hayat, M.A. (2000) Chapter 7 Negative Staining, in *Principles and Techniques of Electron Microscopy*, 4th Edition, pp. 387-399.

Heim et al. (1995) Serum IgG, IgM, and IgA Reactivity to Human Papillomavirus Types 11 and 6 Virus-like Particles in Different Gynecologic Patient Groups. J. Infect. Dis. 172(2):395-402.

Heino et al. (1995) Human papillomavirus type 16 capsids expose multiple type-restricted and type-comon antigenic epitopes, J. Gen. Virol. 76:1141-1153.

Hewat et al. (1992) Three-Dimensional Reconstruction of Baculovirus Expressed Bluetongue Virus Core-Like Particles by Cryo-Electron Microscopy, Virology 189:10-20.

Hilleman et al. (1993) The preparation and safety of hepatitis B vaccine, J. Infection 7(Supp. I):3-8.

Hines et al. (1994) Role of Conformational Epitopes Expressed by Human Papillomavirus Major Capsid Proteins in the Serologic Detection of Infection and Prophylactic Vaccination, Gyn. Onco. 55:13-20.

Hines et al. (1994) The Expressed L1 Proteins of HPV-1, HPV-8, and HPV-11 Display Type-Specific Epitopes with Native Conformation and Reactivity with Neutralizing and Nonneutralizing Antibodies, Pathobiology 62:165-171.

Hofmann et al. (1995) Sequence Determination of Human Papillomavirus Type 6a and Assembly of Virus-like Particles in *Saccaromyces cerevisiae*, Virol. 209:506-518.

Höpfl et al. (1991) Skin test for HPV type 16 proteins in cervical intraepithelial neoplasia, Lancet 337:373-374.

Howley (1991) Papillomavirinae and Their Replication, *Fundamental Virology* (2nd ed.) Raven Press, New York, Chapter 30, pp. 743-768.

Immunotherapeutic products with have $2.4 billion European market in 1995, (1992) Biotechnology News 12(8):2.

In this Issue: New Test for HPV16 (1994) J. Nat. Cancer Inst. 86(7):473.

Iwasaki et al. 1992. Detection Of Capsid Antigen Of Human Papillomavirus (HPV) in Benign Lesions Of Female Genital Tract Using Anti-HPV Monoclonal Antibody. J. of Pathology. 168:293-300.

Jansen et al. (1995) Vaccination with yeast-expressed cottontail rabbit papillomavirus (CRPV) virus-like particles protects rabbits from CRPV-induced papilloma formation, Vaccine 13:1509-14.

Jarret et al. (1990) Studies on vaccination against papillomaviruses: a comparison of purified virus, tumour extract and transformed cells in prophylactic vaccination, Veterinary Record 126:449-452.

Jarret et al. (1991) Studies on Vaccination against Papillomaviruses: Prophylactic and Therapeutic Vaccination with Recombinant Structural Proteins, Virology 184:33-42.

Jenison et al. (1990) Evidence of Prevalent Genital-Type Human Papillomavirus Infections in Adults and Children, J. Infect. Dis. 162:60-69.

Jenkins et al. (1990) An Antigen Chimera of Poliovirus Induces Antibodies against Human Papillomavirus Type 16, J. Virol. 64:1201-1208.

Jenson et al. (1980) Immunologic Relatedness of Papillomaviruses from Different Species, J. Natl. Cancer Inst. 64:495-500.

Jenson et al. (1991) Identification of linear epitopes of the BPV-1 L1 protein recognized by Sera of infected or immunized animals, Pathobiology 59:396-403.

Jin et al. (1989) Identification of L2 open reading frame gene products of bovine papillomavirus type 1 using monoclonal antibodies, J. Gen. Virol. 70:1133-1140.

Jin et al. (1990) Bovine Serological Response to a Recombinant BPV-1 Major Capsid Protein Vaccine, Intervirology 31:345-354.

Kadish (1994) Recombinant Virus-like Particles Retain Conformational Epitopes of Native Human Papillomavirus and May Be Useful for Vaccine Development Gynaecol. Oncol. 55(1):10-12.

Kajigaya et al. (1991) Self-assembled B19 parvovirus capsids, produced in a baculovirus system, are antigenically and immunogenically similar to native virions, PNAS USA 88:4646-4650.

Kang et. al. (1987) Secretion of Particles of Hepatitis B Surface Antigen From Insect Cells Using a Baculovirus Vector, J. Gen. Virol. 68:2607-2613.

Kienzler et al. (1983) Humoral and Cell-Mediated Immunity to Human Papillomavirus Type 1 (HPV-1) in Human Warts, Br. J. Dermatol. 108:665-672.

Kimbauer et al. (1992) BPV L1 Assembled into Capsid-Like Structures In Insect Cells Generates High Titer Neutralizing Antisera, 11th International Papillomavirus Workshop, Edinburgh Conference Centre, Heriot-Watt University, Sep. 5-11, 1992, p. 17 Abstract.

Kimbauer et al. (1992) Papillomavirus L1 major capsid protein self-assembles into virus-like particles that are highly immunogenic, Kimbauer et al., PNAS USA 89:12180-12184.

Kimbauer et al. (1993) Efficient Self-Assembly of Human Papillomavirus Type 16 L1 and L1-L2 into Virus-Like Particles, J. Virol. 67:6929-6936.

Kimbauer et al. (1993) Human Papillomavirus Type 16 Virus-like Particles: Elisa to detect high Risk HPV Infection and Potential for a Preventive Vaccine, Investigative Dermatology 101(3):393 Abstract 31.

Kimbauer et al. (1993) Papillomavirus L1 Major Capsid Protein: Self-assembly into Particles That Are Morphologically and Immunologically Similar to Native Virions: In: Vaccines '93, Ginsberg, H.S. et al., Editor, Cold Spring Harbor Laboratory Press, pp. 305-310.

Kimbauer et al. (1994) A vaccine of virus-like particles made in insect cells can inhibit papillomavirus infection of rabbits, Programme & Abstract Book, 13th Intl. Papillomavirus Conf., Amsterdam, p. 154.

Kimbauer et al. (1994) A Virus-Like Particle Enzyme-Linked Immunosorbent Assay Detects Serum Antibodies in a Majority of Women Infected With Human Papillomavirus Type 16, J. Nat'l Canc. Inst. 86:494-499.

Kimbauer et al. (1996) Virus-like Particles of Bovine Papillomavirus Type 4 in Prophylactic and Therapeutic Immunization, Virol., 219:37-44.

Kols and Sherris (2000) HPV Vaccines: Promise and Challenges, Alliance for Cervical Cancer Prevention, Seattle, Washington, pp. 1-40.

Kossovsky et al. (1991) Nanocrystalline Epstein-Barr Virus Decoys, J. Appl. Biomater. 2(4):251-259.

Koutsky, L.A. et al (2001) 19th International Papillomavirus Conference, Brazil, Abstract O-50.

Kreider et al. (1986) In Vivo Transformation of Human Skin with Human Papillomavirus Type 11 from *Condylomata acuminata*, J. Virol. 59:369-376.

Kremsdorf et al. (1983) Human Papillomaviruses Associated with *Epidermodysplasia verruciformis*, J. Virol. 48(2):340-351.

Lancaster et al. (1975) Persistence of Viral DNA in human cell cultures infected with human papillomavirus, Nature 256:434-436.

Lancaster and Olson (1982) Animal Papillomaviruses, Microbiol. Rev. 46:191-207.

Larsen et al. (1987) Proteins Present in Bovine Papillomavirus Particles, J. Virol. 61:3596-3601.

Le Bouvier et al. (1966) Antigenic Diversity of Mammalian Papillomaviruses, J. Gen. Microbiol. 45:497-501.

Le Cann et al. (1994) Self-assembly of human papillomavirus type 16 capsids by expression of the L1 protein in insect cells. FEMS Microbiol. Lett. 117(3):269-274.

Le Cann et al. (1995) Detection of Antibodies against Human Papillomavirus (HPV) Type 16 Virions by Enzyme-Linked Immunosorbent Assay Using Recombinant HPV 16 L1 Capsids Produced by Recombinant Baculovirus, J. Clin. Microbiol. 33(5):1380-1382.

Lehtinen et al. (1990) Demonstration of evolutionary differences between conserved antigenic epitopes in the minor nucleocapsid protein of human papillomavirus types, Biochemical and Biophysical Research Communications 172:1378-1383.

Li et al. (1987) Identification of the Human Papillomavirus Type 6b L1 Open Reading Frame Protein in Condylomas and Corresponding Antibodies in Human Sera, J. Virol. 61:2684-2690.

Li et al. (1997) Expression of the human papillomavirus type 11 L1 capsid protein in *Escherichia coli*: characterization of protein domains involved in DNA binding and capsid assembly. J. Virol. 71:2988-2995.

Liddington et al. (1991) Structure of simian virus 40 at 3.8-A resolution, Nature 354:278-284.

Lin et al. (1992) Effective Vaccination against Papilloma Development by Immunization with L1 or L2 Structural Protein of Cottontail Rabbit Papillomavirus, Virology, 187:612-619.

Lin et al. (1993) Cottontail rabbit papillomavirus L1 protein-based vaccines: protection is achieved only with a full-length, nondenatured product, J. Virol. 67(7):4154-4162.

Liu (1998) Mucosal Immunisation with Papillomavirus Virus-like Particles Elicits Systemic and Mucosal Immunity in Mice. Virology 252(1):39-45.

Liu et al. (2001) Efficiency of delivery of DNA to cells by Bovine Papillomavirus Type-1 L1/L2 pseudovirions. Appl. Microbiol. Biotechnol. 56(1-2):150-156.

Lonberg-Holm and Yin (1973) Antigenic Determinants of Infective and inactivated Human Rhinovirus Type 2, J. Virol. 12:114-123.

Lopez de Turiso et al. (1992) Recombinant Vaccine for Canine Parvovirus in Dogs, J. Virol. 66:2748-2753.

Lörincz (1989) Human Papillomavirus Testing, Diagnostical & Clinical Testing 27:28-37.

Loudon and Roy. (1991) Assembly of Five Bluetongue Virus Proteins Expressed by Recombinant Baculoviruses: Inclusion of the Largest protein VP1 in the Core and Virus-like Particles, Virol. 180:798-802.

Lowe et al. (1997) Human papillomavirus type 11 (HPV-11) neutralizing antibodies in the serum and genital mucosal secretions of african green monkeys immunized with HPV-11 virus-like particles expressed in yeast, J. Infectious Diseases 176:1141-1145.

Lowy et al. (1994) Genital human papillomavirus infection, PNAS, USA 91:2436-2440.

Lowy and Schiller (1998) Papillomaviruses and Cervical Cancer: Pathogenesis and Vaccine Development, J. National Cancer Institute Monographs 23:27-30.

Lowy and Howley (2001) Papillomaviruses, in *Fields Virology* 4th Edition, vol. 2, pp. 2231-2264.

Luckow (1991) Cloning and Expression of Heterologous Genes in Insect Cells with Baculovirus Vectors, in *Recombinant DNA Technology and Applications*, (A. Prokop. R.K. Bajpal and C. Ho, editors) McGraw Hill, New York, NY pp. 97-152.

Luckow and Summers (1988) Trends in the Development of Baculovirus Expression Vectors, Bio/Technology 6:47-55.

Ludmerer et al. (1996) Glutamate May Substitute For ASP1999 and ASP202 in the Assembly of HPV1 and HPV16 VLPS, 15th International Papillomavirus Workshop, Dec. 6-9, 1996 Abstract.

Ludmerer et al. (1996) Two Amino Acid Residues Confer Type Specificity to a Neutralizing, Conformationally Dependent Epitope on Human Papillomavirus Type 11, J. Virol. 70:4791-4794.

Ludmerer et al. (2000) HPV11 Mutant Virus-like Particles Elicit Immune Responses That Neutralize Virus and Delineate a Novel Neutralizing Domain, Virology 266: 237-245.

Madeley et al. (1972) Human Wart Virus. *Virus Morphology*, Williams and Wilkins Company, Baltimore, p. 128.

Mansur and Androphy. (1993) Cellular Transformation by Papillomavirus Oncoproteins, Biochim. Biphys. Acta. 1155:323-45.

Martinez et al. (1992) Production of porcine parvovirus empty capsids with high immunogenic activity, Vaccine 10(10):684-690.

Mayer et al. (1957) The Purification of Poliomyelitis Virus as Studied by Complement Fixation, J. Immunol. 78:435-55.

McAleer et al. (1984) Human hepatitis B vaccine from recombinant yeast, Nature 307:178:180.

McCabe et al. (1988) The effects of detergent on the enzyme-linked immunosorbent assay (ELISA) of blood group substances, J. Immunol. Methods 108:129-135.

McCarthy et al. (1998) Quantitative Disassembly and Reassembly of Human Papillomavirus Type 11 Viruslike Particles in Vitro, J. Virol. 72:32-41.

McLean et al. (1990) Production and characterisation of a monoclonal antibody to human papillomavirus type 16 using recombinant vaccinia virus. J. Clin. Pathol. 43:488-492.

McNeil (1997) News: HPV vaccines for cervical cancer move toward clinic, encounter social issues, J. Nat'l Canc. Inst. 89:1664-1666.

Meissner (1999) Nucleotide sequences and further characterization of human papillomavirus DNA present in the CaSki, SiHa and HeLa cervical carcinoma cell lines, J. of Gen. Virol. 80:1725-1733.

Melnick. 1972. "Preliminary observation of the tissue culture of the serum hepatitis virus" in *Hepatitis and Blood Transfusion*, Proceedings of a symposium held at the University of California, San Francisco, Mar. 25-26. p. 391-392.

Miller et al. (1988) An Insect Baculovirus Host Vector for High Level Expression of Foreign Genes, in *Genetic Engineering* (J. K. Settow and A Hollander editors) Plenum Press pp. 277-296.

Miller (1988) Baculoviruses as Gene Expression Vectors, Annu. Rev. Microbial. 42:177-199.

Miyanohara et al. (1983) Expression of hepatitis B surface antigen gene in yeast, PNAS 80:1-5.

Morikawa et al. 1991. Analysis of the Requirements for the Synthesis of Virus-like Particles by Feline Immunodeficiency Virus *gag* Using Baculovirus Vectors. Virology 183:288-297.

Montross et al. (1991) Nuclear assembly of polyomavirus capsids in insect cells expressing the major capsid protein VP1, J. Virol. 4991-4998.

Muller et al. (1995) Papillomavirus Capsid Binding and Uptake by Cells from Different Tissues and Species, J. of Virol. 69:948-954.

Nardelli-Haefliger et al. (1997) Human Papillomavirus Type 16 Virus-Like Particles Expressed in Attenuated *Salmonella typhimurium* Elicit Mucosal and Systemic Neutralizing Antibodies in Mice, Infect. and Immun. 65:3326-3336.

Nakai et al. (1986) Monoclonal antibodies to genus- and type-specific papillomavirus structural antigens, Intervirol. 25:30-37.

Nayak et al. (1985) Biological and Immunological Properties of Haemagglutinin and Neuraminidase Expressed from Cloned cDNAs in Prokaryotic and Eukaryotic Cells, Vaccine 3(Suppl):165-71.

Neeper et al. (1996) Expression of the major capsid protein of human papillomavirus type 11 in *Saccharomyces cerevisae*, Gene 180:1-6.

Nicholls et al. (2000) The Immunology of Animal Papillomaviruses, Veterinary Immunology and Immunopathology 73:101-127.

Nonnenmacher et al. (1995) Serologic Response to Human Papillomavirus Type 16 (HPV-16) Virus-like Particles in HPV-16 DNA-Positive Invasive Cervical Cancer and Cervical Intraepithelial Neoplasia Grade III Patients and Controls from Colombia and Spain. J. Infect. Dis. 172(1):19-24.

Ochsenbein et al. (2000) Correlation of T Cell Independence of Antibody Responses with Antigen Dose Reaching Secondary Lymphoid Organs: Implications for Splenectomized Patients and Vaccine Design, J. Immun. 164:6296-6302.

Olson et al. (1960) Further observations on immunity to bovine cutaneous papillomatosis, Amer. J. Vet. Res. 21:233-242.

Olson (1963) Cutaneous papillomatosis in cattle and other animals, Ann. NY Acad. Sci. 108:1042-1056.

Olson et al. (1969) Oncogenicity of Bovine Papilloma Virus, Arch. Environ. Health 19:827-837.

Ostrow et al. (1991) A rhesus monkey model for sexual transmission of a papillomavirus isolated from a squamous cell carcinoma, PNAS, USA 87:8170-8174.

Ostrow et al. (1991) Characterization of the Complete RhPV1 Genomic Sequence and Integration Locus from a Metastatic Tumor, Virology 181:424-29.

Ozawa et al. (1987) Novel Transcription Map for the B19 (Human) Pathogenic Parvovirus, J. Virol. 61:2395-2406.

Paintsil et al. (1996) Carboxyl Terminus of Bovine Papillomavirus Type-1 L1 Protein Is Not Required for Capsid Formation, Virol. 223:238-244.

Parton (1990) Nucleotide Sequence of the HPV16L1 Open Reading Frame, Nucl. Acids Res. 18(12):3631.

Pass et al. (1973) Wart-Associated Antigens. II. Human Immunity to Viral Structural Proteins. J. Investigative Dermatology 60:307-311.

Perbal et al. 1983. Molecular Biology of Polyomaviruses and Herpesviruses. p. 3-48.

Pfister et al. (1979) Seroepidemiologic Studies of Bovine Papillomavirus Infections, J. Natl. Cancer Inst. 82:1423-1425.

Pfister (1984) Biology and Biochemistry in Papillomaviruses, Rev. Physiol. Biochem. Pharmacol. 99:111-181 (1984).

Pfister and Fuchs (1987) Papillomaviruses: Particles, Genome Organisation and Proteins, In *Papillomaviruses and Human Disease* (Syrjänen et al. eds.) Springer Verlag p. 2-18.

Pfister et al. (1994) Anatomy, Taxonomy and Evolution of Papillomaviruses, Intervirol. 37:143-149.

Pilacinski et al. (1984) Cloning and Expression in *Escherichia coli* of the Bovine Papillomavirus L1 and L2 Open Reading Frames, Bio/Technology pp. 356-380.

Pilacinski et al. (1988) Immunization against bovine papillomavirus infection, CIBA Found. Symp. 120:136-156.

Poland et al. (2000) A Randomized, Double-Blind, Placebo-Controlled Trial of the Immunogenicity and Reactogenicity of a Novel HPV 16 Vaccine: Preliminary Results, Abstract 363.

Ponten et al. (1995) Strategies for Global Control of Cervical Cancer, Int'l J. Cancer 60:1-26.

Pringle, C.R. (1993) Virus Taxonomy Update, Arch. Virol. 133:491-495.

Pushko et al. (1994) Sequence variation in the capsid protein genes of human papillomavirus type 16. J. Gen. Virol. 75:911-916.

Reid & Lörincz (1996) New Generation of Human Papillomavirus Tests, in Cervical Cancer & Preinvasive Neoplasia pp. 27-47 (Rubin and Hoskins eds., Philadelphia).

Rieger et al. (1991) Glossary of Genetics Classical and Molecular, Fifth Edition, Springer-Verlag, Berlin Heidelberg.

Robinson. 1990. *Principles and Practice of Infectious Diseases. Third ed*, Mandell, Douglas and Bennett (eds) Churchill Livingston Inc. Chapter 125: Hepatits B virus and Hepatitis Delta Virus. pp. 1204-1231.

Roden et al. (1994) Interaction of Papillomaviruses with the Cell Surface, J. Virol. 68:7260-7266.

Roden et al. (1994) Neutralization of Bovine Papillomavirus by Antibodies to L1 and L2 Capsid Proteins, J. Virol. 68:7570-7574.

Roden et al. (1995) Papillomavirus L1 Capsids Agglutinate Mouse Erythrocytes through a Proteinaceous Receptor, J. Virol. 69:5147-5151.

Roden et al. (1996) Assessment of the Serological Relatedness of Genital Human Papillomaviruses by Hemagglutination Inhibition, J. Virol. 70:3298-3301.

Roden et al. (1996) In Vitro Generation and Type-Specific Neutralization of a Human Papillomavirus Type 16 Virion Pseudotype, J. Virol. 70:5875-5883.

Roden et al. (1997) Characterization of a Human Papillomavirus Type 16 Variant-Dependent Neutralizing Epitope, J. Virol. 71:6247-6252.

Rombaut and Jore. (1997) Immunogenic, Non-Infectious Polio Subviral Particles Synthesized in *Saccharomyces cerevisiae*, J. Gen. Virol. 78(8):1829-1832.

Rose et al. (1990) Expression of the full-length products of the human papillomavirus type 6b (HPV-6b) and HPV-11 L2 open reading frames by recombinant baculovirus, and antigenic comparisons with HPV-11 whole virus particles, J. Gen. Virology 71:2725-2729.

Rose et al. (1993) Expression of Human Papillomavirus Type 11 L1 Protein In Insect Cells: In Vivo and In Vitro Assembly of Viruslike Particles, J. Virol. 67(4):1936-1944.

Rose et al. (1994) Serological differentiation of human papillomavirus types 11, 16 and 18 using recombinant virus-like particles, J. Gen. Virol. 75:2445-2449.

Rose et al. (1994) Human papillomavirus (HPV) type 11 recombinant virus-like particles induce the formation of neutralizing antibodies and detect HPV-specific antibodies in human sera, J. Gen. Virol. 75:2075-2079.

Rose et al. (1994) Seroresponses of Patients with HPV-6, -16, -18, or -31 infections to Recombinant HPV-11,-16, and -18 Virus Like Particles (VLPs), 13th Intl. Papillomavirus Conf., Amsterdam p. 327.

Rose et al. (1994) Antigenic cross reactivity between HPV6 and HPV11, 13th Intl. Papillomavirus Conf., Amsterdam p. 328.

Rose et al. (1998) Human Papillomavirus Type 11 Recombinant L1 Capsomeres Induce Virus-Neutralizing Antibodies, J. Virol. 72:6151-6154.

Roseto et al. (1984) Monoclonal Antibodies to the Major Capsid Protein of Human Papillomavirus Type 1, J. Gen. Virol. 65:1319-1324.

Rowlands et al. (1975) A Comparative Chemical and Serological Study of the Full and Empty Particles of Foot-and-Mouth Disease Virus, J. Gen. Virol. 26:277-238.

Rowlands (1992) How can peptide vaccines work? FEMS Microbiol. Lett. 100:479-482.

Roy et al. (1990) Recombinant Virus Vaccine for Bluetongue Disease in Sheep, J. Virol. 64:1998-2003.

Sabara et al. (1991) Assembly of Double-Shelled Rotaviruslike Particles by Simultaneous Expression of Recombinant VP6 and VP7 Proteins, J. Virol. 65:6994-6997.

Saiki et al. (1988) Primer-directed enzymatic amplification of DNA with a thermostable DNA polymerase, Science 239:487-491.

Salunke et al. 1986. Self-Assembly of Purified Polymavirus Capsid Protein $VP_1$. Cell 46: 895-904.

Sambrook et al. (1989) Expression of Cloned Genes in Cultured Mammalian Cells, Molecular Cloning: A Laboratory Manual, Cold Spring Harbor Laboratory, Ch. 16 pp. 1-72.

Sapp et al. (1994) Analysis of type-restricted and cross-reactive epitopes on virus-like particles of human papillomavirus type 33 and in infected tissues using monoclonal antibodies to the major capsid protein J. Gen Virol. 75:3375-3383.

Sapp et al. (1998) Papillomavirus Assembly Requires Trimerization of the Major Capsid Protein by Disulfides between Two Highly Conserved Cysteines, J. Virol. 72:6186-6189.

Sasagawa et al. (1994) Synthesis and assembly of virus-like particles of the human type papillomavirus 6 and 16 in fission yeast *Schizosaccharomyces pombe*, Programme & Abstract Book, 13th Intl. Papillomavirus Conf., Amsterdam, p. 154.

Sasagawa et al. (1995) Synthesis and Assembly of Virus-like Particles of Human Papillomavirus Type 6 and Type 16 in Fission Yeast *Schizosaccaromyces pombe*, Virol. 206:126-135.

Schiffman et al. (1992) Recent progress in defining the epidemiology of human papillomavirus infection and cervical neoplasma, Nat'l Cancer Inst. 84:394-398.

Schiller and Roden (1995) Papillomavirus-Like Particles, Review Article Papillomavirus Report 6(5):121-128.

Schiller (1999) Papillomavirus-like particle vaccines for cervical cancer, Molecular Medicine Today 5:209-215.

Schneider et al. (1991) Rhesus Papillomavirus Type 1 Cooperates with Activated *ras* in Transforming Primary Epithelial Rat Cells Independent of Dexamethasone, J. Virol. 65:3354-3358.

Schubert et al. (1985) Expression of a cDNA encoding a functional 241-kilodalton vesicular stomatitis virus RNA polymerase, PNAS, USA 82:7984-7988.

Seedorf et al. (1985) Human Papillomavirus Type 16 DNA Sequence, Virology 145:181-185.

Shade et al. (1986) Nucleotide Sequence and Genome Organization of Human Parvovirus B19 isolated from the Serum of a Child During Aplastic Crisis, J. Virol. 58:921-936.

Shaw and Kamen. (1986) A conserved AU Sequence from the 3' Untranslated Region of GM-CSF mRNA Mediates Selective mRNA Degradation, Cell 46:659-687.

Shope (1936) Immunization of rabbits to infectious papillomatosis, J. Exp. Med. 65:219-238.

Stauffer et al. (1998) Infectious Human Papillomavirus Type 18 Pseudovirions, J. Mol. Biol. 283:529-536.

Steele and Gallimore (1990) Humoral Assays of Human Sera to Disrupted and Nondisrupted Epitopes of Human Papillomavirus Type 1, Virology 174:388-398.

Steele et al. (2002) Detection of $CD4^+$ and $CD8^+$-T-Cell Responses to Human Papillomavirus Type 1 Antigens Expressed at Various Stages of the Virus Life Cycle by Using an Enzyme-Linked Immunospot Assay of Gamma Interferon Release, J. Virol. 76(12):6027-6036.

Steinberg and DiLorenzo. (1996) A possible role for human papillomaviruses in head and neck cancer, Cancer and Metastasis Reviews 15:91-112.

Sterling et al. (1990) Production of Human Papillomavirus Type 16 Virions in a Keratinocyte Cell Line, J. Virol. 64:6305-6307.

Sterling et al. (1993) Immunoelectron Microscopical Localization of Human Papillomavirus Type 16 L1 and E4 Proteins in Cervical Kertinocytes Cultured In Vivo, J. Invest. Dermatol. 100:154-158.

Stevens et al. (1987) Yeast-recombinant hepatitis B vaccine, JAMA 257:2612-2616.

Steven et al. (1997) The Making and Breaking of Symmetry in Virus Capsid Assembly: Glimpses of Capsid Biology from Cryoelectron Microscopy, FASEB J. 11(10):733-742.

Stites et al. (1980) Clinical laboratory methods of detecting cellular immune function, Basic and Clinical Immunol. 3:382-397.

Stoler et al. (1990) Infectious Cycle of Human Papillomavirus Type 11 in Human Foreskin Xenografts in Nude Mice, J. Virol. 64:3310-3318.

Strike et al. (1989) Expression in *Escherichia coli* of Seven DNA Fragments Comprising the Complete L1 and L2 Open Reading Frames of Human Papillomavirus Type 6b and the Localization of the 'Common Antigen' Region, J. Gen. Virol. 70:543-555.

Summers and Smith (1987) A Manual of Methods for Baculovirus Vectors and Insect Cell Culture Procedures, Texas Agricultural Experiment Station Bulletin 1555:5-56.

Sundberg (1987) Papillomavirus Infections in Animals, *in Papillomaviruses and Human Disease* (Syrjänen et al. eds.) Springer Verlag pp. 40-103.

Suzich et al. (1995) Systemic Immunization with papillomavirus L1 protein completely prevents the development of viral mucosal papillomas, PNAS, USA 92:11553-11557.

Syrjanen et al. (1987) Papillomavirus Infection and Cancer in *Papillomaviruses and Human Disease*, Springer Verlag p. 468-491.

Taichman et al. 1984. The Search for a Culture System for Papillomavirus. The Journal of Investigative Dermatology, vol. 83, No. 1 Supplement, pp. 2s-6s.

Touze et al. (1996) Production of human papillomavirus type 45 virus-like particles in insect cells using a recombinant baculovirus, FEMS Microbiology Letters 141:111-116.

Touze et al. (1998) In vitro gene transfer using human papillomavirus-like particles, Nucleic Acids Res. 26:1317-1323.

Touze et al. (1998) The L1 Major Capsid Protein of Human Papillomavirus Type 16 Variants Affects Yield of Virus-Like Particles Produced in an Insect Cell Expression System, J. Clin. Microbiol. 36:2048-2051.

Urukawa et al. (1989) Synthesis of Immunogenic, but Non-Infectious, Poliovirus Particles in Insect Cells by a Baculovirus Expression Vector, J. Gen. Virol. 70:1453-1463.

Van Regenmortel (1992) The conformational specificity of viral epitopes, FEMS Microbiol. Lett. 100:483-488.

Voller et al. (1976) Enzyme Immunoassays in diagnostic medicine, Bull. World Health Org. 53:55-65.

Volpers et al. (1994) Assembly of the Major and Minor Capsid Protein of Human Papillomavirus Type 33 into Virus-like Particles and Tubular Structures in Insect Cells, Virol. 200:504-512.

Volpers et al. (1995) Binding and Internationalization of Human Papillomavirus Type 33 Virus-Like Particles by Eukaryotic Cells. J. Virol. 69(6):3258-3264.

Wang et al. (1991) Baculovirus vectors for multiple gene expression and for occluded virus production, Gene 100:131-137.

Wang et al. (1997) A monoclonal antibody against intact human papillomavirus type 16 capsids blocks the serological reactivity of most human sera, J. Gen. Virol. 78: 2209-2215.

Watson et al. (1983) Eds, recombinant DNA—a short course, W.J. Freeman and Company (New York) publishers, p. 236.

White et al. (1998) In Vitro Infection and Type-Restricted Antibody-Mediated Neutralization of Authentic Human Papillomavirus Type 16, J. Virol. 72:959-984.

White et al. (1999) Characterization of a Major Neutralizing Epitope on Human Papillomavirus Type 16 L1, J. Virol. 73(6):4882-4889.

Wideroff et al. (1995) Evaluation of Seroreactivity to Human Papillomavirus Type 16 Virus-like Particles in an Incident Case-Control Study of Cervical Neoplasia, J. Infect. Dis. 172:1425-30.

Wikstrom et al. (1995) Identification of human papillomavirus seroconversions. J. Gen. Virol. 76:529-539.

Williamson and Dennis. (1991) The use of polymerase chain reaction for the detection of human papillomavirus type 13, J. Virol. Methods 31:57-66.

Xi and Banks. (1991) Baculovirus expression of the human papillomavirus type 16 capsid proteins: detection of L1-L2 protein complexes, J. Gen. Virol. 72:2981-2988.

Yamada et al. (1995) Human Papillomavirus Type 16 Variant Lineages in United States Populations Characterized by Nucleotide Sequence Analysis of the E6, L2, and l1 Coding Segments, J. Virol. 69:7743-7753.

Yaegashi et al. (1991) Characterization of murine polyclonal antisera and monoclonal antibodies generated against intact and denatured human papillomavirus type l virions. Journal of Virology 65:1578-1583.

Yeager et al. (2000) Neutralization of Human Papillomavirus (HPV) Psuedovirions: A Novel and Efficient Approach to Detect and Characterize HPV Neutralizing Antibodies, Virol. 278:570-577.

Yong Kang et al. (1987) Secretion of particles of hepatitis B surface antigen from insect cells using a baculovirus vector. Journal of General Virology 68:2607-2613.

Yuan et al. (2000) Bacterially-Expressed GST-L1 Fusion Protein: Simplified Purification, Maintenance of Native Conformation, and Efficacy as a Prophylactic Papillomavirus Vaccine, 18th Int'l. Papillomavirus Conference, Barcelona, Spain, Jul. 2000 (Abstract).

Yuan, et al. (2001) Immunization with a Pentameric L1 Fusion Protein Products against Papillomavirus Infection, J. Virol. 75(17):7848-7853.

Zhang et al. (1998) Expression of Human Papillomavirus Type 16 L1 Protein in *Escherichia coli*: Denaturation, Renaturation, and Self-Assembly of Virus-like Particles in Vitro, Virology 242:423-431.

Zhou et al. (1990) Increased antibody responses to human papillomavirus type 16 L1 protein expressed by recombinant vaccinia virus lacking serine protease inhibitor genes, J. Gen. Virol. 71:2185-2190.

Zhou et al. (1991) Expression of Vaccinia Recombinant HPV 16 L1 and L2 ORF Proteins in Epithelial Cells is Sufficient for Assembly of HPV Virion-like Particles, Virology 185:251-257.

Zhou et al. (1991) Human Papillomavirus Type 16 Virions Produced By A Recombinant Vaccinia Virus, 1991 Papillomavirus Workshop, Seattle, Jul. 20-26, 1991 (Abstract with excerpts of the Abstract Book from the 1991 PV Workshop Includes Program schedule, Author Index).

Zhou et al. (1991) Identification of the nuclear localization signal of human papillomavirus type 16 L1 protein, Virology 185:626-632.

Zhou et al. (1991) The induction of cytotoxic T-Lymphocyte precursor cells by recombinant vaccinia virus expressing human papillomavirus type 16 L1, Virology 181:203-210.

Zhou et al. (1992) Definition of Linear Antigenic Regions of HPV 16 L1 Capsid Protein Using Synthetic Virion-Like Particles, Virol. 189:592-599 (1992).

Zhou et al. (1993) Synthesis and assembly of infectious bovine papillomavirus particles In Vitro. Journal of General Virology 74:763-768.

Zur Hausen (1991) Viruses in human cancers. Science 254:1167-1173.

Bonnez et al. (1998) "Isolation and Propagation of Human Papillomavirus Typoe 16 in Human Xenografts Implanted in the Severe Combined Immunodeficiency Mouse," Journal of Virology, 72:5256-5261.

Gravitt et al. (2000) "Improved Amplification of Genital Human Papillomaviruses," Journal of Clinical Microbiology, 38:357-361.

Karasuyama and Melchers (1988) "Establishment of mouse cell lines which constitutively secrete large quantities of interleukin 2, 3, 4 or 5, using modified cDNA expression vectors," Eur. J Immunol, 18:97-104.

Man et al. (1989) "Treatment of human muscle creatine kinase with glutaraldehyde preferentially increases the immunogenicity of the native conformation and permits production of high-affinity monoclonal antibodies with recognize two distinct surface epitopes," Journal of Immunological Methods, 125:251-259.

Tizard (1982) *An Introduction to Veterinary Immunology*, Chapter 12—Immunoprophylaxis: General Principles of Vaccination and Vaccines, Second Edition, Published by W.B. Saunders Company, Philadelphia. pp. 178-192.

Alberts et al. eds. (1989) *Molecular Biology of the Cell*, 2nd ed. Garland Publishing, New York. Chapter 3 p. 87-134.

Alberts et al. eds. (1989) *Molecular Biology of the Cell*, 2nd ed. Garland Publishing, New York. p. 265.

Alberts et al. eds. (1989) *Molecular Biology of the Cell*, 2nd ed. Garland Publishing, New York. p. 269-70.

Alberts et al. eds. (1989) *Molecular Biology of the Cell*, 2nd ed. Garland Publishing, New York. Chapter 18 p. 1001-1057.

AF Geijersstam et al. (1999) "A Survey of Seroprevalence of Human Papillomavirus Types 16, 18 and 33 among Children", *Int. J. Cancer* 80: 489-493.

Anderson-Ellstrom et al. (1996) "Comparison of Development of Serum Antibodies to HPV16 and HPV33 and Acquistion of Cervial HPV DNA Among Sexually Experienced and Virginal Young Girls". *Sex. Transm. Dis.* 23: 234-238.

Andrews et al. (1978) "Reovirus" in *Viruses of Vertebrates*, third edition. Bailliere Tyndall London p. 57-60.

Antinore et al. (1991) "HPV-16 E7 is Cytotoxic when Expressed from the CMV Promoter in the SCC 12 F.2 Line". Abstract. *Papillomavirus Workshop*. Jul. 20 to Jul. 26. Seattle, Washington.

ASV Scientific Program, (1990) The American Society for Virology 1990 Annual Meeting, Jul. 8-12, 1990.

Bachmann et al. (1997) "Neutralizing Antiviral B Cell Responses", *Annual Rev. Immunol.*, 15:235-270.

Baker (1987) "Sequence Analysis of Papillomavirus Genomes", in *The Papovaviridae*, Plenum Press, New York, pp. 321-385.

Baker et al. (1991) "Structures of Bovine and Human Papillomaviruses, Analysis by cryoelectron microscopy and three-dimensional image reconstruction", *Biophys. J.* 60:1445-1456.

Balsley et al. (2000) "Progress in the Development of Human Papillomavirus Vaccines for HPV-11 and HPV-16/18 and Mapping of a Critical Neutralizing Epitope", $18^{th}$ *International Papillomavirus Confernece* 2000 (Abstract).

Band et al. (1990) "Human Papilloma Virus DNAs Immortalize Normal Human Mammary Epithelial Cells and Reduce their Growth Factor Requirements", *PNAS USA* 87: 463-467.

Becker et al. (2004) "Nuclear localization but Not PML Protein Is Required for Incorporation of the Papillomavirus Minor Capsid Protein L2 into Virus-like Particles", *J. of Virol.* 78: 1121-1128.

Beiss et al. (1991) "Type-Specific and Cross-Reactive Epitopes in Human Papillomavirus Type 16 Capsid Proteins", *Virology* 184:460-464.

Belnap et al. (1996) "Conserved Feature in Papillomavirus and Polyomavirus Capsids", *J. Molecular Biology* 259: 249-263.

Bernard et al. (1994) "Evolution of Papillomaviruses", *Curr. Top. Micro. and Immuno.* 186:33-54.

Bertioli et al. (1991) "Transgenic Plants and Insect Cells Expressing the Coat Protein of Arabis Mosaic Virus Produce Empty Virus-Like Particles", *J. Gen. Virol.* 72:1801-1809.

Bierly et al. (1992) "Morphometric Estimation of Viral Burden in Cell Culture Material by Transformation Electron Microscopy (TEM)", *Proc. of 50th Annual Meeting of Electron Microscopy Society of America.* p. 732-733.

Big Dye Terminator v3.1 Cycle Sequencing Kit Produced by Applied Biosystems (2002) Chapter 3 and table of contents.

Bjørge et al. (1997) "A Prospective, Seroepidemiological Study of the Role of Human Papillomavirus in Esophageal Cancer in Norway", *Cancer Res.* 57: 3989-3992.

Bjørge et al. (1997) "Prospective Seroepdiemiological Study of Role of Human Papillomavirus in Non-Cervical Anogenital Cancers.", *BMJ* 315: 646-649.

Bonnez et al. (1990) "Neutralization of HPV-11 Infection by Specific Polyclonal Antiserum Directed Against HPV-11 Viral Particles", Abstract at the *Papillomavirus Workshop*, Heidelberg, Germany May 12-17, 1990.

Bonnez et al. (1990) "Use of HPV-11 Viral Particles in an ELISA to Detect Antibodies (Ab) in Humans with or without *Condylomata acuminata* (CA)", Abstract at the *Papillomavirus Workshop*, Heidelberg, Germany May 12-17, 1990.

Bonnez et al. (1990) "The PstI-XhoII Restriction Fragment of the HPV-6b L1 ORF Lacks Immunilogical Specificity as Determined by Sera From HPv6 *Condyloma acuminatum* Patients and Controls," *Papillomaviruses* p. 77-80.

Bonnez et al. (1991) "Antibody (Ab) Response to HPV-11 in Children with Juvenile-Onset Recurrent Respiratory Papillomatosis (RRP)," Abstract. *1991 Papillomavirus Workshop*. Jul. 20 to Jul. 26. Seattle, Washington.

Bonnez et al. (1991) "Neutralization of HPV-11 Infection in the Nude Mouse Xenograft Model with an Antibody Directed to a 15-mer Peptide Derived from the 3' End of HPV-11 L1 ORF", *1991 Papillomavirus Workshop*. Jul. 20 to Jul. 26. Seattle, Washington.

Bonnez et al. (1991) "Use of Human Papillomavirus Type 11 Virions in an ELISA to Detect Specific Antibodies in Human with *Condylomata acuminata* ", *J. Gen. Virol.* 72:1343-47.

Bonnez et al. (1992) "Antibody Response to Human Papillomavirus (HPV) Type 11 in Children with Juvenile-Onset Recurrent Respiratory Papillomatosis (RRP)", *Virology* 188:384-387.

Bonnez et al. (1992) "Antibody-Mediated Neutralization of Human Papillomavirus Type 11 (HPV-11) Infection in the Nude Mouse: Detection of HPV-11 mRNAs", *J. Infectious Diseases* 165:376-80.

Bonnez et al. (1994) "Evaluation of Temperature Sensitivity of Human Papillomavirus Type 11 by Using the Human Xenograft Severe Combined Immunodeficiency Mouse Model", *J. Clin. Microbiol.* 32: 1575-1577.

Bradley et al. (1980) "Antigen-Induced T Cell Proliferative Responses", *In Vitro Immune Responses*, pp. 164-166.

Brandsma et al. (1986) "Presence of Human Papillomavirus Type 16 Related Sequences in Verrucous Carcinoma of the Larynx," *Cancer Research* 46:2185-2188.

Brandwein et al. (1989) "Human Papillomavirus 6/11 and 16/18 in Schneiderian Inverted Papillomas," *Cancer* 63:1708-1713.

Breitburd et al. (1981) "Detection and Characterization of Viral Genomes and Search for Tumoral Antigens in Two Hamsters Cell Lines Derived from Tumors Induced by Bovinve Papillomavirus Type 1", *Int. J. Cancer* 27:693-702.

Breitburd (1987) "Cell Culture Systems for the Study of Papillomaviruses", in *Papillomaviruses and Human Disease*, pp. 371-392 (Syrjänen et al., eds.).

Breitburd et al. (1995) "Immunization with Viruslike Particles from Cottontail Rabbit Papillomavirus (CRPV) Can Protect against Experimental CRPV Infection", *J. of Virol.*, 69:3959-3963.

Breitburd et al. (1997) "The Rabbit Viral Skin Papillomas and Carcinomas: A Model for the Immunogenetics of HPV-Associated Carcinogenesis", *Clinics in Dermatology*, 15:237-247.

Broker (1987) "Structure and Genetic Expression of Papillomaviruses", *Obstet. Gynecol. Clin. North Am.* 14:329-348.

Brown et al. (1991) "Assembly of Empty Capsids by Using Baculovirus Recombinants Expressing Human Parvovirus B19 Structural Proteins," *J. of Virol.* 65: 2702-2706.

Brown et al. (2001) "Neutralization of Human Papillomavirus Type 11 (HPV-11) by Serum from Women Vaccinated with Yeast-Derived HPV-11 L1 Virus-like Particles: Correlation with Competitive Radioimmunoassay Titer," *J. Infect. Dis.* 184:1183-1186.

Brown et al. (2001) *19th International Papillomavirus Conference*, Brazil, Abstract O-51.

Browne et al. (1988) "Analysis of the L1 Gene Product of Human Papillomavirus Type 16 by Expression in a Vaccinia Virus Recombinant," *J. Gen. Virol.* 69:1263-1273.

Bubb et al. (1988) "DNA Sequence of the HPV-16 E5 ORF and the Structural Conservation of its Encoded Protein," *Virology*, 163:243-246.

Buck et al. (2005) "Maturation of Papillomavirus Capsids," *J. of Virol.* 79:2839-2846.

Burnett et al. (1990) "Induction of Bovine Papillomavirus E2 Gene Expression and Early Region Transcription by Cell Growth Arrest: Correlation with Viral DNA Amplification and Evidence for Differential Promoter Induction", *J. of Virol.* 64:5529-5541.

Campo (1991) "Vaccination against Papillomavirus", *Cancer Cells* 3:421-426.

Campo et al. (1993) "Prophylactic and Therapeutic Vaccination Against a Mucosal Papillomavirus", *J. Gen. Virol.* 74:945-53.

Campo (1997) "Vaccination against Papillomavirus in Cattle", *Clinics in Dermatology* 15:275-283.

Cann (1997) Principles of Molecular Biology, 2nd ed. Academic Press. p. 278.

Capell et al. (2004) "A Vaccine every Woman Should Take", *Business Week Online*. http://www.businessweek.com/print/magazine/content/04_48/b3910080_mz054.htm.

Carter et al. (1991) "Expression of Human Papillomavirus Proteins in Yeast *Saccharomyces cerevisiae,*" *Virology* 182:513-521.

Carter et al. (1993) "HPV-1 Capsids Expressed in Vitro Detect Human Serum Antibodies Associated with Foot Warts," *Virology* 195:456-62.

Carter et al. (1994) "Use of HPV 1 Capsids Produced by Recombinant Vaccinia Viruses in an ELISA to Detect Serum Antibodies in People with Foot Warts," *Virology* 199:284-291.

Carter et al. (1995) "Use of Human Papillomavirus Type 6 Capsids to Detect Antibodies in People with Genital Warts," *J. Infect. Dis.* 172:11-18.

Carter et al. (1996) "The Natural History of Human Papillomavirus Type 16 Capsid Antibodies among a Cohort of University Women", *J. of Infect. Diseases* 174:927-936.

Carter et al. (1997) "Humoral Immune Response to Human Papillomavirus Infection", *Clinics in Dermatology* 15:249-259.

Casjens et al. (1997) "Principles of Virion Structure, Function and Assembly," *Structural Biology of Viruses*, Oxford University Press. p. 3.

Cason, et al. (1989) "Identification of Immunogenic Regions of the Major Coat Protein of Human Papillomavirus Type 16 that Contain Type-restricted Epitopes" *J. Gen. Virol.* 70:2973-2987.

Cason et al. (1991) "Topographical Mapping of Epitopes on the Exterior of Bovine Papillomavirus Type-2 and the Identification of a Neutralizing Epitope," Abstract. *1991 Papillomavirus Workshop.* Jul. 20 to Jul. 26. Seattle, Washington.

Cason et al. (1992) "Detection of Antibodies to a Linear Epitope on the Major Coat Protein (L1) of Human Papillomavirus Type-15 (HPV-16) in Sera from Patients with Cervical Intraepithelial Neoplasia and Children," *Int'l J. Cancer* 50:349-355.

Cason et al. (1994) "Detection of Protein Aggregates, but no Virus-Like Particles, when the Major (L1) Coat Protein of a Wild-Type Human Papillomavirus Type 16 (HPV-16) is Expressed in Insect Cells," *Biochem Soc. Trans.* 22:335S.

Chackerian et al. (1999) "Induction of Autoantibodies to Mouse CCR5 with Recombinant Papillomavirus Particles," *PNAS USA* 96: 2373-78.

Chan et al. (1992) "Phylogenetic Analysis of 48 Papillomavirus Types and 28 Subtypes and Variants: a Showcase for the Molecular Evolution of DNA Viruses", *J. of Virol.*, 66:5714-5725.

Chandrachud et al. (1995) "Vaccination of Cattle with the N-terminus of L2 Is Necessary and Sufficient for Preventing Infection by Bovine Papillomavirus-4", *Virology* 211:204-208.

Charvat et al. (1994) "Serum Antibodies to Papillomavirus-Like Particles Type 6, 11 and 16 in Patients with Recurrent Respiratory Papillomatosis", *Programme & Abstract Book, 13th Intl. Papillomavirus Conf.*, Amsterdam, p. 316.

Chen et al. (1982) "The Primary Structure and Genetic Organization of the Bovine Papillomavirus Type 1 Genome", *Nature* 299:529-534.

Chen et al. (1997) "Mutant Canine Oral Papillomavirus L1 Proteins Form Virus-Like Particles but Lack Conformational Epitopes," *16th International Papillomavirus Conference*, Sep. 5-11, 1997, University of Siena (Italy), p. 484.

Chen et al. (1998) "Mutant Canine Oral Papillomavirus L1 Capsid Proteins which Form Virus-Like Particles but Lack Native Conformational Epitopes", *J. of Gen. Virol.* 79:2137-2146.

Chen et al. (2000) "Structure of Small Virus-like Particles Assembled from the L1 Protein of Human Papillomavirus 16," *Molecular Cell* 5:557-567.

Cheng et al. (1994) "Sero-Reactivity of Women to Virus-Like Particles Made with a Zaire Strain of HPV16: Comparison with Virus-Like Particles Made with a German Strain of HPV16", *Abstract presented at the NIH Summer Poster Day Session.*

Cheng et al. (1995) "Divergent Human Papillomavirus Type 16 Variants are Serologically Cross-Reactive", *J. of Infect. Diseases* 172:1584-1587.

Choo et al. (1988) "Sequence Duplication and Internal Deletion in the Integrated Human Papillomavirus Type 16 Genome Cloned from a Cervical Carcinoma," *J. of Virol.* 62:1659-1666.

Chua et al. (1996) "A Prospective Study on the Risk of Cervical Intra-epithelial Neoplasia Among Healthy Subjects with Serum Antibodies to HPV Compared with HPV DNA in Cervical Smears," *Int. J. Cancer* 68:54-59.

Christensen et al. (1990) "Antibody-Mediated Neutralization In Vivo of Infectious Papillomaviruses", *J. of Virol.* 64:3151-56.

Christensen et al. (1990) "Monoclonal Antibody-Mediated Neutralization of Infectious Human Papillomavirus Type 11", *J. Virol.* 64:5678-5681.

Christensen et al. (1990) "Immunological Cross-Reactivity to Laboratory-Produced HPV-11 Virions of Polysera Raised against Bacterially Derived Fusion Proteins and Synthetic Peptides of HPV-6b and HPV-16 Capsid Proteins," *Virology* 175: 1-9.

Christensen et al. (1991) "The Open Reading Frame L2 of Cottontail Rabbit Papillomavirus Contains Antibody-Inducing Neutralizing Epitopes", *Virology* 181:572-579.

Christensen et al. (1994) "Assembled Baculovirus-Expressed Human Papillomavirus Type 11 L1 Capsid Protein Virus-Like Particles are Recognized by Neutralizing Monoclonal Antibodies and Induce High Titres of Neutralizing Antibodies", *J. of Gen. Virol.* 75:2271-2276.

Christensen et al. (1994) "Human Papillomavirus Types 6 and 11 Have Antigenically Distinct Strongly Immunogenic Conformationally Dependent Neutralizing Epitopes", *Virology* 205:329-335.

Christensen et al. (1995) "Induction of Neutralizing Antibodies to Papillomaviruses by Anti-Idiotypic Antibodies", *Virology* 210:292-301.

Christensen et al. (1996) "Surface Conformational and Linear Epitopes on HPV-16 and HPV-18 L1 Virus-like Particles and Defined by Monoclonal Antibodies", *Virology* 223: 174-184.

Christensen et al. (1996) "Monoclonal Antibodies to HPV-6 L1 Virus-like Particles Identify Conformational and Linear Neutralizing Epitopes on HPV-11 in Addition to Type-Specific Epitopes on HPV-6", *Virology* 224:477-486.

Christensen et al. (2001) "Hybrid Papillomavirus L1 Molecules Assemble into Virus-like Particles That Reconstitute Conformational Epitopes and Induce Neutralizing Antibodies to Distinct HPV Types", *Virology* 291:324-334.

Cole et al. (1987) "Nucleotide Sequence and Comparative Analysis of The Human Papillomavirus Type 18 Genome", *J. Mol. Biol.* 193:559-608.

Cole et al. (1992) "Commentary: Progress and Prospects for Human Cancer Vaccines," *J. Nat'l Cancer Inst*. 84:18-23.

Combita et al. (2002) "Identification of Two Cross-Neutralizing Linear Epitopes within the L1 Major Capsid Protein of Human Papillomaviruses," *J. Virol*. 76: 6480-6486.

Comerford et al. (1991) "T- and B-Cell Epitopes of the HPV16 E7 Protein," Abstract. *1991 Papillomavirus Workshop*. Jul. 20 to Jul. 26. Seattle, Washington.

Coen (1991) "Molecular Genetics of Animal Viruses", in *Fundamental Virology* 2nd ed. Raven Press, New York. Chap. 7. p. 123-150.

Cook et al. (1999) "Purification of Virus-like Particles of Recombinant Human Papillomavirus Type 11 Capsid Protein L1 from *Saccharomyces cerevisiae*", *Protein Expression & Purification* 17:477-484.

Cowsert et al. (1987) "Topographical and Conformational Epitopes of Bovine Papillomavirus Type 1 Defined by Monoclonal Antibodies", *J. Nat'l. Cancer Institute*, 79:1053-1057.

Crawford et al. (1963) "A Comparative Study of Polyoma and Papilloma Viruses", *Virology* 21:258-263.

Crum (2002) "The Beginning of the End for Cervical Cancer?" *N. Eng. J. Med*. 347:1703-1705.

Crum et al. (2002) "Human Papillomaviruses, Applications, Caveats and Prevention," *J. Reproductive Med*. 47: 519-529.

Danos et al. (1982) "Human Papillomavirus 1a Complete DNA Sequence: a Novel Type of Genome Organization Among Papovaviridae," *EMBO J*. 1:231-236.

Danos et al. (1983) "Comparative Analysis of the Human Type 1a and Bovine Type 1 Papillomavirus Genomes," *J. of Virol*. 46:557-566.

Darnell et al. (1986) "Molecular Cell Biology", *Scientific American Book, Inc*. p. 229-234.

Darnell et al. (1986) "Molecular Cell Biology", *Scientific American Book, Inc*. p. 138-143.

Darnell et al. (1986) "Molecular Cell Biology", *Scientific American Book, Inc*. p. 210.

Darnell et al. (1986) "Molecular Cell Biology", *Scientific American Book, Inc*. p. 78 and Figure.

Davies et al. (1990) "Definition of murine T Helper Cell Determinants in the Major Capsid Protein of Human Papillomavirus Type 16", *J. Gen. Virol*. 71:2691-2698.

Debuf (ed) (1994) *The Veterinary Formulary Handbook of Medicine Used in Veterinary Practice*, 2nd Edition, The Pharmaceutical Press, London, p. 385-386.

De Grujil et al. (1997) "Immunoglobulin G Responses Against Human Papillomavirus Type 16 Virus-Like Particles in a Prospective Nonintervention Cohort Study of Women with Cervical Intraepithelial Neoplasia", *J. Nat'l Cancer Institute* 89:630-637.

De Villiers (1989) "Heterogeneity of the Human Papillomavirus Group", *J. of Virol*. 63:4898-4903.

"Development of Second Generation of HPV Vaccines, Report from The Current Status of Development of Prophylactic Vaccines Against Human Papillomavirus Infection", presented at the *World Health Organization Technical Meeting in Geneva*, Switzerland (1999).

Dillner et al. (1990) "Mapping of Linear Epitopes of Human Papillomavirus Type 16: The L1 and L2 Open Reading Frames", *Int. J. Cancer* 45: 529-535.

Dillner et al. (1991) "Antigenic and Immunogenic Epitopes Shared by Human Papillomavirus Type 16 and Bovine, Canine, and Avian Papillomaviruses", *J. of Virol*. 65:6862.

Dillner (1992) "Immunobiology of Papillomavirus. Prospects for Vaccination", *Cancer J*. 5:181-187.

Dillner et al. (1995) "Antibodies against Linear and Conformational Epitopes of Human Papillomavirus Type 16 that Independently Associate with Incident Cervical Cancer," *Int. J. Cancer* 60:377-382.

Dillner et al. (1996) "Seropositivities to Human Papillomavirus Types 16, 18, or 33 Capsids and to *Chlamydia trachometis* are Markers of Sexual Behavior," *J. Infect. Dis*. 173:1394-1398.

Dillner et al. (1997) "Prospective Seroepidemiologic Study of Human Papillomavirus Infection as a Risk Factor for Invasive Cervical Cancer," *J. Nat'l Cancer Inst*. 89: 1293-1299.

Dillner et al. (1998) "Sero-Epidemiologal Associated between Human-Papillomavirus Infection and Risk of Prostate Cancer," *Int. J. Cancer* 75: 564-567.

Dollard et al. (1991) "Genetic Activity of Human Papillomavirus Type 11 in Raft Cultures," *1991 Papillomavirus Workshop*. Jul. 20 to Jul. 26. Seattle, Washington.

Donnelly et al. (1996) "Protection against Papillomavirus with a Polynucleotide Vaccine", *J. of Infectious Diseases* 713:314-320.

Doorbar et al. (1986) "Identification of the Human Papillomavirus-1a E4 Gene Products," *EMBO J*. 5:358-362.

Doorbar et al. (1987) "Identification of Proteins Encoded by the L1 and L2 Open Reading Frames of Human Papillomavirus 1a", *J. Virol*. 61:2793-2799.

Doorbar et al (1990) "Detection of Novel Splicing Patterns in a HPV16-Containing Keratinocyte Cell Line," *Virology* 178:254-262.

Dunn et al. (1968) "Intranuclear Virus Particles in Human Genital Wart Tissue: Observations on the Ultrastructure of the Epidermal Layer," *J. Ultrastructure Research* 22:282-295.

Durst et al. (1983) "A Papillomavirus DNA from a Cervical Carcinoma and its Prevalence in Cancer Biopsy Samples from Different Geographic Regions", *PNAS USA* 80:3812-3815.

Durst et al. (1987) "Papillomavirus Sequences Integrate Near Cellular Oncogenes in Some Cervical Carcinomas," *PNAS USA* 84:1070-1074.

Dvoretzky et al. (1980) "A Quantitative in Vitro Focus Assay for Bovine Papilloma Virus", *Virol*. 103:369-375.

Eisinger et al. (1975)"Propagation of Human Wart Virus in Tissue Culture", *Nature* 256:432-434.

Ellis et al. (1997) "Antithrombotic and Antifibrinolytic Effects of Antithrombin III Replacement in Liver Cirrhosis", *The Lancet* 349:1069-1070.

Emeny et al. (1999) "Comparison of Variant-Specifc Hybridization and Single-Strand Conformational Polymorphism Methods for Detection of Mixed Human Papillomavirus Type 16 Variant Infections," *J. Clinical Microbiology* 37:3627-3633.

Fairlie et al. (1998) "Towards Protein Surface Mimetics", *Curr. Med. Chem*. 5:29-62.

Fang et al. (1999) "Post Translational Modifications of Recombinant Human Papillomavirus Type 6b Major Capsid Protein", *Virus Res*. 60:113-121.

Fang et al. (2000) "Differences in the Post-Translational Modifications of Human Papillomavirus Type 6b Major Capsid Protein Expressed from a Baculovirus System Compared with a Vaccinia Virus System", *Biotechnol. Appl. Biochem*. 32:27-33.

Favre et al. (1974) "Hemagglutinating Activity of Bovine Papilloma Virus," *Virology* 60: 572-578.

Favre et al. (1975) "Structural Polypeptides of Rabbit, Bovine, and Human Papillomaviruses," *J. Virol*. 15:1239-1247.

Favre et al. (1977) "Chromatin-Like Structures Obtained After Alkaline Disruption of Bovine and Human Papillomavirus," *J. of Virol*. 21:1205-1209.

Fenner et al.(1976) *Medical Virology Second Edition*, Academic Press, New York, NY pp. 359-374.

Fey et al. (1989) "Demonstration of in Vitro Synthesis of Human Papilloma Viral Proteins from Hand and Foot Warts", *J. Invest. Dermatol.* 92:817-824 (Abstract).

Fields et al. (1995) *Fields Virology* Third Edition pp. 475.

Fields et al. (1996) *Fields Virology* Third Edition. Lippincott Williams and Wilkins. pp. 2045, 2047, 2072-2073, 2075-2076.

Fields et al. (2001) *Fields Virology* Fourth Edition. Lippincott Williams and Wilkins. pp. 53, Fig 1, 2197, 2199, 2224-2225, 2227, 2229.

Fife et al. (2000) "A Dose-Ranging Study of the Safety and Immunogenicity Profiles of an HPV 11 L1 VLP Candidate vaccine in Young Health Women", Abstract 364.

Finch et al. (1965) "The Structure of Viruses of the Papilloma-Polyoma Type III. Structure of Rabbit Papilloma Virus", *J. Mol. Biol.* 13:1-12.

Fligge et al. (2001) "DNA-Induced Structural Changes in the Papillomavirus Capsid," *J. Virol.* 75:7727-7731.

Fligge et al. (2001) "Induction of Type-specific Neutralizing Antibodies by Capsomeres of Human Papillomavirus Type 33," *Virology* 283:353-357.

Flores et al. (1999) "Establishment of the Human Papillomavirus Type 16 (HPV-16) Life Cycle in an Immortalized Human Foreskin Keratinocyte Cell Line," *Virology* 262:344-354.

Florin et al. (2002) "Assembly and Translocation of Papillomavirus Capsid Proteins," *J. Virol.* 76:10009-10014.

Florin et al. (2004) "Nuclear Translocation of Papillomavirus Mino Capsid Protein L2 Requires Hsc70," *J. of Virol.* 78:5546-5553.

Forghani (1991) "Enzyme Immunoassay Systems" in *Laboratory Diagnosis of Viral Infections*, 2nd Edition, E.H. Lenette ed., Marcel Dekker NY, pp. 102-125.

French et al. (1990) "Assembly of Double-Shelled, Viruslike Particles of Bluetongue Virus by the Simultaneous Expression of Four Structural Proteins," *J. of Virol.* 64: 5694-5700.

French et al. (1990) "Synthesis of Bluetongue Virus (BTV) Corelike Particles by Recombinant Baculovirus Expressing the Two Major Structural Core Proteins of BTV", *J. of Virol.* 65:1530-1536.

Frommhagen (1965) "The Separation and Physiochemical Properties of the C and D Antigens of Coxsackievirus", *J. Immunol.* 95:818-22.

Galloway (1992) "Serological Assays for the Detection of HPV Antibodies", *IARC Sci. Publ.* 119:147-161.

Galloway (1994) "Papillomavirus Capsids: a New Approach to Identify Serological Markers of HPV Infection", *J. Nat'l Canc. Inst.* 86:474-475.

Gardas et al. (1988) "Coating of Proteins to Polystyrene ELISA Plates in the Presence of Detergents", *J. Immunological Methods* 106: 251-255.

Genbank Accession AAN99662, 2002.
Genbank Accession AF125673, 2000.
Genbank Accession NC_001356, 2005.
Genbank Accession U34185, 1996.

Ghadially, (1997) "The Nuclear Matrix and Interchromatin and Perichromatin Granules and Intranuclear Viral Inclusions and Virus-Like Particles" in *Ultrastructural Pathology of the Cell and Matrix*, vol. 1:30-35 and 136-145 (4th ed.)..

Gheysen et al. (1989) "Assembly and Release of HIV-1 precursor Pr55$^{gag}$ Virus-like Particles from Recombinant Baculovirus-Infected Insect Cells," *Cell* 59:103-112.

Ghim et al. (1991) "Comparison of Neutralization of BPV-1 Infection of C127 Cells And Bovine Fetal Skin Xenografts", *Int. J. Cancer* 49:285-289.

Ghim et al. (1992) "HPV-1 L1 Protein Expressed in Cos Cells Displays Conformational Epitopes Found on Intact Virions", *Virology* 190:548-552.

Ghim et al.(1993) "Identification of Conformational Epitopes of the BPV-1 Capsid Recognized by Competitive Inhibition of Sera from Infected or Immunized Animals", *Pathobiology* 61:138-144.

Ghim et al. (1994) "Papilloma Extracts and Recombinant L1 Protein Protect Completely Against Mucosal Papillomavirus Infection: a Canine Model", *Programme & Abstract Book, 13th Intl. Papillomavirus Conf.*, Amsterdam, p. 56.

Gluzman (1981) "SV40-Transformed Simian Cells Support the Replication of Early SV40 Mutants," *Cell* 23:175-182.

Gigler et al. (1999) "Generation of Neutralizing Human Monoclonal Antibodies against Parvovirus B19 Proteins," *J. of Virol.* 73:1974-1979.

Giri et al. (1986) "Papillomavirus Genomes: From Sequence Data to Biological Properties", *Trends Genet.* 2:227-232.

Giroglou et al. (2001) "Immunological Analyses of Human Papillomavirus Capsids", *Vaccine* 19:1783-1793.

Gissmann et al. (1987) "Human Papillomaviruses and Cervical Cancer", *Cancer Cells* 5:275-280.

Gissman et al. (1993) "Immune Response to Genital Papillomavirus Infection in Women." *Annals of the New York Academy of Sciences* 690:80-85.

Goldstein et al. (1990) "The E5 Oncoprotein of Bovine Papillomavirus Binds to a 16 kd Cellular Protein," *EMBO J.* 9:137-145.

Gravitt et al. (2000) "Improved Amplification of Genical Human Papillomaviruses," *Journal of Clinical Microbiology* 38:357-361.

Grubman et al. (1985) "Capsid Intermediates Assembled in a Foot-and-Mouth disease Virus Genome RNA-Programmed Cell-Free Translation System and in Infected Cells", *J. of Virol.* 56:120-128.

Hagensee et al. (1993) "Self-Assembly of Human Papillomavirus Type 1 Capsids by Expression of the L1 Protein Alone or Coexpression of the L1 and L2 Capsid Proteins", *J. of Virol.* 67:315-322.

Hagensee et al. (1994) "Three-Dimensional Structure of Vaccinia Virus-Produced Human Papillomavirus Type I Capsids", *J. of Virol.* 68:4503-4505.

Hagensee et al. (1995) "Immunization of Mice with HPV Vaccinia Virus Recombinants Generates Serum IgG, IgM, and Mucosal IgA Antibodies", *Virology* 206:174-182.

Hagensee et al. (2000) "Detection of Cervical Antibodies to Human Papillomavirus Type 15 (HPV-16) Capsid Antigens in Relation to Detection of HPV-16 DNA and Cervical Lesions", *J. Infect. Dis.* 181:1234-1239.

Halbert et al. (1988) "Identification of the E5 Open Reading Frame of Human Papillomavirus Type 16," *J. of Virol.* 62:1071-1075.

Hamšiková et al. (1997) "Correlation between the Presence of Anti HPV33 VLP antibodies and HPV DNA in Cervical Neoplasia Patients," *Arch. Virol.* 142: 413-416.

Hamšiková et al. (1988) "Prevalence of Antibodies to Human Papillomaviruses in the General Population of the Czech Republic," *Int. J. Cancer* 77:689-694.

Harper (1998) *Molecular Virology*, 2nd ed. BIOS Scientific Publishers Limited. p. 1.

Harrison (1991) "Principles of Virus Structure", *Fundamental Virology*, Second Ed. Fields, ed. p. 37-38.

Harrison (2001) "Principles of Virus Structures", in *Fields Virology*, Fourth Ed. pp. 53-85.

Harro et al. (2000) "A Safety and Immunogenicity Trial of Human Papillomavirus Type 16 L1 Virus-like Particle Vaccine in Healthy Young Adult Human Volunteers", *18th International Papillomavirus Conference* (Abstract).

Hartig (1991) "Generation of Recombinant Baculovirus Via Liposome-Mediated Transfection", *BIotechniques* 11:310-312.

Heim et al. (1995) "Serum IgG, IgM, and IgA Reactivity to Human Papillomavirus Types 11 and 6 Virus-like Particles in Different Gynecologic Patient Groups," *J. Infect. Dis.* 172:395-402.

Heino et al. (1995) "Human Papillomavirus Type 16 Capsids Expose Multiple Type-Restricted and Type-Common Antigenic Epitopes", *J. Gen. Virol.* 76:1141-1153.

Hewat et al. (1992) "Three-Dimensional Reconstruction of Baculovirus Expressed Bluetongue Virus Core-Like Particles by Cryo-Electron Microscopy", *Virology* 189:10-20.

Hilleman et al. (1993) "The Preparation and Safety of Hepatitis B Vaccine", *J. Infection* 7(Supp. I):3-8.

Hines et al. (1994) "Role of Conformational Epitopes Expressed by Human Papillomavirus Major Capsid Proteins in the Serologic Detection of Infection and Prophylactic Vaccination", *Gyn. Onco.* 55:13-20.

Hines et al. (1994) "The Expressed L1 Proteins of HPV-1, HPV-6, and HPV-11 Display Type-Specific Epitopes with Native Conformation and Reactivity with Neutralizing and Nonneutralizing Antibodies", *Pathobiology* 62:165-171.
Ho et al. (1991) "Sequence Variants of Human Papillomavirus Type 16 in Clinical Samples Permit Verification and Extension of Epidemiological Studies and Construction of a Phylogenetic Tree," *J. Clinical Microbiology* 29:1765-1772.
Hofmann et al. (1995) "Sequence Determination of Human Papillomavirus Type 6a and Assembly of Virus-Like Particles in *Saccaromyces cerevisiae*", *Virology* 209:506-518.
Hopfl et al. (1991) "Skin Test for HPV Type 16 Proteins in Cervical Intraepithelial Neoplasia", *Lancet* 337:373-374.
Hoskins (1967) "Collection & Preparation of Clinical Specimens", *Virology Procedures*. Butterworth & Co. Pub. Ch. 7, p. 105-111, 120-127.
Howley (1991) "Papillomavirinae and Their Replication", *Fundamental Virology* (2nd ed.) Raven Press, New York, Chapter 30, pp. 743-768.
Icenogle, et al. (1991) "Nucleotide and Amino Acid Sequence Variation in the L1 and E7 Open Reading Frames of Human Papillomavirus Type 6 and Type 16," *Virology* 184:101-107.
"Immunotherapeutic products will have $2.4 billion European market in 1995", (1992) *Biotechnology News* 12.2.
In this issue: New Test for HPV16 (1994) *J. Nat. Cancer Inst.* 86:473.
Iwaski et al. (1992) "Detection Of Capsid Antigen Of Human Papillomavirus (HPV) In Benign Lesions Of Female Genital Tract Using Anti-HPV Monoclonal Antibody," *J. of Pathology* 168:293-300.
Jahrling et al. (1990) "Preliminary Report: Isolation of Ebola Virus from Monkeys Imported to USA," *The Lancet* 335: 502-505.
Janeway et al. (2001) "The detection, measurement, and characterization of antibodies and their use as research and diagnostic tools," *Immuno. Biology 5*. Published by Garland Publishing. p. 618-620.
Jansen et al. (1995) "Vaccination with Yeast-Expressed Cottontail Rabbit Papillomavirus (CRPV) Virus-Like Particles Protects Rabbits from CRPV-Induced Papilloma Formation", *Vaccine* 13:1509-1514.
Jarrett et al. (1990) "Studies on Vaccination Against Papillomaviruses: a Comparison of Purified Virus, Tumour Extract and Transformed Cells in Prophylactic Vaccination", *Veterinary Record* 126:449-452.
Jarrett et al. (1991) "Studies on Vaccination against Papillomaviruses: Prophylactic and Therapeutic Vaccination with Recombinant Structural Proteins", *Virology* 184:33-42.
Jemmerson (1987) "Antigenicity and Native Structure of Globular Proteins: Low Frequency of Peptide Reactive Antibodies," *PNAS USA* 84:9180-9184.
Jenison et al. (1990) "Evidence of Prevalent Genital-Type Human Papillomavirus Infections in Adults and Children", *J. Infect. Dis.* 162:60-69.
Jenkins et al. (1990) "An Antigen Chimera of Poliovirus Induces Antibodies against Human Papillomavirus Type 16", *J. of Virol.* 64:1201-1206.
Jensen et al. (1964) "Infection of Human and Simian Tissue Cultures with Rous Sarcoma Virus," *PNAS USA* 52:53-59.
Jenson et al. (1980) "Immunologic Relatedness of Papillomaviruses from Different Species", *J. Natl. Cancer Inst.* 64:495-500.
Jenson et al. (1991) "Identification of Linear Epitopes of te BPV-1 L1 Protein Recognized by Sera of Infected or Immunized Animals", *Pathobiology* 59:396-403.
Jenson et al. (1997) "Multiplicity of Uses of Monoclonal Antibodies That Define Papillomavirus Linear Immunodominant Epitopes," *Immunologic Research* 16: 115-119.
Jeon et al. (1995) "Integration of Human Papillomavirus Type 16 into the Human Genome Correlates with a Selective Growth Advantage of Cells," *J. Virol.* 69:2989-2997.
Jewers et al. (1991) "The E5 Proteins of HPVs 16 and 6 have Transforming Activity both Murine Cells and Primary Human Keratinocytes". Abstract. *1991 Papillomavirus Workshop*. Jul. 20 to Jul. 26. Seattle, Washington.
Jin et al. (1989) "Identification of L2 Open Reading Frame Gene Products of Bovine Papillomavirus Type 1 Using Monoclonal Antibodies", *J. Gen. Virol.* 70:1133-1140.

Jin et al. (1990) "Bovine Serological Response to a Recombinant BPV-1 Major Capsid Protein Vaccine", *Intervirology* 31:345-354.
Joklik et al. (1985) "The Nature, Isolation, and Measurement of Animal Viruses" *Virology*, 2nd ed. Appleton-Century-Crofts Pub. p. 3-13.
Kadish (1994) "Recombinant Virus-like Particles Retain Conformational Epitopes of Native Human Papillomavirus and May Be Useful for Vaccine Development," *Gynecol. Oncol.* 55:10-12.
Kajigaya et al. (1991) "Self-Assembled B19 Parvovirus Capsids, Produced in a Baculovirus System, are Antigenically and Immunogenically Similar to Native Virions", *PNAS USA* 88:4646-4650.
Kang et al. (1987) "Secretion of Particles of Hepatitis B Surface Antigen From Insect Cells Using a Baculovirus Vector", *J. Gen. Virol.* 68:2607-2613.
Karacostas et al. (1989) "Human Immunoefficiency Virus-Like Particles Produced by a Vaccinia Virus Expression Vector", *PNAS USA* 86:8964-8967.
Karasuyama et al.(1988) "Establishment of Mouse Cell Lines Which Constitutively Secrete Large Quantities of Interleukin 2, 3, 4 or 5, Using Modified cDNA Expression Vectors", *Eur. J. Immunol* 18:97-104.
Kawana et al. (1999) "Common Neutralization Epitope in Minor Capsid Protein L2 of Human Papillomavirus Types 16 and 6," *J. of Virol.* 73:6188-6190.
Kienzler et al. (1983) "Humoral and Cell-Mediated Immunity to Human Papillomavirus Type 1 (HPV-1) in Human Warts", *Br. J. Dermatol.* 108:665-672.
Kirnbauer et al. (1992) "BPV L1 Assembled Into Capsid-Like Structures In Insect Cells Generates High Titer Neutralizing Antisera", *11th International Papillomavirus Workshop*, Edinburgh Conference Centre, Herlot-Watt University, Sep. 5-11, 1992, p. 17 Abstract.
Kirnbauer et al. (1992) "Papillomavirus L1 Major Capsid Protein Self-Assembles into Virus-Like Particles that are Highly Immunogenic", *PNAS USA* 89:12180-12184.
Kirnbauer et al. (1993) "Efficient Self-Assembly of Human Papillomavirus Type 16 L1 and L1-L2 into Virus-Like Particles", *J. of Virol.* 67:6929-6936.
Kirnbauer et al. (1993) "Human Papillomavirus Type 16 Virus-like Particles: Elisa to Detect High Risk HPV Infection and Potential for a Preventive Vaccine", *Investigative Dermatology* 101:393 Abstract 31.
Kirnbauer et al. (1993) "Papillomavirus L1 Major Capsid Protein: Self-assembly into Particles That Are Morphologically and Immunologically Similar to Native Virions". In: *Vaccines '93*, Ginsberg, H.S. et al., Editor, Cold Spring Harbor Laboratory Press, pp. 305-310.
Kirnbauer et al. (1994) "A Vaccine of Virus-Like Particles Made in Insect Cells can Inhibit Papillomavirus Infection of Rabbits", *Programme & Abstract Book, 13th Intl. Papillomavirus Conf.*, Amsterdam, p. 154.
Kirnbauer et al. (1994) "A Vaccine of Virus-Like Particle Enzyme-Linked Immunosorbent Assay Detects Serum Antibodies in a Majority of Women Infected With Human Papillomavirus Type 16", *J. Nat'l Canc. Inst.* 86:494-499.
Kirnbauer et al. (1996) "Virus-like Particles of Bovine Papillomavirus Type 4 in Prophylactic and Therapeutic Immunization", *Virology* 219:37-44.
Kjellberg et al. (1999) "Sexual Behavior and Papillomavirus Exposure in Cervical Intraepithelial Neoplasia: A Population-based Case-control Study," *J. Gen. Virol.* 80: 391-398.
Knipe et al., eds. (2001) "Description of Insect Virus Families", *Fields Virology* 4th ed. Lippincott Williams and Wilkins, p. 602-603.
Kols et al. (2000) "HPV Vaccines: Promise and Challenges", *Alliance for Cervical Cancer Prevention*, Seattle, Washington, pp. 1-40.
Kossovsky et al. (1991) "Nanocrystalline Epstein-Barr Virus Decoys", *J. Appl. Biomater.* 2:251-259.
Koutsky et al (2001) 19th International Papillomavirus Conference, Brazil, Abstract O-50.

Koutsky et al. (2002) "A Controlled Trail of a Human Papillomavirus Type 16 Vaccine," *N. Engl. J. Med.* 347:1645-1651.

Kreider et al. (1986) "In Vivo Transformation of Human Skin with Human Papillomavirus Type 11 from *Condylomata acuminata*", *J. of Virol.* 59:369-376.

Kremsdorf et al. (1983) "Human Papillomaviruses Associated with *Epidermodysplasia verruciformis*", *J. of Virol.* 48:340-351.

Kuby (1992) *Immunology*. Published by W.H. Freeman and Company. p. 133-136.

Kuby (1992) *Immunology*. Published by W.H. Freeman and Company. p. 83 and figures.

Lancaster et al. (1975) "Persistence of Viral DNA in Human Cell Cultures Infected with Human Papillomavirus", *Nature* 256:434-436.

Lancaster et al. (1978) "Demonstration of Two Distinct Classes of Bovine Papilloma Virus," *Virology* 89: 372-379.

Lancaster et al. (1982) "Animal Papillomaviruses", *Microbiol. Rev.* 46:191-207.

Larsen et al. (1987) "Proteins Present in Bovine Papillomavirus Particles", *J. of Virol.* 61:3596-3601.

Laurent et al. (1982) "Two Anatomical Types of Warts with Plantar Localization: Specific Cytopathogenic Effects of Papillomavirus", *Arch Dermatol. Res.* 274: 101-111.

Le Bouvier et al. (1966) "Antigenic Diversity of Mammalian Papillomaviruses", *J. Gen. Microbiol.* 45:497-501.

Le Cann et al. (1994) "Self-assembly of Human Papillomavirus Type 16 Capsids by Expression of the L1 Protein in Insect Cells," *FEMS Microbiol. Lett.* 117:269-274.

Le Cann et al. (1995) "Detection of Antibodies against Human Papillomavirus (HPV) Type 16 Virions by Enzyme-Linked Immunosorbent Assay Using Recombinant HPV 16 L1 Capsids Produced by Recombinant Baculovirus", *J. Clin. Microbiol.* 33:1380-1382.

Leder et al. (2001) "Enhancement of Capsid Gene Expression: Preparing the Human Papillomavirus Type 16 Major Structural Gene L1 for DNA Vaccination Purposes," *J. of Virol.* 75: 9201-9209.

Lehtinen et al. (1990) "Demonstration of Evolutionary Differences Between Conserved Antigenic Epitopes in the Minor Nucleocapsid Protein of Human Papillomavirus Types", *Biochemical and Biophysical Research Communications* 172:1378-1383.

Li et al. (1987) "Identification of the Human Papillomavirus Type 6b L1 Open Reading Frame Protein in Condylomas and Corresponding Antibodies in Human Sera", *J. of Virol.* 61:2684-2690.

Li et al. (1997) "Expression of the Human Papillomavirus Type 11 L1 Capsid Protein in *Escherichia coli*: Characterization of Protein Domains Involved in DNA Binding and Capsid Assembly," *J. of Virol.* 71:2988-2995.

Liddington et al. (1991) "Structure of simian virus 40 at 3.8-A resolution", *Nature* 354:278-284.

Lin et al. (1992) "Effective Vaccination against Papilloma Development by Immunization with L1 or L2 Structural Protein of Cottontail Rabbit Papillomavirus", *Virology* 187:612-619.

Lin et al. (1993) "Cottontail Rabbit Papillomavirus L1 Protein-Based Vaccines: Protection is Achieved only with a Full-Length, Nondenatured Product", *J. of Virol.* 67:4154-4162.

Liu et al. (1997) "Sequence Close to the N-terminus of L2 Protein Is Displayed on the Surface of Bovine Papillomavirus Type 1 Virions," *Virology* 227:474-483.

Liu (1998) "Mucosal Immunisation with Papillomavirus Virus-like Particles Elicits Systemic and Mucosal Immunity in Mice," *Virology* 252:39

Liu et al. (2001) "Efficiency of Delivery of DNA to Cells by Bovine Papillomavirus Type-1 L1/L2 Pseudovirions", *Appl. Microbiol. Biotechnol.* 56:150-156.

Lonberg-Holm et al. (1973) "Antigenic Determinants of Infective and Inactivated Human Rhinovirus Type 2", *J. of Virol.* 12:114-123.

Lopez de Turiso et al. (1992) "Recombinant Vaccine for Canine Parvovirus in Dogs", *J. of Virol.* 66:2748-2753.

Lorincz (1989) "Human Papillomavirus Testing", *Diagnostical & Clinical Testing* 27:28-37.

Loudon et al. (1991) "Assembly of Five Bluetongue Virus Proteins Expressed by Recombinant Baculoviruses: Inclusion of the Largest protein VP1 in the Core and Virus-like Particles", *Virology* 180:798-802.

Lowe et al. (1997) "Human Papillomavirus Type 11 (HPV-11) Neutralizing Antibodies in the Serum and Genital Mucosal Secretions of African Green Monkeys Immunized with HPV-11 Virus-Like Particles Expressed in Yeast", *J. Infectious Diseases* 176:1141-1145.

Lowy et al. (1994) "Genital Human Papillomavirus Infection", *PNAS USA* 91:2436-2440.

Lowy et al. (1998) "Papillomaviruses and Cervical Cancer: Pathogenesis and Vaccine Development", *J. National Cancer Institute Monographs* 23:27-30.

Lowy et al. (2001) "Papillomaviruses", in *Fields Virology* 4th Edition, vol. 2, pp. 2231-2264.

Luckow (1991) "Cloning and Expression of Heterologous Genes in Insect Cells with Baculovirus Vectors", in *Recombinant DNA Technology and Applications*, (A. Prokop. R.K. Bajpai and C. Ho, editors) McGraw Hill, New York, NY pp. 97-152.

Luckow et al. (1988) "Trends in the Development of Baculovirus Expression Vectors", *Bio/Technology* 6:47-55.

Ludmerer et al. (1996) "Glutamate May Substitute For ASP1999 and ASP202 in the Assembly of HPV1 and HPV16 VLPS", *15th International Papillomavirus Workshop*, Dec. 6-9, 1996 Abstract.

Ludmerer et al. (1996) "Two Amino Acid Residues Confer Type Specificity to a Neutralizing, Conformationally Dependent Epitope on Human Papillomavirus Type 11", *J. of Virol.* 70:4791-4794.

Ludmerer et al. (2000) "HPV11 Mutant Virus-like Particles Elicit Immune Responses That Neutralize Virus and Delineate a Novel Neutralizing Domain", *Virology* 266: 237-245.

Madeley et al. (1972) "Human Wart Virus", *Virus Morphology*, Williams and Wilkins Company, Baltimore, p. 128.

Mahy, ed. (1985) "Virus Isolation and Purification", *Virology: a practical approach*. IRL Press Ltd. p. 87-90.

Man et al. (1989) "Treatment of Human Muscle Creatine Kinase with Glutaraldehyde Preferentially Increases the Immunogenicity of the Native Conformation and Permits Production of High-Affinity Monoclonal Antibodies which Recognize Two Distinct Surface Epitopes", *Journal of Immunological Methods*, 125:251-259.

Mansur et al. (1993) "Cellular Transformation by Papillomavirus Oncoproteins", *Biochim. Biphys. Acta.* 1155:323-345.

Martinez et al. (1992) "Production of Porcine Parvovirus Empty Capsids with High Immunogenic Activity", *Vaccine* 10:684-690.

Mayer et al. (1957) "The Purification of Poliomyelitis Virus as Studied by Complement Fixation", *J. Immunol.* 78:435-455.

McAleer et al. (1984) "Human hepatitis B vaccine from Recombinant Yeast", *Nature* 307:178:180.

McCabe et al. (1988) "The Effects of Detergent on the Enzyme-Linked Immunosorbent Assay (ELISA) of Blood Group Substances", *J. Immunological Methods* 108:129-135.

McCarthy et al. (1998) "Quantitative Disassembly and Reassembly of Human Papillomavirus Type 11 Viruslike Particles In Vitro", *J. of Virol.* 72:32-41.

McLean et al. (1990) "Production of Characterisation of a Monoclonal Antibody to Human Papillomavirus Type 16 Using Recombinant Vaccinia Virus", *J. Clin. Pathol.* 43:488-492.

McNeil et al. (1997) "News: HPV Vaccines for Cervical Cancer Move Toward Clinic, Encounter Social Issues", *J. Nat'l Canc. Inst.* 89:1664-1666.

MEDIMMUNE (2001) Website showing R& D Pipeline.

Meissner (1999) "Nucleotide Sequences and Further Characterization of Human Papillomavirus DNA Present in the CaSki, SiHa and HeLa Cervical Carcinoma Cell Lines", *J. of Gen. Virol.* 80:1725-1733.

Miller et al. (1986) "An Insect Baculovirus Host Vector for High Level Expression of Foreign Genes", in *Genetic Engineering* (J. K. Settow and A Hollander editors) Plenum Press pp. 277-298.

Miller (1988) "Baculoviruses as Gene Expression Vectors", *Annu. Rev. Microbiol.* 42:177-199.

Miyanohara et al. (1983) "Expression of Hepatitis B Surface Antigen Gene in Yeast", *PNAS USA* 80:1-5.

Morikawa et al. (1991) "Analysis of the Requirements for the Synthesis of Virus-like Particles by Feline Immunodeficiency Virus gag Using Baculovirus Vectors," *Virology* 183:288-297.

Montross et al. (1991) "Nuclear Assembly of Polyomavirus Capsids in Insect Cells Expressing the Major Capsid Protein VP1", *J. of Virol.* 65:4991-4998.

Muller et al. (1995) "Papillomavirus Capsid Binding and Uptake by Cells from Different Tissues and Species", *J. of Virol.* 69:948-954.

Muller et al. (1997) "Chimeric Papillomavirus-Like Particles," *Virology* 234:93-111.

Murphy et al. (1991) "Immunization against Viruses", *Fundamental Virology*, 2nd ed. Chap. 15 p. 371-404.

Murphy et al. (2001) "Immunization Against Viral Diseases", in *Fields Virology*, 4th ed. Lippincott Williams & Wilkins. p. 435, 436.

Nakai et al. (1986) "Monoclonal Antibodies to Genus- and Type-Specific Papillomavirus Structural Antigens", *Intervirol.* 25:30-37.

Nakamura et al. 1986. In Handbook Exp. Immunol., (Weir, D.M. ed.) Blackwell Scientific Publishing) vol. 1, "Immunochemistry", Ch. 27. p. 27.15-27.18.

Nakano (1991) "Human Poxvirus Diseases" in: *Laboratory Diagnosis of Viral Infections* p. 401-421.

Nardelli-Haefliger et al. (1997) "Human Papillomavirus Type 16 Virus-Like Particles Expressed in Attenuated *Salmonella typhimurium* Elicit Mucosal and Systemic Neutralizing Antibodies in Mice", *Infect. and Immun.* 65:3328-3336.

Nayak et al. (1985) "Biological and Immunological Properties of Haemagglutinin and Neuraminidase Expressed from Cloned cDNAs in Prokaryotic and Eukaryotic Cells", *Vaccine* 3(Suppl):165-171.

Neeper et al. (1996) "Expression of the Major Capsid Protein of Human Papillomavirus Type 11 in *Saccharomyces cerevisae*", *Gene* 180:1-6.

Nicholls et al. (1999) "Naturally Occurring, Nonregressing Canine Oral Papillomavirus Infection: Host Immunity, Virus Characterization, and Experimental Infection," *Virology* 265:365-374.

Nicholls et al. (2000) "The Immunology of Animal Papillomaviruses", *Veterinary Immunology and Immunopathology* 73:101-127.

Nonnenmacher et al. (1995) "Serologic Response to Human Papillomavirus Type 16 (HPV-16) Virus-like Particles in HPV-16 DNA-Positive Invasive Cervical Cancer and Cervical Intraepithelial Neoplasia Grade III Patients and Controls from Colombia and Spain," *J. Infect. Dis.* 172:19-24.

Ochsenbein et al. (2000) "Correlation of T Cell Independence of Antibody Responses with Antigen Dose Reaching Secondary Lymphoid Organs: Implications for Splenectomized Patients and Vaccine Design", *J. Immun.* 164:6296-6302.

Okun et al. (2004) "L1 Interaction Domains of Papillomavirus L2 Necessary for Viral Genome Encapsidation," *J. of Virol.* 75:4332-4342.

Olson et al. (1960) "Further Observations on Immunity to Bovine Cutaneous Papillomatosis", *Amer. J. Vet. Res.* 21:233-242.

Olson (1963) "Cutaneous Papillomatosis in Cattle and Other Animals", *Ann NY Acad. Sci.* 108:1042-1056.

Olson et al. (1969) "Oncogenicity of Bovine Papilloma Virus", *Arch. Environ. Health* 19:827-837.

Ostrow et al. (1990) "A Rhesus Monkey Model for Sexual Transmission of a Papillomavirus Isolated from a Squamous Cell Carcinoma", *PNAS USA* 87:8170-8174.

Ostrow et al. (1991) "Characterization of the Complete RhPV 1 Genomic Sequence and Integration Locus from a Metastatic Tumor", *Virology* 181:424-429.

Ozawa et al. (1987) "Novel Transcription Map for the B19 (Human) Pathogenic Parvovirus", *J. of Virol.* 61:2395-2406.

Paintsil et al. (1996) "Carboxyl Terminus of Bovine Papillomavirus Type-1 L1 Protein is Not Required for Capsid Formation", *Virology* 223:238-244.

Parton (1990) "Nucleotide Sequence of the HPV16 L1 Open Reading Frame", *Nucl. Acids Res.* 18:3631.

Pass et al. (1973) "Wart-Associated Antigens. II. Human Immunity to Viral Structural Proteins," *J. Investigative Dermatology* 60:307-311.

Perbal et al. (1983) "Molecular Biology of Polyomaviruses and Herpesviruses" p. 3-48.

Pettersson et al. (1987) *The Papaviridae*, vol. 2. Salzman & Howely eds. Capt. 3 p. 67-107.

Pfister et al. (1979) "Seroepidemiologic Studies of Bovine Papillomavirus Infections", *J. Natl. Cancer Inst.* 62:1423-1425.

Pfister (1984) "Biology and Biochemistry in Papillomaviruses", *Rev. Physiol. Biochem. Pharmacol.* 99:111-181.

Pfister et al. (1987) "Papillomaviruses: Particles, Genome Organisation and Proteins", in *Papillomaviruses and Human Disease* (Syrjänen et al. eds.) Springer Verlag p. 2-18.

Pfister et al. (1994) "Anatomy, Taxonomy and Evolution of Papillomaviruses", *Intervirol.* 37:143-149.

Pilacinski et al. (1984) "Cloning and Expression in *Escherichia coli* of the Bovine Papillomavirus L1 and L2 Open Reading Frames", *Bio/Technology* pp. 356-360.

Pilacinski et al. (1986) "Immunization against Bovine Papillomavirus Infection", *CIBA Found. Symp.* 120:136-156.

Poland et al. (2000) "A Randomized, Double-Blind, Placebo-Controlled Trial of the Immunogenicity and Reactogenicity of a Novel HPV 16 Vaccine: Preliminary Results", Abstract 363.

Ponten et al. (1995) "Strategies for Global Control of Cervical Cancer", *Int'l J. Cancer* 60:1-26.

Pringle (1993) "Virus Taxonomy Update", *Arch. Virol.* 133:491-495.

Provost et al. (1987) "Successful Infection of the Common Marmoset (*Callithrix jacchus*) with Human Varicella-Zoster Virus," *J. of Virol.* 61: 2951-2955.

Pushko et al. (1994) "Sequence Variation in the Capsid Protein Genes of Human Papillomavirus Type 16," *J. Gen. Virol.* 75:911-916.

Rasmussen et al. (1990) "Characterization of Virus-like Particles Produced by a Recombinant Baculovirus Containing the gag Gene of the Bovine Immunodeficiency-like Virus," *Virology* 178:435-451.

Reichmann et al. (1990) "Treatment of *Condyloma acuminatum* with Three Different Interferon-α Preparations Administered Parenterally: A Double-Blind, Placebo-Controlled Trial," *J. Infect. Dis.* 162:1270-1276.

Reid et al. (1996) "New Generation of Human Papillomavirus Tests, in Cervical Cancer & Preinvasive Neoplasia" pp. 27-47 (Rubin and Hoskins eds., Philadelphia).

Rieger et al. (1991) "Glossary of Genetics Classical and Molecular", Fifth Edition, Springer-Verlag, Berlin Heidelberg.

Robinson. (1990) *Principles and Practice of Infectious Diseases, Third ed.* Mandell, Douglas and Bennett (eds) Churchill Livingston Inc. Chapter 125: Hepatitis B virus and Hepatitis Delta Virus. pp. 1204-1231.

Roden et al. (1994) "Interaction of Papillomaviruses with the Cell Surface", *J. of Virol.* 68:7260-7266.

Roden et al. (1994) "Neutralization of Bovine Papillomaviruses with the Cell Surface", *J. of Virol.* 68:7260-7266.

Roden et al. (1995) "Papillomavirus L1 Capsids Agglutinate Mouse Erythrocytes through a Proteinaceous Receptor", *J. of Virol.* 69:5147-5151.

Roden et al. (1996) "Assessment of the Serological Relatedness of Genital Human Papillomaviruses by Hemagglutination Inhibition", *J. of Virol.* 70:3298-3301.

Roden et al. (1996) "In Vitro Generation and Type-Specific Neutralization of a Human Papillomavirus Type 16 Virion Pseudotype", *J. of Virol.* 70:5875-5883.

Roden et al. (1997) "Characterization of a Human Papillomavirus Type 16 Variant-Dependent Neutralizing Epitope", *J. of Virol.* 71:6247-6252.

Roden et al. (1997) "Papillomavirus Is Resistant to Desication," *J. Infect. Dis.* 176: 1076-1079.

Roden et al. (2000) "Minor Capsid Protein of Human Gential Papillomaviruses Contains Subdominant, Cross-Neutralizing Epitopes" *Virology* 270:254-257.

Roitt et al. (1985) *Immunology*. Gower Medical Publishing p. 6.1-6.6.

Rombaut et al. (1990) "Disoxaril Stabilization and Immunogenicity of Poliovirus Procapsids," *J. Gen. Virol.* 71: 1081-1086.

Rombaut et al. (1997) "Immunogenic, Non-Infectious Polio Subviral Particles Synthesized in *Saccharomyces cerevisiae*", *J. Gen. Virol.* 78:1829-1832.

Rommel et al. (2005) "Heparan Sulfate Proteoglycans Interact Exclusively with Conformationally Intact HPV L1 Assemblies: Basis for a Virus-like Particle ELISA," *J. Med. Virol.* 75:114-121.

Rose et al. (1990) "Expression of the Full-Length Products of the Human Papillomavirus Type 6b (HPV-6b) and HPV-11 Open Reading Frames by Recombinant Baculovirus, and Antigenic Comparisons with HPV-11 Whole Virus Particles", *J. Gen. Virology* 71:2725-2729.

Rose (1992) "Recombinant Baculovirus-mediated Production of Non-Infectious Human Papillomavirus Type 11 (HPV-11) Virus-like Particles (VLPs)", *MBI 501 Student Seminar Series, Abstract*.

Rose et al. (1993) "Expression of Human Papillomavirus Type 11 L1 Protein in Vivo and In Vitro Assembly of Viruslike Particles", *J. of Virol.* 67:1936-1944.

Rose et al. (1994) "Serological Differentiation of Human Papillomavirus Types 11, 16 and 18 Using Recombinant Virus-Like Particles", *J. Gen. Virol.* 75:2445-2449.

Rose et al. (1994) "Human Papillomavirus (HPV) type 11 Recombinant Virus-Like Particles Induce the Formation of Neutralizing Antibodies and Detect HPV-Specific Antibodies in Human Sera", *J. Gen. Virol.* 75:2075-2079

Rose et al. (1994) "Seroresponses of Patients wtih HPV-6, -16, -18, or -31 infections to Recombinant HPV-11,-16, and -18 Virus Like Particles (VLPs)", *13th Intl. Papillomavirus Conf.*, Amsterdam p. 328.

Rose et al. (1994) "Antigenic Cross r=Reactivity Between HPV6 and HPV11", *13th Intl. Papillomavirus Conf.*, Amsterdam p. 328.

Rose et al. (1998) "Human Papillomavirus Type 11 Recombinant L1 Capsomeres Induce Virus-Neutralizing Antibodies", *J. of Virol.* 72:6151-6154.

Rosel et al. (1985) "Transcriptional and Translational Mapping and Nucleotide Sequence Analysis of a Vaccinia Virus Gene Encoding the Precursor of the Major Core Polypeptide 4b," *J. of Virol.* 56:830-838.

Roseto et al. (1984) "Monoclonal Antibodies to the Major Capsid Protein of Human Papillomavirus Type 1", *J. Gen. Virol.* 65:1319-1324.

Rowlands et al. (1975) "A Comparative Chemical and Serological Study of the Full and Empty Particles of Foot-and-Mouth Disease Virus", *J. Gen. Virol.* 26:277-238.

Rowlands et al. (1992) "How can Peptide Vaccines Work?" *FEMS Microbiol. Lett.* 100:479-482.

Roy et al. (1990) "Recombinanat Virus Vaccine for Bluetoungue Disease in Sheep", *J. of Virol.* 64:1998-2003.

Sabara et al. (1991) "Assembly of Double-Shelled Rotaviruslike Particles by Simultaneous Expression of Recombinant VP6 and VP7 Proteins", *J. of Virol.* 65:6994-6997.

Saiki et al. (1988) "Primer-Directed Enzymatic Amplification of DNA with a Thermostable DNA Polymerase", *Science* 239:487-491.

Salunke et al. (1986) "Self-Assembly of Purified Polymavirus Capsid Protein $VP_1$", *Cell* 46: 895-904.

Salunke et al. (1989) "Polymorphism in the Assembly of Polyomavirus Capsid Protein $VP_1$", *Biophys. J.* 56:887-900.

Sambrook et al. (1989) "Expression of Cloned Genes in Cultured Mammalian Cells", *Molecular Cloning: A Laboratory Manual*, Cold Spring Harbor Laboratory, Ch. 16 pp. 1-72.

Sapp et al. (1994) "Analysis of Type-Restricted and Cross-Reactive Epitopes on Virus-Like Particles of Human Papillomavirus Type 33 and in Infected Tissues Using Monoclonal Antibodies to the Major Capsid Protein", *J. Gen. Virol.* 75:3375-3383.

Sapp et al. (1995) "Organization of the Major and Minor Capsid Protein in Human Papillomavirus Type 33 Virus-Like Particles," *J. Gen. Virol.* 76:2407-2412.

Sapp et al. (1996) "Synthesis, Properties and Applications of Papillomavirus-like Particles", *Intervirology* 39:49-53.

Sapp et al. (1998) "Papillomavirus Assembly Requires Trimerization of the Major Capsid Protein by Disulfides between Two Highly Conserved Cysteines", *J. of Virol.* 72:6186-6189.

Sarver et al. (1982) "Transformation and Replication in Mouse Cells of a Bovine Papillomavirus-pML2 Plasmid Vector That can be rescued in Bacteria", *PNAS USA* 79: 7147-7151.

Sasagawa et al. (1994) "Synthesis and Assembly of Virus-Like Particles of the Human Type Papillomavirus 6 and 16 in Fission Yeast *Schizosaccharomyces pombo*", *Programme & Abstract Book, 13th Intl. Papillomavirus Conf.*, Amsterdam, p. 154.

Sasagawa et al. (1995) "Synthesis and Assembly of Virus-like Particles of Human Papillomaviruses Type 6 and Type 16 in Fission Yeast *Schizosaccaromyces pombe*", *Virology* 208:126-135.

Schafer et al. (2002) "DNA Binding of L1 is Required for Human Papillomavirus Morphogenesis In Vivo", *Virology* 295:172-181.

Scharf et al. (1986) "Direct Cloning and Sequence Analysis of Enzymatically Amplified Genomic Sequences," *Science* 233:1076-1078.

Schiffman et al. (1992) "Recent Progress in Defining the Epidemiology of HUman Papillomavirus Infection and Cervical Neoplasma", *Nat'l Cancer Inst.* 84:394-398.

Schiller et al. (1984) "Identification of a Second Transforming Region in Bovine Papillomavirus DNA", *PNAS USA* 81:7880-7884.

Schiller et al. (1995) "Papillomavirus-Like Particles", *Review Article Papillomavirus Report* 6:121-128.

Schiller et al. (1996) "Papillomavirus-like Particles and HPV vaccine development", *Seminars in Cancer Biology* 7:373-382.

Schiller (1999) "Papillomavirus-Like Particle Vaccines for Cervical Cancer", *Molecular Medicine Today* 5:209-215.

Schneider et al. (1991) "Rhesus Papillomavirus Type 1 Cooperates with Activated *ras* in Transforming Primary Epithelial Rat Cells Independent of Dexamethasone", *J. of Virol.* 65:3354-3358.

Schubert et al. (1985) "Expression of a cDNA Encoding a Functional 241-Kilodalton Vesicular Stomatitis Virus RNA Polymerase", *PNAS USA* 82:7984-7988.

Schwab et al. (1992) "Caveats for the Use of Surface-Adsorbed Protein Antigen to Test the Specificity of Antibodies", *Journal of Immunological Methods* 147:125-134.

Seedorf et al. (1985) "Human Papillomavirus Type 16 DNA Sequence", *Virology* 145:181-185.

Selinka et al. (2004) "Epitope Mapping of HPV-Neutralizing Antibodies Involved in Binding and Post-binding Neutralization: Implication of Cell-attachment of Neutralization" (Abstract) in The 2004 Molecular Biology of DNA Tumor Viruses Conference. Session III, p. 39.

Shade et al. (1986) "Nucleotide Sequence and Genome Organization of Human Parvovirus B19 Isolated from the Serum of a Child During Aplastic Crisis", *J. of Virol.* 58:921-936.

Shaw et al. (1986) "A conserved AU Sequence from the 3' Untranslated Region of GM-CSF mRNA Mediates Selective mRNA Degradation", *Cell* 46:659-667.

Shields et al. (1991) "An Appraisal of Polystyrene-(ELISA) and Nitrocellulose-Based (ELIFA) Enzyme Immunoassay Systems Using Monoclonal Antibodies Reactive Toward Antigenically Distinct Forms of Human C-Reactive Protein", *Journal of Immunological Methods* 141:253-261.

Shope (1936) "Immunization of Rabbits to Infectious Papillomatosis", *J. Exp. Med.* 65:219-238.

Silins et al. (1999) "Serological Evidence for Protection by Human Papillomavirus (HPV) Type 6 Infection against HPV Type 16 Cervical Carcinogenesis", *J. Gen. Virol.* 80:2931-2936.

Smith et al. (1986) "A Modified ELISA That Selectively Detects Monoclonal Antibodies Recognizing Native Antigen", *Journal of Immunological Methods* 94: 31-35.

Stanley et al. (1989) "Properties of a Non-Tumerigenic Human Cervical Keratinocyte Cell Line", *Int. J. Cancer* 43:672-676.

Stanley (1997) "Genital Human Papillomaviruses-Prospects for Vaccination" *Curr. Opinion. Infect. Dis.* 10:55-61.

Stanley (2002) "Human Papillomavirus Vaccines", *Curr. Opin. Mol. Ther.* 4:15-22.

Stanley (2003) "Progress in Prophylactic and Therapeutic Vaccines for Human Papillomavirus" *Infection. Expert Rev. Vaccines* 2:381-389.

Stauffer et al. (1998) "Infectious Human Papillomavirus Type 18 Pseudovirions", *J. Mol. Biol.* 283:529-536.

Steele et al. (1990) "Humoral Assays of Human Sera to Disrupted and Nondisrupted Epitopes of Human Papillomavirus Type 1", Virology 174:388-398.
Steele et al. (2002) "Detection of CD4$^+$ and CD8$^+$-T-Cell Responses to Human Papillomavirus Type 1 Antigens Expressed at Various Stages of the Virus Life Cycle by Using an Enzyme-Linked Immunospot Assay of Gamma Interferon Release", J. of Virol. 76:6027-6036.
Steinberg et al. (1996) "A Possible Role for Human Papillomaviruses in Head and Neck Cancer", Cancer and Metastasis Reviews 15:91-112.
Sterling et al. (1990) "Production of Human Papillomavirus Type 16 Virions in a Keratinocyte Cell Line", J. of Virol. 64:6305-6307.
Sterling et al. (1990) "Immunoelectron Microscopical Localization of Human Papillomavirus Type 16 L1 and E4 Proteins in Cervical Kertinocytes Cultured in Vivo", J. Invest. Dermatol. 100:154-158.
Stevens et al. (1987) "Yeast-Recombinant Hepatitis B Vaccine", JAMA 257:2612-2616.
Steven et al. (1997) "The Making and Breaking of Symmetry in Virus Capsid Assembly: Glimpses of Capsid Biology from Cryoelectron Microscopy", FASEB J. 11:733-742.
Stites et al. (1980) "Clinical Laboratory Methods of Detecting Cellular Immune Function", Basic and Clinical Immunol. 3:382-397.
Stoler et al. (1990) "Infectious Cycle of Human Papillomavirus Type 11 in Human Foreskin Xenografts in Nude Mice", J. of Virol. 64:3310-3318.
Storch (2001) "Diagnostic Virology", Fields Virology, 4th ed. Lippincott, Williams & Wilkins, pub. p. 493, 510.
Storey et al. (1992) "Lack of Immortalizing Activity of a Human Papillomavirus Type 16 Variant DNA with a Mutation in the Ex Gene Isolated from Normal Human Cervical Keratinocytes", Oncogene 7:459-465.
Stoscheck (1990) "Quantitation of Protein in Methods", Enzymology 182:50-68.
Stratagene (1993) Product Catalog, pp. 120-123.
Strike et al. (1989) "Expression in Escherichia coli of Seven DNA Fragments Comprising the Complete L1 and L2 Open Reading Frames of Human Papillomavirus Type 6b and the Localization of the 'Common Antigen' Region", J. Gen. Virol. 70:543-555.
Summers et al. (1987) "A Manual of Methods for Baculovirus Vectors and Insect Cell Culture Procedures", Texas Agricultural Experiment Station Bulletin 1555:5-56.
Sundberg (1987) "Papillomavirus Infections in Animals", in Papillomaviruses and Human Disease (Syrjänen et al. eds.) Spriner Verlag pp. 40-103.
Suzich et al. (1995) "Systemic Immunization With Papillomavirus L1 Protein Completely Prevents the Development of Viral Mucosal Papillomas", PNAS USA 92:11553-11557.
Syrjanen et al. (1987) "Papillomavirus Infection and Cancer" in Papillomaviruses and Human Disease, Springer Verlag p. 468-491.
Taichman et al. (1983) The Role of Keratinocyte Differentiation in the Expression of Epitheliotropic Viruses. The Journal of Investigative Dermatology 81:137s-140s.
Taichman et al. (1984) The Search for a Culture System for Papillomavirus, The Journal of Investigative Dermatology 83:2S-6S.
Tomita et al. (1987) "Expression of Human Papillomavirus Types 6b and 16 L1 Open Reading Frames in Escherichia coli: Detection of a 56,000-Dalton Polypeptide Containing Genus-Specific (Common) Antigens", J. of Virol. 61: 2389-2394.
Touze et al. (1996) "Production of Human Papillomavirus Type 45 Virus-Like Particles in Insect Cells Using Recombinant Baculovirus", FEMS Microbiology Letters 141:111-116.
Touze et al. (1998) "In Vitro Gene Transfer Using Human Papillomavirus-Like Particles", Nucleic Acids Res. 26:1317-1323.
Touze et al. (1998) "The L1 Major Capsid Protein of Human Papillomavirus Type 16 Variants Affects Yield of Virus-Like Particles Produced in an Insect Cell Expression System", J. Clin. Microbiol. 36:2046-2051.
Touze et al. (1998) "Production of Recombinant Virus-like Particles from Human Papillomavirus Types 6 and 11, and Study of Serological Reactivities between HPV 6, 11, 16 and 45 by ELISA: Implications for Papillomavirus Prevention and Detection", FEMS Microbiol. Lett. 160:111-118.
Trus et al. (1997) "Novel Structural Features of Bovine Papillomavirus Capsid Revealed by a Three-Dimensional Reconstruction to 9 Å Resolution", Nature Struct. Biol. 4: 413.
Tsujimoto et al. (1988) "Isolation and Characterization of Simian Immunodeficiency Virus from Mandrills in Africa and Its Relationship to Other Human and Simian Immunodeficiency Viruses", J. of Virol. 62:4044-4050.
Unckell et al. (1997) "Generation and Neutralization of Pseudovirions of Human Papillomavirus Type 33", J. of Virol. 71:2934-2939.
Urukawa et al. (1989) "Synthesis of Immunogenic, but Non-Infectious, Poliovirus Particles in Insect Cells by Baculovirus Expression Vector", J. Gen. Virol. 70:1453-1463.
Valenzuela et al. (1982) "Synthesis and Assembly of Hepatitis B Virus Surface Antigen Particles in Yeast", Nature 298:347-350.
Van Regenmortel (1992) "The Conformational Specificity of Viral Epitopes", FEMS Microbiol. Lett. 100:483-488.
Viac et al. (1990) "Incidence of Antibodies to Human Papillomavirus Type 1 in Patients with Cutaneous and Mucosal Papillomas", J. Med. Virol. 32:18-21.
Voller et al. (1976) "Enzyme Immunoassays in Diagnostic Medicine", Bull. World Health Org. 53:55-65.
Volpers et al. (1994) "Assembly of the Major and Minor Capsid Protein of Human Papillomavirus Type 33 into Virus-like Particles and Tubular Structures in Insect Cells", Virology 200:504-512.
Volpers et al. (1995) "Binding and Internationalization of Human Papillomavirus Type 33 Virus-Like Particles by Eukaryotic Cells", J. of Virol. 69:3258-3264.
Vonka et al. (1999) "Prospective Study on Cervical Neoplasia IV. Presence of HPV Antibodies", Int. J. Cancer 80:365-368.
Wang et al. (1991) "Baculovirus Vectors for Multiple Gene Expression and for Occluded Virus Production", Gene 100:131-137.
Wang et al. (1996) "Cervical Mucus Antibodies against Human Papillomavirus Type 16, 18, and 33 Capsids in Relation to Presence of Viral DNA", J. Clin. Microbiol. 34:3056-3062.
Wang et al. (1997) "A Monoclonal Antibody Against Intact Human Papillomavirus Type 16 Capsids Blocks the Serological Reactivity of Most Human Sera", J. Gen. Virol. 78:2209-2215.
Wang et al. (1997) "Human Papillomavirus Antibody Responses among Patients with Incident Cervical Carcinoma", J. Med. Virol. 52:436-440.
Wang et al. (2003) "Mapping of Human Serum-Reactive Epitopes in Virus-Like Particles of Human Papillomavirus Types 16 and 11", Virology 311:213-221.
Wang et al. (2005) "Heparin-based ELISA Reduces Background Reactivity in Virus-like Particle-based Papillomavirus Serology", J. Gen. Virol. 86:65-73.
Watson et al. (1983) Eds, "Recombinant DNA—A Short Course", W.J. Freeman and Company (New York) publishers, p. 236.
Watson et al. (1992) "A Hepatitis B Virus Vaccine is Produced in Yeast by Expression of a Viral Surface Antigen", Recombinant DNA. Scientific American Books, 2nd ed. Chap. 23, p. 458-459.
White et al. (1998) "In Vitro Infection and Type-Restricted Antibody-Mediated Neutralization of Authentic Human Papillomavirus Type 16", J. of Virol. 72:959-964.
White et al. (1999) "Characterization of a Major Neutralizing Epitope on Human Papillomavirus Type 16 L1", J. of Virol. 73:4882-4889.
Wideroff et al. (1995) "Evaluation of Seroreactivity to Human Papillomavirus Type 16 Virus-like Particles in an Incident Case-Control Study of Cervical Neoplasia", J. Infect. Dis. 172:1425-1430.
Wikstrom et al. (1995) "Identification of Human Papillomavirus Seroconversions", J. Gen. Virol. 76:529-539.
Wilbur et al. (1988) "Detection of Infection by Human Papillomavirus in Genital Condylomata", Am J. Clin. Pathol. 89: 505-510.
Williamson et al. (1991) "The Use of the Polymerase Chain Reaction for the Detection of Human Papillomavirus Type 13", J. Virol. Methods 31:57-66.

Xi et al. (1991) "Baculovirus Expression of the Human Papillomavirus Type 16 Capsid Proteins: Detection of L1-L2 Protein Complexes", *J. Gen. Virol.* 72:2981-2988.

Yamada et al. (1995) "Human Papillomavirus Type 16 Variant Lineages in United States Populations Characterized by Nucleotide Sequence Analysis of the E6, L2, and I1 Coding Segments", *J. of Virol.* 69:7743-7753.

Yaegashi et al. (1991) "Characterization of Murine Polyclonal Antisera and Monoclonal Antibodies Generated Against Intact and Denatured Human Papillomavirus Type I Virions", *J. of Virol.* 65:1578-1583.

Yeager et al. (2000) "Neutralization of Human Papillomavirus (HPV) Pseudovirions: A Novel and Efficient Approach to Detect and Characterize HPV Neutralizing Antibodies", *Virology* 278:570-577.

Yee et al. (1985) "Presence and Expression of Human Papillomavirus Sequences in Human Cervical Carcinoma Cell Lines", *Am. J. Pathology* 119:361-366.

Yong Kang et al. (1987) "Secretion of Particles of Hepatitis B Surface Antigen from Insect Cells Using a Baculovirus Vector", *J. Gen. Virol.* 68:2607-2613.

Yoshiike (1968) "Studies on DNA from Low-Density Particles of SV40. I. Heterogeneous Defective Virions Produced by Successive Undiluted Passages", *Virology* 34:391-401.

Yuan et al. (2000) "Bacterially-Expressed GST-L1 Fusion Protein: Simplified Purification, Maintenance of Native Conformation, and Efficacy as a Prophylactic Papillomavirus Vaccine", *18th Int'l Papillomavirus Conference*, Barcelona, Spain, Jul. 2000 (Abstract).

Yuan, et al. (2001) "Immunization with a Pentameric L1 Fusion Protein Protects against Papillomavirus Infection", *J. of Virol.* 75:7848-7853.

Zhang et al. (1998) "Expression of Human Papillomavirus Type 16 L1 Protein in *Escherichia coli*: Denaturation, Renaturation, and Self-Assembly of Virus-like Particles in Vitro", *Virology* 242:423-431.

Zhou et al. (1990) "Increased Antibody Responses to Human Papillomavirus Type 16 L1 Protein Expressed by Recombinant Vaccinia Virus Lacking Serine Protease Inhibitor Genes", *J. Gen. Virol.* 71:2185-2190.

Zhou et al. (1991) "Expression of Vaccinia Recombinant HPV 16 L1 and L2 ORF Proteins in Epithelial Cells Is Sufficient for Assembly of HPV Virion-like Particles", *Virology* 185:251-257.

Zhou et al. (1991) "Human Papillomavirus Type 16 Virions Produced By A Recombinant Vaccinia Virus", 1991 Papillomavirus Workshop, Seattle, Jul. 20-26, 1991 (Abstract with excerpts of the Abstract Book from the 1991 PV Workshop includes Program schedule, Author Index).

Zhou et al. (1991) "Identification of the Nuclear Localization Signal of Human Papillomavirus Type 16 L1 Protein", *Virology* 185:626-632.

Zhou et al. (1991) "The Induction of Cytotoxic T-Lymphocyte Precursor Cells by Recombinant Vaccinia Virus Expressing Human Papillomavirus Type 16 L1", *Virology* 181:203-210.

Zhou et al. (1992) "Definition of Linear Antigenic Regions of the HPV16 L1 Capsid Protein Using Synthetic Virion-Like Particles", *Virology* 189:592-599.

Zhou et al. (1993) "Synthesis and Assembly of Infectious Bovine Papillomavirus Particles In Vitro", *J. Gen. Virol.* 74:763:768.

Zhou et al. (1999) "Papillomavirus Capsid Protein Expression Levels Depends on the Match between Codon Usage and tRNA Availability", *J. of Virol.* 71:2988-2995.

Zur Hausen (1991) "Viruses in Human Cancers", *Science* 254:1167-1173.

\* cited by examiner

SELF-ASSEMBLING RECOMBINANT PAPILLOMAVIRUS CAPSID PROTEINS

RELATED APPLICATIONS

This application is a continuation and claims the benefit of priority of U.S. patent application Ser. No. 09/832,065 filed Apr. 9, 2001 now abandoned, which is a continuation and claims the benefit of priority of U.S. patent application Ser. No. 09/316,487 filed May 21, 1999 now abandoned, which is a continuation and claims the benefit of priority of 08/484,503, filed Jun. 7, 1995, now U.S. Pat. No. 5,985,610, which is a continuation and claims the benefit of priority of U.S. patent application Ser. No. 08/032,869, filed Mar. 16, 1993, now U.S. Pat. No. 5,437,951, which is a continuation-in-part and claims the benefit of priority of U.S. patent application Ser. No. 07/941,371, filed Sep. 3, 1992. These applications are hereby incorporated by reference as if fully set forth herein. The invention relates to recombinant viral proteins. It relates particularly to recombinant viral proteins that are suitable for use in the diagnosis, prophylaxis and therapy of viral infections.

DESCRIPTION OF THE RELATED ART

Papillomaviruses infect the epithelia of a wide variety of species of animals, including humans, generally inducing benign epithelial and fibro-epithelial tumors, or warts, at the site of infection. Each species of vertebrate is infected by a distinct group of papillomaviruses, each papillomavirus group comprising several papillomavirus types. For example, more than 60 different human papillomavirus (HPV) genotypes have been isolated. Papillomaviruses are highly species specific infective agents; for example, a bovine papillomavirus cannot induce papillomas in a heterologous species, such as humans. Papillomavirus types ALSO appear to be highly specific as immunogens in that a neutralizing immunity to infection against one papillomavirus type does not usually confer immunity against another type, even when the types infect an homologous species.

In humans, genital warts, which are caused by human papillomaviruses, represent a sexually transmitted disease. Genital warts are very common, and subclinical, or inapparent HPV infection is even more common than clinical infection. Some benign lesions in humans, particularly those arising from certain papillomavirus types, undergo malignant progression. For that reason, infection by one of the malignancy associated papilloma virus types is considered one of the most significant risk factors in the development of cervical cancer, the second most common cancer of women worldwide (zur Hausen, H., 1991; Schiffman, M. 1992). Several different HPV genotypes have been found in cervical cancer, with HPV16 being the most common type that is isolated from 50% of cervical cancers.

Immunological studies demonstrating the production of neutralizing antibodies to papillomavirus antigens indicate that papillomavirus infections and malignancies associated with these infections in vertebrate animals could be prevented through immunization; however the development of effective papillomavirus vaccines has been impeded by a number of difficulties.

First, it has not been possible to generate in vitro the large stocks of infectious virus required to determine the structural and immunogenic features of papillomavirus that are fundamental to the development of effective vaccines. Cultured cells express papillomavirus oncoproteins and other non structural proteins and these have been extensively studied in vitro; but expression of the structural viral proteins, L1 and L2 (and the subsequent assembly of infectious virus) occurs only in terminally differentiated layers of infected epithelial tissues. Therefore, the characterization of viral genes, proteins, and structure has necessarily been assembled from studies of virus harvested from papillomas. In particular, papillomavirus structure and related immunity have been carried out in the bovine papillomavirus system because large amounts of infectious virus particles can be isolated from bovine papillomavirus (BPV) warts.

The information derived from studies of papillomavirus structure to date indicates that all papillomaviruses are non enveloped 50 60 nm icosahedral structures (Crawford, L., et al., 1963) which are comprised of conserved L1 major capsid protein and less well conserved L2 minor capsid protein (Baker, C., 1987). There is no sequence relationship between the two proteins. The function and location of L2 in the capsid is unclear; however immunologic data suggests that most of L2 is internal to L1.

Recently, high resolution cryoelectron microscopic analysis of BPV1 and HPV1 virions has determined that the two viruses have a very similar structure, with 72 pentameric capsomers, each capsomer presumably composed of five L1 molecules, forming a virion shell with T=7 symmetry (Baker, T., 1991). The location of the minor L2 capsid protein in the virion has not been determined, and it is not certain whether L2 or other viral proteins are needed for capsid assembly. Superficially, papillomavirus structure resembles that of the polyoma 45 nm virion, which has the same symmetry and capsomere number (Liddington, R., et al., 1991); however, the systems of intracapsomer contact for polyomavirus and papillomavirus species are different, and the major and minor capsid proteins of polyomavirus are not genetically related to L1 and L2.

Bovine papillomavirus studies are facilitated by a quantitative focal transformation infectivity assay developed for BPV that is not available for HPV (Dvoretzky, I., et al., 1980), and an understanding of immunity to papillomavirus has therefore also been derived from the bovine papillomavirus system. Limited studies using intact bovine papillomavirus demonstrated that the non-cutaneous inoculation of infectious or formalin-inactivated BPV virus was effective as a vaccine to prevent experimental BPV infection in calves (Olson, C., et al., 1960; Jarrett, W., et al., 1990). Unfortunately, BPV virions cannot be used to develop vaccines against papillomavirus which infects other species, or even vaccines against other bovine types, because of the great specificity of these viruses, as well as concern for the oncogenic potential of intact viral particles.

A significant conclusion of studies of papillomavirus immunity is that the ability of antibodies to neutralize papilloma virus appears to be related to their ability to react with type-specific, conformationally dependent epitopes on the virion surface. For example, rabbit antisera raised against infectious BPV1 virions inhibits focal transformation of C127 cells (Doretzky, I., et al., 1980), as well as the transformation of fetal bovine skin grafts; whereas antisera raised against denatured virions does not (Ghim, S., et al., 1991).

In contrast, neutralizing sera generated against bacterially derived BPV L1 and L2 (Pilacinski, W. et al., 1984; Jin, X., et al., 1989) and against in vitro synthesized cottontail rabbit papillomavirus (CRPV) L1 and L2 (Christensen, N., et al., 1991; Lin, Y-L, et al., 1992), neither of which has the structural features of native virions, had low titers, and the use of recombinant HPV L1 fusion peptides expressed in *E. coli* to detect cellular immune reactivity has had only limited success (Höpfl, R. et al., 1991). The results in the BPV system are consistent with those of the HPV system, in which monoclonal antibodies that neutralized HPV11 infection in a mouse xenograft assay recognized native, but not denatured, HPV11 virions (Christensen, N., et al., 1990).

There have been isolated attempts to produce papillomavirus capsids in vitro. Zhou, J. et al. (1991) and (1992) produced virus-like particles by cloning HPV L1 and L2 genes, and HPV L1 and L2 genes in combination with HPV E3/E4 genes into a vaccinia virus vector and infecting CV-1 mammalian cells with the recombinant vaccinia virus. These studies were interpreted by Zhou to establish that expression of HPV16 L1 and L2 proteins in epithelial cells is necessary and sufficient to allow assembly of virion type particles. Cells infected with doubly recombinant vaccinia virus which expressed L1 and L2 proteins showed small (40 μm) virus-like particles in the nucleus that appeared to be incompletely assembled arrays of HPV capsomers. Expressing L1 protein alone, or L2 protein alone, was expressed did not produce virus-like particles; cells doubly infected with singly recombinant vaccinia virus containing L1 and L2 genes also did not produce particles. No neutralizing activity was reported.

Ghim et al., (1992) reported that when L1 from HPV1, a non-genital virus type associated mainly with warts on the hands and feet, was expressed in mammalian cells, the L1 protein contained conformational epitopes found on intact virions. Ghim did not determine if particles were produced, nor was it evaluated if the L1 protein might induce neutralizing antibodies. Even more recently, Hagansee, et al. (1993) reported that when L1 from HPV1 was expressed in human cells, it self-assembled into virus-like particles. No neutralizing antibody studies were performed.

Studies in other virus systems, for example, parvovirus, indicate that capsid assembly alone may not confer immunogenicity. Parvovirus VP2, by itself, was able to self-assemble when expressed in insect cells, but only particles containing both VP1 and VP2 were able to induce neutralizing antibodies (Kajigaya, S., et al., 1991).

It would be advantageous to develop methods for producing renewable papillomavirus reagents of any selected species and type in cell culture. It would also be beneficial to produce such papillomavirus reagents having the immunity conferring properties of the conformed native virus particles that could be used as a subunit vaccine.

It is therefore the object of the invention to provide these recombinant conformed papillomavirus proteins, as well as methods for their production and use.

SUMMARY OF THE INVENTION

The invention is directed to the diagnosis and prevention of papillomavirus infections and their benign and malignant sequelae by providing recombinant papillomavirus capsid proteins that self assemble to form capsomer structures comprising conformational epitopes that are highly specific and highly immunogenic. Therefore, according to the invention there is provided a genetic construct, comprising a papillomavirus L1 conformational coding sequence, inserted into a baculovirus transfer vector, and operatively expressed by a promoter of that vector. The papillomavirus L1 conformational coding sequence can be isolated from a bovine, monkey, or human gene. In a preferred embodiment, the papillomavirus L1 conformational coding sequence is isolated from a wild type HPV16 gene. In a particularly preferred embodiment, the papillomavirus L1 conformational coding sequence is SEQ ID NO: 3 (nucleotide) and SEQ ID NO: 4 (amino acid). The genetic construct can further comprise a papillomavirus L2 coding sequence.

According to another aspect of the invention there is provided a non-mammalian eukaryotic host cell transformed by the genetic constructs of the invention.

According to yet another aspect of the invention there is provided a method for producing a recombinant papillomavirus capsid protein, assembled into a capsomer structure or a portion thereof, comprising the steps of (1) cloning a papillomavirus gene that codes for an L1 conformational capsid protein into a transfer vector wherein the open reading frame of said gene is under the control of the promoter of said vector; (2) transferring the recombinant vector into a host cell, wherein the cloned papillomavirus gene expresses the papillomavirus capsid protein; and (3) isolating capsomer structures, comprising the papillomavirus capsid protein, from the host cell. In a preferred embodiment, the cloned papillomavirus gene consists essentially of the conformational L1 coding sequence, and the expressed protein assembles into capsomer structures consisting essentially of L1 capsid protein. In another preferred embodiment, the cloning step of the method further comprises the cloning of a papillomavirus gene coding for L2 capsid protein, whereby said L1 and L2 proteins are coexpressed in the host cell, and wherein the isolated capsomer structures comprise L1 and L2 capsid proteins; provided that said transfer vector is not a vaccinia virus when said host cell is a mammalian cell. The conformational L1 coding sequence can be cloned from a bovine, monkey, or human papillomavirus. According to a preferred embodiment, the conformational L1 coding sequence is cloned from a wild type HPV16 papillomavirus. In a particularly preferred embodiment, the conformational L1 coding sequence is SEQ ID NO: 3 (nucleotide) and SEQ ID NO: 4 (amino acid). Also in a preferred embodiment, the host cell into which the genetic construct is transfected is an insect cell. Also preferred are embodiments wherein the transfer vector is a baculovirus based transfer vector, and the papillomavirus gene is under the control of a promoter that is active in insect cells. Accordingly in this embodiment, the recombinant baculovirus DNA is transfected into Sf-9 insect cells, preferably co-transfected with wild type baculovirus DNA into Sf 9 insect cells.

In an alternative embodiment of the method of the invention, the transfer vector is a yeast transfer vector, and the recombinant vector is transfected into yeast cells.

According to yet another aspect of the invention there is provided a virus capsomer structure, or a portion thereof, consisting essentially of papillomavirus L1 capsid protein, produced by the method the invention. Alternatively, the virus capsomer structure can consist essentially of papillomavirus L1 and L2 capsid proteins, produced by the method of the invention. In a particularly preferred embodiment, the virus capsomer structure comprises papillomavirus L1 capsid protein that is the expression product of an HPV16 L1 DNA cloned from a wild type virus.

The virus capsids or capsomer structures of the invention, or portions or fragments thereof, can consist essentially of papillomavirus L1 capsid protein. Alternatively, these capsids or capsomer structures or their fragments can consist essentially of wild type HPV16 papillomavirus L1 capsid protein.

The virus capsid structures according to any of the methods of the invention comprise capsid proteins having immunogenic conformational epitopes capable of inducing neutralizing antibodies against native papillomavirus. The capsid proteins can be bovine, monkey or human papillomavirus L1 proteins. In a preferred embodiment, the papillomavirus L1 capsid protein is the expression product of a wild type HPV16 L1 gene. In a particularly preferred embodiment, the HPV16 L1 gene comprises the sequence of SEQ ID NO: 3 (nucleotide) and SEQ ID NO: 4 (amino acid).

According to yet another aspect of the invention there is provided a unit dose of a vaccine, comprising a peptide having conformational epitopes of a papillomavirus L1 capsid protein, or L1 protein and L2 capsid proteins, in an effective immunogenic concentration sufficient to induce a papillomavirus neutralizing antibody titer of at least about $10^5$ when administered according to an immunizing dosage schedule. In a preferred embodiment, the vaccine comprises an L1 capsid protein which is an HPV16 capsid protein. In a particularly preferred embodiment, the vaccine comprises an L1 capsid protein that is a wild type HPV16 L1 protein.

Use of the L1 open reading frame (ORF) from a wild type HPV16 papillomavirus genome, according to the methods of the invention, particularly facilitates the production of preparative amounts of virus-like particles on a scale suitable for vaccine use.

According to yet another aspect of the invention, there is provided a method of preventing or treating papillomavirus infection in a vertebrate, comprising the administration of a papillomavirus capsomer structure or a fragment thereof according to the invention to a vertebrate, according to an immunity producing regimen. In a preferred embodiment, the papillomavirus capsomer structure comprises wild type HPV16 L1 capsid protein.

The invention further provides a method of preventing or treating papillomavirus infection in a vertebrate, comprising the administration of the papillomavirus capsomer structure of the invention, or a vaccine product comprising the capsomer structure to a vertebrate, according to an immunity producing regimen. In a preferred embodiment, the papillomavirus vaccine comprises wild type HPV16 L1 capsid protein.

Also within the scope of the invention is a method for immunizing a vertebrate against papillomavirus infection, comprising administering to the vertebrate a recombinant genetic construct of the invention comprising a conformational papillomavirus L1 coding sequence, and allowing said coding sequence to be expressed in the cells or tissues of said vertebrate, whereby an effective, neutralizing, immune response to papillomavirus is induced. In a preferred embodiment, the conformational papillomavirus L1 coding sequence is derived from human papillomavirus HPV16. In a particularly preferred embodiment, the human papillomavirus HPV16 is a wild type papillomavirus.

According to yet another aspect of the invention, there is provided a method of detecting humoral immunity to papillomavirus infection in a vertebrate comprising the steps of: (a) providing an effective antibody detecting amount of a papillomavirus capsid peptide having at least one conformational epitope of a papillomavirus capsomer structure; (b) contacting the peptide of step (a) with a sample of bodily fluid from a vertebrate to be examined for papillomavirus infection, and allowing papillomavirus antibodies contained in said sample to bind thereto, forming antigen-antibody complexes; (c) separating said complexes from unbound substances; (d) contacting the complexes of step (c) with a detectably labelled immunoglobulin binding agent; and (e) detecting anti papillomavirus antibodies in said sample by means of the labelled immunoglobulin binding agent that binds to said complexes. In a preferred embodiment of this aspect of the invention, the peptide consists essentially of papillomavirus L1 capsid protein. According to an alternative embodiment, the peptide consists essentially of the expression product of a human papillomavirus HPV16. In a particularly preferred embodiment, the peptide consists essentially of the expression product of a wild type human papillomavirus HPV16 gene, for example, the peptide can consist essentially of the expression product of SEQ ID NO: 3 (nucleotide) and SEQ ID NO: 4 (amino acid).

According to yet another aspect of the invention, there is provided a method of detecting papillomavirus in a specimen from an animal suspected of being infected with said virus, comprising contacting the specimen with antibodies having a specificity to one or more conformational epitopes of the capsid of said papillomavirus, wherein the antibodies have a detectable signal producing label, or are attached to a detectably labelled reagent; allowing the antibodies to bind to the papillomavirus; and determining the presence of papillomavirus present in the specimen by means of the detectable label.

According to yet another aspect of the invention, there is provided a method of determining a cellular immune response to papillomavirus in an animal suspected of being infected with the virus, comprising contacting immunocompetent cells of said animal with a recombinant wild type papillomavirus L1 capsid protein, or combined recombinant L1 and L2 capsid proteins according to the invention; and assessing cellular immunity to papillomavirus by means of the proliferative response of said cells to the capsid protein. In a preferred embodiment of this aspect of the invention, the recombinant papillomavirus protein is introduced into the skin of the animal.

According to yet another aspect of the invention there is provided a papillomavirus infection diagnostic kit, comprising capsomer structures consisting essentially of papillomavirus L1 capsid protein, or capsomer structures comprising papillomavirus L1 protein and L2 capsid proteins, or antibodies to either of these capsomer structures, singly or in combination, together with materials for carrying out an assay for humoral or cellular immunity against papillomavirus, in a unit package container.

DETAILED DESCRIPTION OF THE PREFERRED EMBODIMENT

Figure 1:
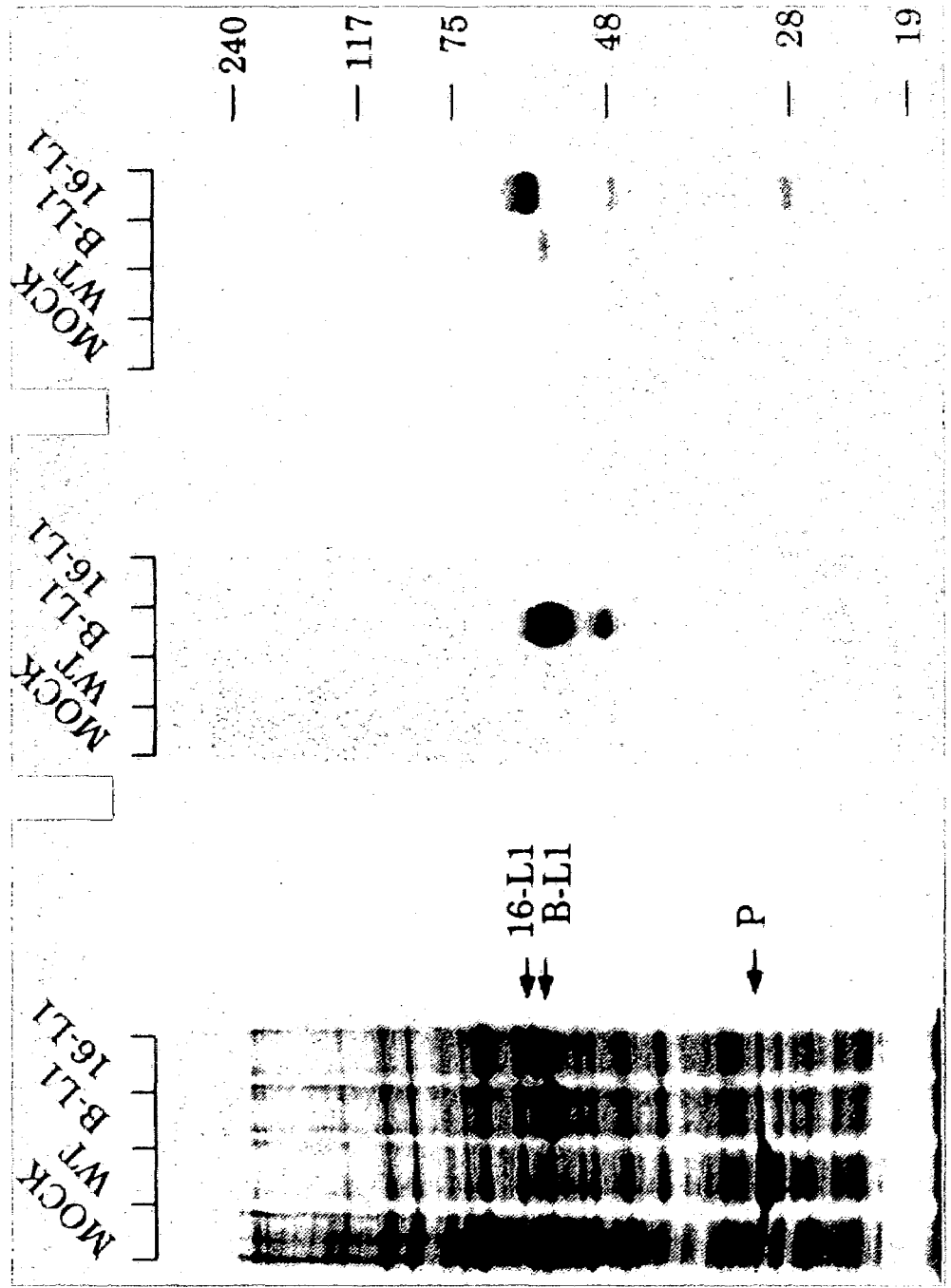
FIG. 1 shows the expression of BPV L1 and HPV16 L1 by means of recombinant virus as demonstrated by SDS PAGE analysis of lysates from infected insect cells.

We have discovered that the gene coding for the L1 major capsid protein of BPV or HPV16, following introduction into host cells by means of an appropriate transfer vector, can express L1 at high levels, and that the recombinant L1 has the intrinsic capacity to self assemble into empty capsomer structures that closely resemble those of an intact virion. Further, the self assembled recombinant L1 capsid protein of the invention, in contrast to L1 protein extracted from recombinant bacteria, or denatured virions, has the efficacy of intact papillomavirus particles in the ability to induce high levels of neutralizing antiserum that can protect against papillomavirus infection. The high level of immunogenicity of the capsid proteins of the invention implies strong antibody binding properties that make them sensitive agents in serological screening tests to detect and measure antibodies to conformational virion epitopes. Their immunogenicity also indicates that the capsid proteins of the invention can also be used as highly effective vaccines or immunogens to elicit neutralizing antibodies to protect a host animal against infection by papillomavirus. These observations were recently published in Kirnbauer, et al., (1992), and formed the basis of U.S. application Ser. No. 07/941,371.

We have now discovered that the capsid protein L1 expressed by wild type HPV16 genomes isolated from benign papillomavirus lesions, when expressed in the baculovirus system described, will self-assemble with an efficiency heretofore unknown and comparable to that of bovine papillomavirus L1 capsid protein.

The HPV16 L1 Gene Sequences

The source of HPV16 L1 DNA, as disclosed in published studies, for example, by Zhou, et al. (1991) was the prototype clone, GenBank Accession No. K02718, that had been isolated from a cervical carcinoma (Seedorf, et al., 1985). We have found that L1 from wild type HPV16 genome, which differs from the prototype genome by a single point mutation, will self-assemble into virus-like particles with an efficiency similar to that seen with BPV L1 or BPV L1/L2. Compared with the self-assembly seen when L1 from the prototype HPV genome is used with L2, L1 from a wild-type genome self-assembles at least 100 times more efficiently.

To provide genetic insight into the self-assembly efficiency of different HPV16 L1 expression products, the open reading frames from HPV16 L1 genes isolated from both benign lesions and lesions associated with dysplasia or carcinoma were sequenced.

The analysis detected two errors in the published sequence of the published L1 sequence of the prototype strain, as follows:

(1) there should be an insertion of three nucleotides (ATC) between nt 6901 and 6902, which results in the insertion of a serine in the L1 protein; and (2) there should be a deletion in the published prototype sequence of three nucleotides (GAT), consisting of nt 6951–6953, which deletes an aspartate from the L1 protein sequence. The corrected nucleotide sequence of the prototype HPV16 L1 genome, consisting of nt 5637–7154, is that of SEQ ID NO: 1, listed herein.

The numbering of the nucleotide bases in SEQ ID NO: 1 and SEQ ID NO: 3 is indexed to 1, and the numbering of nucleotide bases of the published HPV sequence, that is from nt 5637–7154, corresponds to those of the sequence listing from 1–1517. The sites referred to in the original sequence can be thus readily identified by one skilled in the art.

Three other HPV16 L1 genomes, clone 16PAT; and clones 114/16/2 and 114/16/11, were sequenced and those sequences compared to that of the corrected prototype.

Clone 16PAT, kindly provided by Dennis McCance at the University of Rochester School of Medicine, and cloned from a dysplastic (pre-malignant) lesion of the cervix, expresses an L1 that does not self-assemble efficiently.

Clones 114/16/2 and 114/16/11, kindly provided by Matthias Dürst of the German Cancer Research Center in Heidelburg, were both cloned from non-malignant lesions, and both expressed L1 protein that self-assembled efficiently.

Comparison of Genetic Characteristics of HPV16 L1 Associated with Dysplasia, Malignant Progression and Benign Lesions Clone 16PAT, isolated from papillomavirus infected dysplastic lesions and the prototype HPV16, isolated from malignant cervical carcinoma, both encode Histidine at nt 6240–6242, while clones 2 and 11, isolated from benign papillomavirus infected lesions (like isolates of many other papillomavirus) encode Aspartate at this site.

It appears that this single amino acid difference between the prototype, malignancy-associated HPV16 species, and the HPV16 species from benign lesions accounts for the difference in self-assembly efficiency. It is likely that among closely related HPV types, Aspartate at this locus may be necessary for efficient self-assembly, and that the substitution of Histidine for Aspartate impairs this ability in the capsid protein. The impairment in capsid assembly in malignancy-associated viruses, associated with loss of the conformational epitopes required for the production of neutralizing antibodies, may also be linked to a lowered immunogenicity which would allow the papillomavirus to escape immune control.

Accordingly, HPV16 L1 genes that express capsid protein that self-assembles efficiently can be obtained by (1) isolation of the wild type HPV16 L1 open reading frame from benign lesions of papillomavirus infection; or (2) carrying out a site specific mutation in the prototype sequence at nt 6240–6242 to encode Aspartate.

Recombinant Capsid Protein

The method of the invention provides a means of preparing recombinant capsid particles for any papillomavirus. Particles consisting of either L1 or L2 capsid protein alone, or consisting of both L1 and L2 capsid proteins together can be prepared. L1/L2 capsid protein particles are more closely related to the composition of native papillomavirus virions, but L2 does not appear to be as significant as L1 in conferring immunity, probably because most of L2 is internal to L1 in the capsid structure. Although L1 can self-assemble by itself, in the absence of L2, self-assembled L1/L2 capsid protein particles are more closely related to the composition of native papillomavirus virions. Accordingly, particles comprising L1 alone are simpler, while those comprising L1/L2 may have an even more authentic structure. Both self-assembled L1 and L1/L2 particles induce high-titer neutralizing antibodies and may therefore be suitable for vaccine production. Particles comprising L1 capsid protein expressed by a wild type HPV genome, either as L1 alone or L1/L2 together, are particularly preferred.

Production of the recombinant L1, or combined L1/L2, capsid particles is carried out by cloning the L1 (or L1 and L2) gene(s) into a suitable vector and expressing the corresponding conformational coding sequences for these proteins in a eukaryotic cell transformed by the vector. It is believed that the ability to form a capsid-like structure is intimately related to the ability of the capsid protein to generate high-titer neutralizing antibody, and that in order to produce a capsid protein that is capable of self-assembling into capsid structures having conformational epitopes, substantially all of the capsid protein coding sequence must be expressed. Accordingly, substantially all of the capsid protein coding sequence is cloned. The gene is preferably expressed in a eukaryotic cell system. Insect cells are preferred host cells; however, yeast cells are also suitable as host cells if appropriate yeast expression vectors are used. Mammalian cells similarly transfected using appropriate mammalian expression vectors can also be used to produce assembled capsid protein, however, cultured mammalian cells are less advantageous because they are more likely than non-mammalian cells to harbor occult viruses which might be infectious for mammals.

According to a preferred protocol, a baculovirus system is used. The gene to be cloned, substantially all of the coding sequence for bovine papillomavirus (BPV1) or human papillomavirus (HPV16) L1 capsid protein, or human papillomavirus HPV16 L1 and L2, is inserted into a baculovirus transfer vector containing flanking baculovirus sequences to form a gene construct, and the recombinant DNA is co-transfected with wild type baculovirus DNA into Sf-9 insect cells as described in Example 1, to generate recombinant virus which, on infection, can express the inserted gene at high levels. The actual production of protein is made by infecting fresh insect cells with the recombinant baculovirus; accordingly, the L1 capsid protein and the L1 and L2 capsid proteins are expressed in insect cells that have been infected with recombinant baculovirus as described in Example 2.

In the procedure of Example 1, the complete L1 gene of BPV1 was amplified by polymerase chain reaction (PCR; Saiki, R., et al., 1987) and cloned into AcMNPV (*Autographa californica* nuclear polyhedrosis virus) based baculovirus vector (Summers, M. et al., 1987). The L1 open reading frame was put under the control of the baculovirus polyhedrin promoter. After co-transfection of the L1 clone with the wild type (wt) baculovirus DNA into Sf-9 insect cells (ATCC Accession No. CRL 1711) and plaque purification of recombinant clones, high titer recombinant virus was generated. Extracts from cells infected with wt AcMNPV or BPV1 L1 recombinant viruses (AcBPV-L1) (Example 2) were analyzed by polyacrylamide gel electrophoresis. After Coomassie blue staining, a unique protein of the predicted size, 55 kilodaltons, was detected in extracts from the cultures infected with the AcBPV1-L1 virus (FIG. 1A). The identity of this protein as BPV L1 was verified by immunoblotting (FIG. 1B), using a BPV L1 specific monoclonal antibody (Nakai, Y., et al., 1986).

To test the hypothesis that papillomavirus L1 has the ability to self-assemble into virus-like particles when over-expressed in heterologous cells, electron micrographs of thin sections from AcBPV-L1 infected cells were examined for the presence of papillomavirus-like structures. Cells infected with the BPV recombinant virus contained many circular structures of approximately 50 nm which were preferentially localized in the nucleus; these structures were absent from wild type baculovirus infected cells. These results suggested that self assembly of L1 into virus-like particles had occurred, since in vivo papillomavirus virion assembly takes place in the nucleus and the diameter of the virions has been reported as 55 nm.

Figure 2:
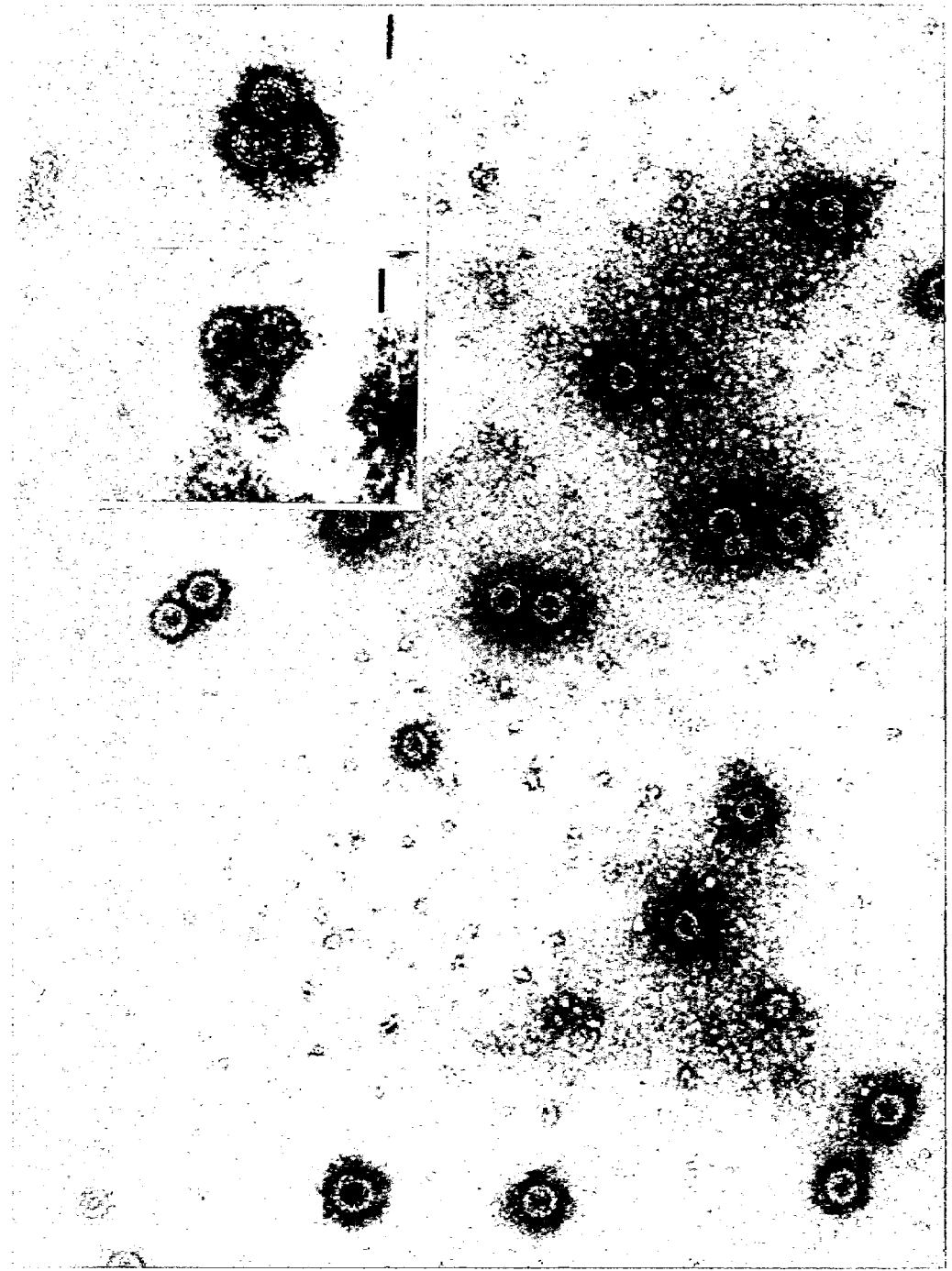
FIG. 2 shows the conformation of purified recombinant BPV L1 and HPV16 L1 capsid proteins as demonstrated by electron microscopy, compared with authentic BPV virions.

Following expression of the conformed capsid protein in the host cell, virus particles are purified from lysates of infected cells as described in Example 4. To obtain further evidence that the L1 protein had self-assembled, virus-like particles were isolated from the infected insect cells by means of gradient centrifugation (FIG. 2).

High molecular mass structures were separated from lysates of L1 recombinant or wild type infected cells by centrifugation through a 40% sucrose cushion and the pelleted material was subjected to CsCl density gradient centrifugation. Fractions were collected and tested for reactivity to the BPV L1 specific monoclonal antibody by immunoblotting.

L1 positive fractions from the gradient were adsorbed onto carbon film grids, stained with 1% uranyl acetate and examined by transmission electron microscopy. The positive fractions contained numerous circular structures that exhibited a regular array of capsomers (FIG. 2A). Consistent with previous reports of the density of empty BPV virions (Larsen, P., et al., 1987), the density of the CsCl fraction containing the peak of the virus-like particles was approximately 1.30 gm/ml. Most were approximately 50 nm in diameter, although smaller circles and partially assembled structures were also seen. The larger particles were very similar in size and subunit structure to infectious BPV virions that had been stained and photographed concurrently (FIG. 2B). These particles were not observed in preparations from mock infected or wt AcMNPV infected cells. These results indicate that BPV L1 has the intrinsic capacity to assemble into virus-like particles in the absence of L2 or other papillomavirus proteins. In addition, specific factors limited to differentiating epithelia or mammalian cells are not required for papillomavirus capsid assembly.

To determine if the ability to self-assemble in insect cells is a general feature of papillomavirus L1, we also expressed the L1 of HPV16, the HPV type most often detected in human genital cancers, via an analogous recombinant baculovirus. A protein of the expected 58 kd size was expressed at high levels in the insect cells infected with the HPV16-L1 recombinant virus (FIG. 1A) and it reacted strongly with an HPV16 L1 monoclonal antibody (which also reacted weakly with BPV L1; FIG. 1C). After CsCl gradient purification, immunoreactive fractions were examined by electron microscopy and found to contain 50 nm papillomavirus-like particles (FIG. 2C). Although somewhat fewer completely assembled particles were seen in the human system in comparison to the BPV L1 preparations, possibly due to the lower levels of expression or greater extent of HPV16 L1 degradation (FIG. 1), the results conclusively indicate that the L1 of the HPV16 and presumably the L1 proteins of other types, have the intrinsic capacity to assemble into virion-type structures. Preparations of recombinant papillomavirus capsid particles for Rhesus monkey PV have also been carried out as described in the Examples.

Recombinant Conformed Capsid Proteins as Immunogens

Subunit vaccines, based on self-assembled major capsid proteins synthesized in heterologous cells, have been proved effective in preventing infections by several pathogenic viruses, including human hepatitis B (Stevens, C., et al., 1987).

Studies demonstrating that infectious or formalin inactivated BPV is effective as a vaccine, while BPV transformed cells are ineffective, suggest that viral capsid proteins, rather than early gene products, elicit the immune response. Other data in the scientific literature indicates that L1 protein extracted from bacteria was partially successful in eliciting an immune response despite the low titers of neutralizing antibodies. Accordingly, the BPV L1 that was expressed and assembled into virus-like particles in insect cells was studied for its ability to induce neutralizing antisera in rabbits. Two types of preparations were tested: whole cell extracts of L1 recombinant or wild type infected Sf-9 cells and partially purified particles isolated by differential centrifugation and ammonium sulfate precipitation. Following a primary inoculation, the rabbits received two biweekly booster inoculations.

Figure 3:
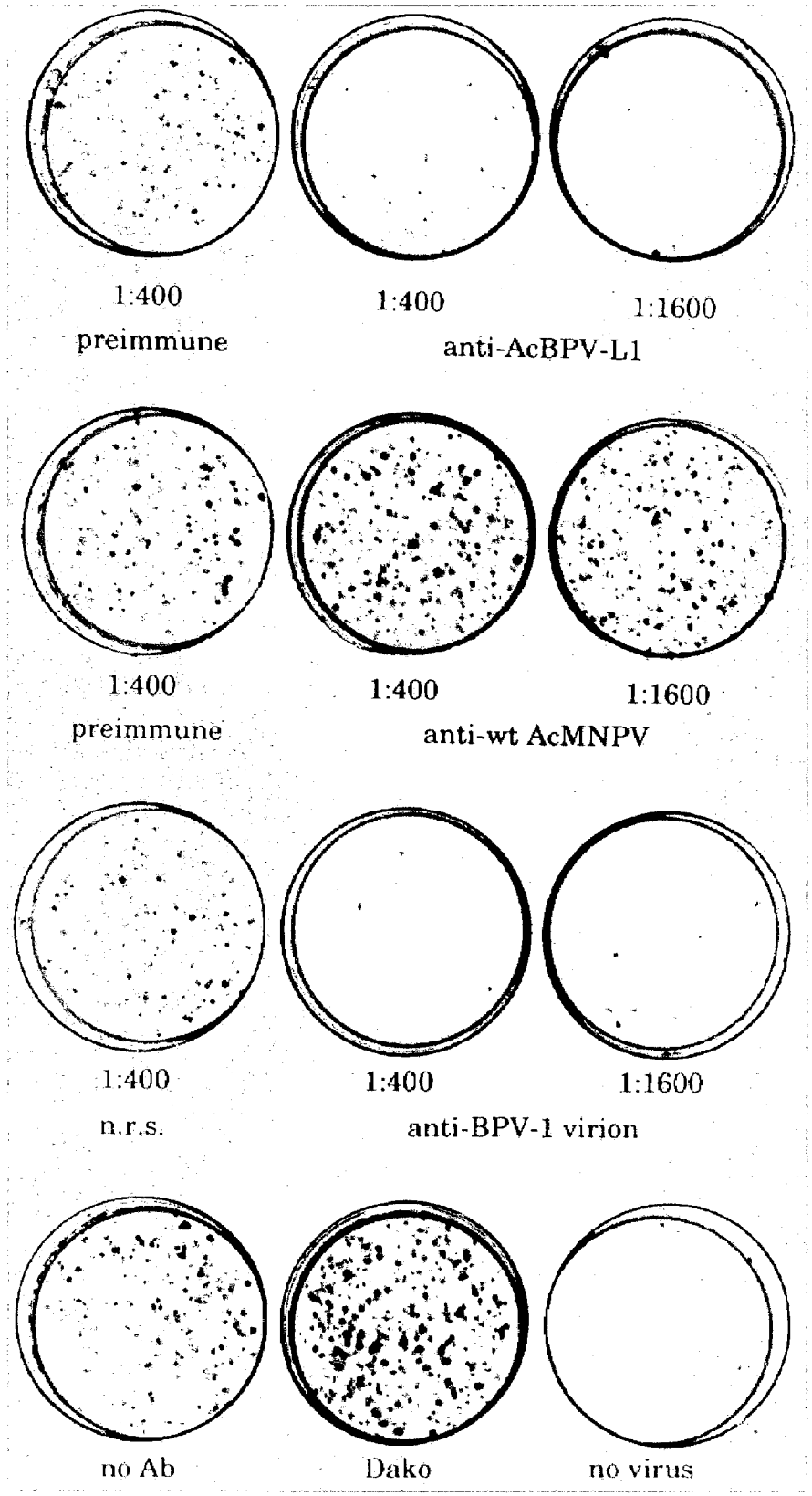
FIG. 3 shows the titers of neutralizing antisera induced in animals inoculated with recombinant BPV L1 as compared to antisera against intact and denatured BPV virions.

The rabbit sera were tested for the ability to inhibit BPV infection of mouse C127 cells, as measured by a reduction in the number of foci induced by a standard amount of BPV virus (a representative assay is shown in FIG. 3). The immune sera generated by inoculation with baculovirus derived L1 were able to reduce the infectivity of the BPV virus by 50% at a dilution of at least 1:11,000 (a titer of 11,000; Table 1), whereas the preimmune sera from the same rabbits did not inhibit focal transformation at a dilution of 1:20, the lowest dilution tested. Both the crude preparations and partially purified particles were effective in inducing high titer neutralizing antisera, with 290,000 being the highest titer measured. This was the same as the neutralizing titer of the positive control antiserum raised against infectious BPV virions. In comparison, the highest titer generated in a previous study using bacterially derived L1 was 36 (Pilancinski, W., et al., 1984). The serum from the rabbit inoculated with the extract from the wild type baculovirus infected cells was unable to inhibit infectivity at a dilution of 1:20, indicating that the neutralizing activity was L1 specific. Disruption of the partially purified L1 particles, by boiling in 1% SDS, abolished the ability of the preparation to induce neutralizing antibodies (Table 1). The demonstration that L1 can self-assemble into virion-like particles that elicit neutralizing antisera titers at least three orders of magnitude higher than previous in vitro-produced antigens suggests the recombinant L1 capsid proteins has the potential to induce effective long term protection against naturally transmitted papillomavirus. In view of these results, it appears that the L1 particles assembled in insect cells mimic infectious virus in the presentation of conformationally dependent immunodominant epitopes. These results also establish that L2 is not required for the generation of high titer neutralizing antibodies. The reported weak neutralizing immunogenicity of bacterially derived L1 may occur because it does not assume an appropriate conformation or has not assembled into virion like structures. Also, multiple electrophoretic variants of L1 have been detected in virions (Larsen, P., et al., 1987). Some of these modified species, which are probably absent in the bacterially derived L1, may facilitate the generation of neutralizing antibodies.

The ability of recombinant L1 (or L2) papillomavirus capsid proteins such as those disclosed herein to induce high titer neutralizing antiserum makes them suitable for use as vaccines for prophylaxis against communicable papillomatosis. Examples of populations at risk that could benefit from immunization are bovine herds, which are susceptible to papilloma warts; all humans for non-genital types of HPV infection; and sexually active humans for genital HPV types of infection.

Therapeutic vaccination can be useful for productive papillomavirus lesions, which usually express L1 (and L2) capsid proteins. Such lesions are most likely to occur in benign infections, such as warts or laryngeal papillomatosis. Laryngeal papillomatosis in newborns is usually contracted by the infant during passage through the birth canal where infectious papillomavirus is present in vaginal secretions. Therapeutic vaccination of infected pregnant women against the papillomavirus can induce neutralizing IgG antibody capable of passing through the placental barrier and into the circulation of the fetus to provide prophylactic passive immunity in the infant against this type of papillomavirus infection. Additional infant-protecting mechanisms are provided by maternal IgA which is secreted into the vaginal fluid and into breast milk. Jarrett (1991) demonstrates some therapeutic efficacy for L2 in treating BPV-induced warts. Malignant tumors typically do not express L1 or L2, and the efficacy of vaccination with recombinant L1 or L2 in conditions such as cervical cancer, is uncertain.

Protective immunity against both benign and malignant papillomavirus disease can be induced by administering an effective amount of recombinant L1 capsid protein to an individual at risk for papillomavirus infection. A vaccine comprising the capsid protein can be directly administered, either parenterally or locally, according to conventional immunization protocols. In an alternative embodiment, the conformational coding sequence of L1 can be cloned into a transfer vector, for example, a semliki forest virus vector (which produces a mild transient infection), the recombinant virus introduced into the cells or tissues of the recipient where the immunizing capsid protein is then expressed. Vaccinia virus can also be used as a vehicle for the gene.

Recombinant Conformed Capsid Proteins as Serological Screening Agents

Published serologic studies of human immune response to papillomavirus virion proteins have principally utilized bacterially derived L1 and L2 capsid proteins, and the results have not correlated well with other measures of HPV infection (Jenison, S., et al., 1990). BPV papillomavirus immunity studies described above indicate that papillomavirus virion proteins extracted from bacteria do not present the conformationally dependent epitopes that appear to be type-specific and recognized by most neutralizing antibodies. Compared with such assays that primarily recognize linear epitopes, a serological test using self-assembled L1 particles is likely to be a more accurate measure of the extent of anti-HPV virion immunity in the human population. The recombinant L1 capsid proteins disclosed herein, presenting conformational epitopes, can therefore be used as highly specific diagnostic reagents to detect immunity conferring neutralizing antibody to papilloma virus in binding assays of several types. The procedures can be carried out generally as either solid phase or solution assays that provide a means to detect antibodies in bodily fluids that specifically bind to the capsid protein in antigen-antibody pairs. Examples of procedures known to those skilled in the art for evaluating circulating antibodies are solution phase assays, such as double-antibody radioimmunoassays or enzyme immunoassays, or solid phase assays such as strip radioimmunoassay based on Western blotting or an enzyme-linked immunoabsorbent assay (ELISA) as disclosed in U.S. Pat. No. 4,520,113 to Gallo et al., or immunochromatographic assays as disclosed in U.S. Pat. No. 5,039,607 to Skold et al. A preferred ELISA method for the detection of antibodies is that disclosed in Harlow, E., and Lane, D. in *Antibodies: A Laboratory Manual* Cold Spring Harbor, N.Y., 1988, pp. 563–578.

The recombinant L1 or L1/L2 capsid proteins disclosed herein can also be used to measure cellular immunity to papillomavirus by means of in vivo or in vitro assays, for example, antigen-induced T-cell proliferative responses as described by Bradley, L., 1980, and particularly cellular responses to viral antigens, as described in U.S. Pat. No. 5,081,029 to Starling. Cellular immunity to papillomavirus can also be determined by the classical in vivo delayed hypersensitivity skin test as described by Stites, D., 1980; or in a preferred method, according to Höpfl, R., et al., 1991, by the intradermal injection of recombinant HPV L1 fusion proteins.

The capsid proteins of the invention can also be used as immunogens to raise polyclonal or monoclonal antibodies, according to methods well known in the art. These papillomavirus-specific antibodies, particularly in combination with labelled second antibodies, specific for a class or species of antibodies, can be used diagnostically according to various conventional assay procedures, such as immunohistochemistry, to detect the presence of capsid proteins in samples of body tissue or bodily fluids.

The genetic manipulations described below are disclosed in terms of their general application to the preparation of elements of the genetic regulatory unit of the invention. Occasionally, the procedure may not be applicable as described to each recombinant molecule included within the disclosed scope. The situations for which this occurs will be readily recognized by those skilled in the art. In all such cases, either the operations can be successfully performed by conventional modifications known to those skilled in the art, e.g. by choice of an appropriate alternative restriction enzyme, by changing to alternative conventional reagents, or by routine modification of reaction conditions. Alternatively, other procedures disclosed herein or otherwise conventional will be applicable to the preparation of the corresponding recombinant molecules of the invention. In all preparative methods, all starting materials are known or readily preparable from known starting materials. In the following examples, all temperatures are set forth in degrees Celsius; unless otherwise indicated, all parts and percentages are by weight.

Without further elaboration, it is believed that one skilled in the art can, using the preceding description, utilize the invention to its fullest extent. The following preferred embodiments are therefore to be construed as merely illustrative and not limiting the remainder of the disclosure in any way whatsoever.

EXAMPLE 1

Full length L1, or L1 and L2 open reading frames (ORF) were amplified by PCR using the cloned prototypes of BPV1 DNA (Chen, E., et al., 1982), GenBank Accession No. X02346 or HPV16 DNA (Seedorf, K., et al., 1985), GenBank Accession No. K02718; or wild type HPV16 DNA (SEQ ID NO: 3) as templates. Unique restriction sites were incorporated into the oligonucleotide primers (underlined).

BPV1 L1 primer sequence (SEQ ID NO: 5):

5'CCGCTGAATTCAATATGGCGTTGTG-GCAACAAGGCCAGAAGCTGTAT 3' (sense) and (SEQ ID NO: 6):

5' GCGGTGGTACCGTGCAGTTGACTTACCT-TCTGTTTTACATTTACAGA 3' (antisense);

HPV16 L1 primer sequence (SEQ ID NO: 7):

5'CCGCTAGATCTAATATGTCTCTTTGGCT-GCCTAGTGAGGCC 3' (sense); and (SEQ ID NO: 8):

5' GCGGTAGATCTACACTAATTCAACATA-CATACAATACTTACAGC 3' (antisense). L1 coding sequences begin at the 1st methionine codon (bold) for BPV1 and the 2nd methionine for HPV16. BPV1 L1 was cloned as a 5' EcoRI to 3' KpnI fragment and HPV16 L1 as a 5' BglII to 3' BglII fragment into the multiple cloning site downstream of the polyhedrin promoter of the AcMNPV based baculovirus transfer vector pEV mod (Wang, X., et al. 1991) and verified by sequencing through the AcMNPV/L1 junction. A quantity of 2 µg of CsCl purified recombinant plasmid was cotransfected with 1 µg wild type AcMNPV DNA (Invitrogen, San Diego, Calif.) into Sf 9 cells (ATCC) using lipofectin (Gibco/BRL, Gaithersburg, Md.) (Hartig, P., et al., 1991) and the recombinant baculoviruses plaque purified as described (Summers, M., et al., 1987).

EXAMPLE 2

Expression of L1 Proteins or L1/L2 Proteins in Insect Cells

Sf 9 cells were either mock infected (mock) or infected at a multiplicity of infection of 10 with either wt AcMNPV (wt) or AcBPV L1 (B L1), AcHPV16 L1 (16 L1), or AcHPV16 L1 (16 L1) and AcHPV16 L2 (16 L2) recombinant virus. After 72 hours, cells were lysed by boiling in Laemmli buffer and the lysates subjected to SDS PAGE in 10% gels. Proteins were either stained with 0.25% Coomassie blue (FIG. 1A) or immunoblotted and probed with BPV L1 mAb AU 1 (Nakai, Y., et al., 1986)(FIG. 1B) or HPV16L1 mAb CAMVIR 1 (McLean, C., et al., 1990)(FIG. 1C) and $^{125}I$ labeled Fab anti mouse IgG (Amersham). P designates polyhedrin protein.

EXAMPLE 3

Production of Antisera

Rabbits were immunized by subcutaneous injection either with whole cell Sf 9 lysates ($3 \times 10^7$ cells) prepared by one freeze/thaw cycle and 20× dounce homogenization (rabbit #1,2, and 8) or with 200 µg of L1 protein partially purified by differential centrifugation and 35% ammonium sulfate precipitation (#3,4,6, and 7), in complete Freund's adjuvant, and then boosted twice at two week intervals, using the same preparations in incomplete Freund's adjuvant.

EXAMPLE 4

Purification of Particles and Transmission Electron Microscopic (EMK) Analysis 500 ml of Sf 9 cells ($2 \times 10^6$/ml) were infected with AcBPV L1 (FIG. 2A) or AcHPV16 L1 (FIG. 2C) or AcHPV16 L1/L2 (16 L1/L2) recombinant baculoviruses. After 72 hr, the harvested cells were sonicated in PBS for 60 sec. After low speed clarification, the lysates were subjected to centrifugation at 110,000 g for 2.5 hr through a 40% (wt/vol) sucrose/PBS cushion (SW 28). The resuspended pellets were centrifuged to equilibrium at 141,000 g for 20 hr at room temperature in a 10 40% (wt/wt) CsCl/PBS gradient. Fractions were harvested from the bottom and analyzed by SDS PAGE. Immunoreactive fractions were dialyzed against PBS, concentrated by Centricon 30 (Millipore) ultrafiltration, and (for HPV16 L1) pelleted by centrifugation for 10 min at 30 psi in a A-100 rotor in an airfuge (Beckman). BPV1 virions (FIG. 2B) were purified from a bovine wart (generously provided by A. B. Jenson) as described (Cowsert, L., et al., 1987). Purified particles were adsorbed to carbon coated TEM grids, stained with 1% uranyl acetate and examined with a Philips electron microscope EM 400T at 36,000× magnification. Results are shown in FIG. 2. [The bar=50 nm].

EXAMPLE 5

BPV1 Neutralization Assay

Serial dilutions of sera obtained 3 wk after the second boost were incubated with approximately 500 focus forming units of BPV1 virus for 30 min, the virus absorbed to C127 cells for 1 hr and the cells cultured for 3 weeks (Dvoretzky, I., et al., 1980). The foci were stained with 0.5% methylene blue/0.25% carbol fuchsin/methanol. The results are shown in FIG. 3 and are discussed below. The antisera and dilutions used are indicated below the plates. Anti AcBPV L1 was obtained from rabbit #1 and anti wt AcMNPV from rabbit #8 (Table 1). The normal rabbit serum negative control is designated "nrs"; anti BPV1 virion was raised against native BPV virions in a previous study (Nakai, Y., et al., 1986); and Dako is the commercially available (Dako Corp., Santa Barbara, Calif.) rabbit antiserum raised against denatured BPV virions.

EXAMPLE 6

Serum Neutralizing Titer Against BPV1

Assays were carried out as in Example 5. Rabbits #1, 2, and 8 were inoculated with crude whole cell Sf 9 lysates, and rabbits # 3,4,6, and 7 with partially purified L1 protein (Table 1). Rabbits #6 and 7 were immunized with L1 protein preparations that had been denatured by boiling in 1% SDS. At least two bleeds, taken 3 6 weeks after the second boost, were tested for each rabbit and found to have the same titer. The titer of the preimmune sera from each of the rabbits was less than 20, the lowest dilution tested.

TABLE 1

| Antigen | rabbit | Serum neutralization titer against BPV1* |
|---|---|---|
| AcBPV-L1 | 1 | 11,000 |
| " | 2 | 97,000 |
| " | 3 | 290,000 |
| " | 4 | 97,000 |
| BPV1-virions | 5 | 290,000 |
| AcBPV-L1/SDS | 6 | <2 |
| " | 7 | <2 |
| Wt AcMNPV | 8 | <20 |

*reciprocal of dilution that caused 50% focus reduction
†provided by A. B. Jenson (Nakai, Y., et al., 1986).

The invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced within their scope.

BIBLIOGRAPHY

U.S. Pat. No. 5,081,029 to Starling et al.
U.S. Pat. No. 5,039,607 to Skold et al.
U.S. Pat. No. 4,520,113 to Gallo et al.
Baker, C. in *The Papovaviridae: Vol. 2. The Papillomaviruses* (N. Salzman et al., eds.) Plenum Press, New York, 1987. p. 321.
Baker, T., et al. Biophys. J. 60:1445 (1991).
Bradley, L. et al. in Selected Methods in Cellular Immunology. B. Mishell and S. Shiigi, eds. San Francisco: W.H. Freeman and Co., 1980. pp. 164–166.
Christensen, N., et al. Virology 64:5678 (1990).
Christensen, N., et al. Virology 181:572 (1991).
Crawford, L., et al. Virology 21:258 (1963).
Dvoretzky, I., et al. Virology 103:369 (1980).
Ghim, S., et al. Comparison of neutralization of BPV 1 infection of C127 cells and bovine fetal skin xenografts. Int. J. Cancer 49: 285 (1991).
Ghim, S., et al. HPV1-L1 protein expressed in cos cells displays conformational epitopes found on intact virions. Virology 190:548–552 (1992).
Hagensee, M., et al. Self-assembly of human papillomavirus type 1 capsids by expression of the L1 protein alone or by coexpression of the L1 and L2 capsid proteins. J. of Virology 67(1):315–322.
Höpfl, R., et al. Skin test for HPV type 16 proteins in cervical intraepithelial neoplasia. Lancet 337:373 (1991).
Jarrett, W., et al. Veterinary Record 126:449 (1990).
Jarrett, W., et al. Studies on vaccination against papillomaviruses: prophylactic and therapeutic vaccination with recombinant structural proteins. Virology 184:33 (1991).
Jenison, S., et al. J. Infectious Dis. 162:60 (1990).
Jenson, A., et al. Identification of linear epitopes BPV 1 L1 protein recognized by sera of infected or immunized animals. Pathobiology 59:396 (1991)
Jin, X., et al. J. Gen. Virology 70:1133 (1989).
Kajigaya, S., et al. Proc. Natl. Acad. Sci. USA 88:4646 (1991).
Kirnbauer, R., et al. Papillomavirus L1 major capsid protein self-assembles into virus-like particles that are highly immunogenic. Proc. Natl. Acad. Sci. USA 89:12180–12184 (1992).
Larsen, P., et al. J. Virology 61:3596 (1987).
Liddington, R., et al. Nature 354:278 (1991).
Lin, Y L., et al. Effective vaccination against papilloma development by immunization with L1 or L2 structural protein of cottontail rabbit papillovirus. Virology 187:612 (1992).
McLean, C., et al. Production and characterization of a monoclonal antibody to human papillomavirus type 16 using recombinant vaccinia virus. J. Clin. Pathol 43:488 (1990).
Nakai, Y. Intervirol. 25:30 (1986).
Olson, C., et al. Amer. J. Vet. Res. 21:233 (1960).
Pilacinski, W., et al. Biotechnology 2:356 (1984).
Saiki, R. K., et al. Science 239:487 (1987).
Seedorf, et al. Human papillomavirus type 16 DNA sequence. Virology 145:181–185 (1985)
Shiffman, M. J. National Cancer Inst. 84:394 (1992).
Stevens, C., et al. JAMA 257:2612 (1987).
Stites, D. Chapter 27 in *Basic and Clinical Immunology* 3d Ed. H. Fudenberg et al., eds. Los Altos: Lange Medical Publications, 1980.
Summers, M., et al. Texas Agricultural Experiment Station, College Station, Texas. A Manual of Methods for Baculovirus Vectors and Insect Cell Culture Procedures (1987). Bulletin No. 1555.
Zhou, J., et al. Expression of vaccinia recombinant HPV16 L1 and L2 ORF proteins in epithelial cells is sufficient for assembly of HPV virion like particles. J. Virology 185: 251 (1991).
zur Hausen, H. Science 254:1167 (1991).

What is claimed is:

1. A papillomavirus virus-like particle (VLP) comprising a HPV16 L1 having Aspartate at amino acid 202 instead of Histidine.

2. The papillomavirus VLP of claim 1 further comprising a HPV16 L2.

3. A papillomavirus virus-like particle (VLP) consisting of a HPV16 L1 having Aspartate at amino acid 202 instead of Histidine.

4. A method of making a papillomavirus virus-like particle (VLP) comprising a HPV16 L1 having Aspartate at amino acid 202 instead of Histidine comprising:
cloning a HPV16 L1 open reading frame (ORF) encoding a HPV16 L1 having Aspartate at amino acid 202 instead of Histidine into a vector wherein the ORF is under the control of a promoter of the vector,
transferring the vector into a host cell, wherein the HPV16 L1 is expressed as the expression product of the HPV16 L1 ORF, and
permitting self-assembly of said expression product into said papillomavirus VLP comprising said HPV16 L1 having Aspartate at amino acid 202 instead of Histidine.

5. The method of claim 4 further comprising isolating said papillomavirus VLP comprising a HPV16 L1 having Aspartate at amino acid 202 instead of Histidine.

6. A papillomavirus virus-like particle (VLP) comprising a HPV16 L1 having Aspartate at amino acid 202 instead of Histidine produced by the process of claim 4.

7. A papillomavirus virus-like particle (VLP) comprising a HPV16 L1 having Aspartate at amino acid 202 instead of Histidine produced by the process of claim 5.

8. The method of claim 4 wherein said vector further comprises a HPV16 L2 open reading frame (ORF) encoding a HPV16 L2, said HPV16 L2 is expressed as the expression product of the HPV16 L2 ORF, and said expression product is permitted to self-assemble into said papillomavirus VLP further comprising said HPV16 L2.

9. The method of claim 4 wherein said vector is an insect cell vector and said host cell is an insect host cell.

10. The method of claim 9 wherein said vector is a baculovirus vector and said insect host cell is a Sf-9 insect cell.

11. The method of claim 10 wherein said baculovirus vector is formed by cotransfecting a Sf-9 insect cell with recombinant baculovirus DNA and wild-type baculovirus DNA.

12. The method of claim 4 wherein said vector is a yeast cell vector and said host cell is a yeast host cell.

13. The method of claim 4 wherein said vector is a mammalian cell vector and said host cell is a mammalian host cell.

14. The method of claim 13 wherein said mammalian cell vector is a vaccinia vector.

15. A method of making a papillomavirus virus-like particle (VLP) consisting of a HPV16 L1 having Aspartate at amino acid 202 instead of Histidine comprising:
cloning a HPV16 L1 open reading frame (ORF) encoding a HPV16 L1 having Aspartate at amino acid 202 instead of Histidine into a vector wherein the ORF is under the control of a promoter of the vector,
transferring the vector into a host cell, wherein the HPV16 L1 is expressed as the expression product of the HPV16 L1 ORF, and
permitting self-assembly of said expression product into said papillomavirus VLP consisting of said HPV16 L1 having Aspartate at amino acid 202 instead of Histidine.

16. The method of claim 15 further comprising isolating said papillomavirus VLP consisting of a HPV16 L1 having Aspartate at amino acid 202 instead of Histidine.

17. A papillomavirus virus-like particle (VLP) consisting of a HPV16 L1 having Aspartate at amino acid 202 instead of Histidine produced by the process of claim 15.

18. A papillomavirus virus-like particle (VLP) consisting of a HPV16 L1 having Aspartate at amino acid 202 instead of Histidine produced by the process of claim 16.

* * * * *

SEQUENCE LISTING (1) GENERAL INFORMATION:

(iii) NUMBER OF SEQUENCES: 6

(2) INFORMATION FOR SEQ ID NO: 1:

(i) SEQUENCE CHARACTERISTICS:
       (A) LENGTH: 1517 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Human papillomavirus
       (B) STRAIN: HPV16

(ix) FEATURE:
       (A) NAME/KEY: CDS
       (B) LOCATION: 1..1517

(xi) SEQUENCE DESCRIPTION: SEQ ID NO: 1:

```
ATG TCT CTT TGG CTG CCT AGT GAG GCC ACT GTC TAC TTG CCT CCT GTC         48
Met Ser Leu Trp Leu Pro Ser Glu Ala Thr Val Tyr Leu Pro Pro Val
 1               5                  10                  15

CCA GTA TCT AAG GTT GTA AGC ACG GAT GAA TAT GTT GCA CGC ACA AAC         96
Pro Val Ser Lys Val Val Ser Thr Asp Glu Tyr Val Ala Arg Thr Asn
                20                  25                  30

ATA TAT TAT CAT GCA GGA ACA TCC AGA CTA CTT GCA GTT GGA CAT CCC        144
Ile Tyr Tyr His Ala Gly Thr Ser Arg Leu Leu Ala Val Gly His Pro
            35                  40                  45

TAT TTT CCT ATT AAA AAA CCT AAC AAT AAC AAA ATA TTA GTT CCT AAA        192
Tyr Phe Pro Ile Lys Lys Pro Asn Asn Asn Lys Ile Leu Val Pro Lys
        50                  55                  60

GTA TCA GGA TTA CAA TAC AGG GTA TTT AGA ATA CAT TTA CCT GAC CCC        240
Val Ser Gly Leu Gln Tyr Arg Val Phe Arg Ile His Leu Pro Asp Pro
 65              70                  75                  80

AAT AAG TTT GGT TTT CCT GAC ACC TCA TTT TAT AAT CCA GAT ACA CAG        288
Asn Lys Phe Gly Phe Pro Asp Thr Ser Phe Tyr Asn Pro Asp Thr Gln
                85                  90                  95

CGG CTG GTT TGG GCC TGT GTA GGT GTT GAG GTA GGT CGT GGT CAG CCA        336
Arg Leu Val Trp Ala Cys Val Gly Val Glu Val Gly Arg Gly Gln Pro
               100                 105                 110

TTA GGT GTG GGC ATT AGT GGC CAT CCT TTA TTA AAT AAA TTG GAT GAC        384
Leu Gly Val Gly Ile Ser Gly His Pro Leu Leu Asn Lys Leu Asp Asp
           115                 120                 125

ACA GAA AAT GCT AGT GCT TAT GCA GCA AAT GCA GGT GTG GAT AAT AGA        432
Thr Glu Asn Ala Ser Ala Tyr Ala Ala Asn Ala Gly Val Asp Asn Arg
       130                 135                 140

GAA TGT ATA TCT ATG GAT TAC AAA CAA ACA CAA TTG TGT TTA ATT GGT        480
Glu Cys Ile Ser Met Asp Tyr Lys Gln Thr Gln Leu Cys Leu Ile Gly
145                 150                 155                 160

TGC AAA CCA CCT ATA GGG GAA CAC TGG GGC AAA GGA TCC CCA TGT ACC        528
Cys Lys Pro Pro Ile Gly Glu His Trp Gly Lys Gly Ser Pro Cys Thr
               165                 170                 175

AAT GTT GCA GTA AAT CCA GGT GAT TGT CCA CCA TTA GAG TTA ATA AAC        576
Asn Val Ala Val Asn Pro Gly Asp Cys Pro Pro Leu Glu Leu Ile Asn
           180                 185                 190
```

```
                                              -continued

ACA GTT ATT CAG GAT GGT GAT ATG GTT CAT ACT GGC TTT GGT GCT ATG           624
Thr Val Ile Gln Asp Gly Asp Met Val His Thr Gly Phe Gly Ala Met
            195                 200                 205

GAC TTT ACT ACA TTA CAG GCT AAC AAA AGT GAA GTT CCA CTG GAT ATT           672
Asp Phe Thr Thr Leu Gln Ala Asn Lys Ser Glu Val Pro Leu Asp Ile
    210                 215                 220

TGT ACA TCT ATT TGC AAA TAT CCA GAT TAT ATT AAA ATG GTG TCA GAA           720
Cys Thr Ser Ile Cys Lys Tyr Pro Asp Tyr Ile Lys Met Val Ser Glu
225                 230                 235                 240

CCA TAT GGC GAC AGC TTA TTT TTT TAT TTA CGA AGG GAA CAA ATG TTT           768
Pro Tyr Gly Asp Ser Leu Phe Phe Tyr Leu Arg Arg Glu Gln Met Phe
                245                 250                 255

GTT AGA CAT TTA TTT AAT AGG GCT GGT ACT GTT GGT GAA AAT GTA CCA           816
Val Arg His Leu Phe Asn Arg Ala Gly Thr Val Gly Glu Asn Val Pro
            260                 265                 270

GAC GAT TTA TAC ATT AAA GGC TCT GGG TCT ACT GCA AAT TTA GCC AGT           864
Asp Asp Leu Tyr Ile Lys Gly Ser Gly Ser Thr Ala Asn Leu Ala Ser
    275                 280                 285

TCA AAT TAT TTT CCT ACA CCT AGT GGT TCT ATG GTT ACC TCT GAT GCC           912
Ser Asn Tyr Phe Pro Thr Pro Ser Gly Ser Met Val Thr Ser Asp Ala
290                 295                 300

CAA ATA TTC AAT AAA CCT TAT TGG TTA CAA CGA GCA CAG GGC CAC AAT           960
Gln Ile Phe Asn Lys Pro Tyr Trp Leu Gln Arg Ala Gln Gly His Asn
305                 310                 315                 320

AAT GGC ATT TGT TGG GGT AAC CAA CTA TTT GTT ACT GTT GTT GAT ACT          1008
Asn Gly Ile Cys Trp Gly Asn Gln Leu Phe Val Thr Val Val Asp Thr
                325                 330                 335

ACA CGC AGT ACA AAT ATG TCA TTA TGT GCT GCC ATA TCT ACT TCA GAA          1056
Thr Arg Ser Thr Asn Met Ser Leu Cys Ala Ala Ile Ser Thr Ser Glu
            340                 345                 350

ACT ACA TAT AAA AAT ACT AAC TTT AAG GAG TAC CTA CGA CAT GGG GAG          1104
Thr Thr Tyr Lys Asn Thr Asn Phe Lys Glu Tyr Leu Arg His Gly Glu
    355                 360                 365

GAA TAT GAT TTA CAG TTT ATT TTT CAA CTG TGC AAA ATA ACC TTA ACT          1152
Glu Tyr Asp Leu Gln Phe Ile Phe Gln Leu Cys Lys Ile Thr Leu Thr
370                 375                 380

GCA GAC GTT ATG ACA TAC ATA CAT TCT ATG AAT TCC ACT ATT TTG GAG          1200
Ala Asp Val Met Thr Tyr Ile His Ser Met Asn Ser Thr Ile Leu Glu
385                 390                 395                 400

GAC TGG AAT TTT GGT CTA CAA CCT CCC CCA GGA GGC ACA CTA GAA GAT          1248
Asp Trp Asn Phe Gly Leu Gln Pro Pro Pro Gly Gly Thr Leu Glu Asp
                405                 410                 415

ACT TAT AGG TTT GTA ACA TCC CAG GCA ATT GCT TGT CAA AAA CAT ACA          1296
Thr Tyr Arg Phe Val Thr Ser Gln Ala Ile Ala Cys Gln Lys His Thr
            420                 425                 430

CCT CCA GCA CCT AAA GAA GAT CCC CTT AAA AAA TAC ACT TTT TGG GAA          1344
Pro Pro Ala Pro Lys Glu Asp Pro Leu Lys Lys Tyr Thr Phe Trp Glu
    435                 440                 445

GTA AAT TTA AAG GAA AAG TTT TCT GCA GAC CTA GAT CAG TTT CCT TTA          1392
Val Asn Leu Lys Glu Lys Phe Ser Ala Asp Leu Asp Gln Phe Pro Leu
450                 455                 460

GGA CGC AAA TTT TTA CTA CAA GCA GGA TTG AAG GCC AAA CCA AAA TTT          1440
Gly Arg Lys Phe Leu Leu Gln Ala Gly Leu Lys Ala Lys Pro Lys Phe
465                 470                 475                 480

ACA TTA GGA AAA CGA AAA GCT ACA CCC ACC ACC TCA TCT ACC TCT ACA          1488
Thr Leu Gly Lys Arg Lys Ala Thr Pro Thr Thr Ser Ser Thr Ser Thr
                485                 490                 495

ACT GCT AAA CGC AAA AAA CGT AAG CTG TA                                   1517
Thr Ala Lys Arg Lys Lys Arg Lys Leu
```

```
              500             505

(2) INFORMATION FOR SEQ ID NO: 2:

(i) SEQUENCE CHARACTERISTICS:
        (A) LENGTH: 1517 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (ix) FEATURE:
        (A) NAME/KEY: CDS
        (B) LOCATION: 1..1517

(xi) SEQUENCE DESCRIPTION: SEQ ID NO: 2:

ATG TCT CTT TGG CTG CCT AGT GAG GCC ACT GTC TAC TTG CCT CCT GTC         48
Met Ser Leu Trp Leu Pro Ser Glu Ala Thr Val Tyr Leu Pro Pro Val
 1               5                  10                  15

CCA GTA TCT AAG GTT GTA AGC ACG GAT GAA TAT GTT GCA CGC ACA AAC         96
Pro Val Ser Lys Val Val Ser Thr Asp Glu Tyr Val Ala Arg Thr Asn
                20                  25                  30

ATA TAT TAT CAT GCA GGA ACA TCC AGA CTA CTT GCA GTT GGA CAT CCC        144
Ile Tyr Tyr His Ala Gly Thr Ser Arg Leu Leu Ala Val Gly His Pro
            35                  40                  45

TAT TTT CCT ATT AAA AAA CCT AAC AAT AAC AAA ATA TTA GTT CCT AAA        192
Tyr Phe Pro Ile Lys Lys Pro Asn Asn Asn Lys Ile Leu Val Pro Lys
    50                  55                  60

GTA TCA GGA TTA CAA TAC AGG GTA TTT AGA ATA CAT TTA CCT GAC CCC        240
Val Ser Gly Leu Gln Tyr Arg Val Phe Arg Ile His Leu Pro Asp Pro
65                  70                  75                  80

AAT AAG TTT GGT TTT CCT GAC ACC TCA TTT TAT AAT CCA GAT ACA CAG        288
Asn Lys Phe Gly Phe Pro Asp Thr Ser Phe Tyr Asn Pro Asp Thr Gln
                85                  90                  95

CGG CTG GTT TGG GCC TGT GTA GGT GTT GAG GTA GGT CGT GGT CAG CCA        336
Arg Leu Val Trp Ala Cys Val Gly Val Glu Val Gly Arg Gly Gln Pro
            100                 105                 110

TTA GGT GTG GGC ATT AGT GGC CAT CCT TTA TTA AAT AAA TTG GAT GAC        384
Leu Gly Val Gly Ile Ser Gly His Pro Leu Leu Asn Lys Leu Asp Asp
    115                 120                 125

ACA GAA AAT GCT AGT GCT TAT GCA GCA AAT GCA GGT GTG GAT AAT AGA        432
Thr Glu Asn Ala Ser Ala Tyr Ala Ala Asn Ala Gly Val Asp Asn Arg
130                 135                 140

GAA TGT ATA TCT ATG GAT TAC AAA CAA ACA CAA TTG TGT TTA ATT GGT        480
Glu Cys Ile Ser Met Asp Tyr Lys Gln Thr Gln Leu Cys Leu Ile Gly
145                 150                 155                 160

TGC AAA CCA CCT ATA GGG GAA CAC TGG GGC AAA GGA TCC CCA TGT ACC        528
Cys Lys Pro Pro Ile Gly Glu His Trp Gly Lys Gly Ser Pro Cys Thr
                165                 170                 175

AAT GTT GCA GTA AAT CCA GGT GAT TGT CCA CCA TTA GAG TTA ATA AAC        576
Asn Val Ala Val Asn Pro Gly Asp Cys Pro Pro Leu Glu Leu Ile Asn
            180                 185                 190

ACA GTT ATT CAG GAT GGT GAT ATG GTT GAT ACT GGC TTT GGT GCT ATG        624
Thr Val Ile Gln Asp Gly Asp Met Val Asp Thr Gly Phe Gly Ala Met
    195                 200                 205

GAC TTT ACT ACA TTA CAG GCT AAC AAA AGT GAA GTT CCA CTG GAT ATT        672
Asp Phe Thr Thr Leu Gln Ala Asn Lys Ser Glu Val Pro Leu Asp Ile
    210                 215                 220
```

-continued

```
TGT ACA TCT ATT TGC AAA TAT CCA GAT TAT ATT AAA ATG GTG TCA GAA        720
Cys Thr Ser Ile Cys Lys Tyr Pro Asp Tyr Ile Lys Met Val Ser Glu
225                 230                 235                 240

CCA TAT GGC GAC AGC TTA TTT TTT TAT TTA CGA AGG GAA CAA ATG TTT        768
Pro Tyr Gly Asp Ser Leu Phe Phe Tyr Leu Arg Arg Glu Gln Met Phe
                245                 250                 255

GTT AGA CAT TTA TTT AAT AGG GCT GGT ACT GTT GGT GAA AAT GTA CCA        816
Val Arg His Leu Phe Asn Arg Ala Gly Thr Val Gly Glu Asn Val Pro
            260                 265                 270

GAC GAT TTA TAC ATT AAA GGC TCT GGG TCT ACT GCA AAT TTA GCC AGT        864
Asp Asp Leu Tyr Ile Lys Gly Ser Gly Ser Thr Ala Asn Leu Ala Ser
        275                 280                 285

TCA AAT TAT TTT CCT ACA CCT AGT GGT TCT ATG GTT ACC TCT GAT GCC        912
Ser Asn Tyr Phe Pro Thr Pro Ser Gly Ser Met Val Thr Ser Asp Ala
    290                 295                 300

CAA ATA TTC AAT AAA CCT TAT TGG TTA CAA CGA GCA CAG GGC CAC AAT        960
Gln Ile Phe Asn Lys Pro Tyr Trp Leu Gln Arg Ala Gln Gly His Asn
305                 310                 315                 320

AAT GGC ATT TGT TGG GGT AAC CAA CTA TTT GTT ACT GTT GTT GAT ACT       1008
Asn Gly Ile Cys Trp Gly Asn Gln Leu Phe Val Thr Val Val Asp Thr
                325                 330                 335

ACA CGC AGT ACA AAT ATG TCA TTA TGT GCT GCC ATA TCT ACT TCA GAA       1056
Thr Arg Ser Thr Asn Met Ser Leu Cys Ala Ala Ile Ser Thr Ser Glu
            340                 345                 350

ACT ACA TAT AAA AAT ACT AAC TTT AAG GAG TAC CTA CGA CAT GGG GAG       1104
Thr Thr Tyr Lys Asn Thr Asn Phe Lys Glu Tyr Leu Arg His Gly Glu
        355                 360                 365

GAA TAT GAT TTA CAG TTT ATT TTT CAA CTG TGC AAA ATA ACC TTA ACT       1152
Glu Tyr Asp Leu Gln Phe Ile Phe Gln Leu Cys Lys Ile Thr Leu Thr
    370                 375                 380

GCA GAC GTT ATG ACA TAC ATA CAT TCT ATG AAT TCC ACT ATT TTG GAG       1200
Ala Asp Val Met Thr Tyr Ile His Ser Met Asn Ser Thr Ile Leu Glu
385                 390                 395                 400

GAC TGG AAT TTT GGT CTA CAA CCT CCC CCA GGA GGC ACA CTA GAA GAT       1248
Asp Trp Asn Phe Gly Leu Gln Pro Pro Pro Gly Gly Thr Leu Glu Asp
                405                 410                 415

ACT TAT AGG TTT GTA ACC AGG GCA ATT GCT TGT CAA AAA CAT ACA CCT       1296
Thr Tyr Arg Phe Val Thr Gln Ala Ile Ala Cys Gln Lys His Thr Pro
            420                 425                 430

CCA GCA CCT AAA GAA GAT GAT CCC CTT AAA AAA TAC ACT TTT TGG GAA       1344
Pro Ala Pro Lys Glu Asp Asp Pro Leu Lys Lys Tyr Thr Phe Trp Glu
        435                 440                 445

GTA AAT TTA AAG GAA AAG TTT TCT GCA GAC CTA GAT CAG TTT CCT TTA       1392
Val Asn Leu Lys Glu Lys Phe Ser Ala Asp Leu Asp Gln Phe Pro Leu
    450                 455                 460

GGA CGC AAA TTT TTA CTA CAA GCA GGA TTG AAG GCC AAA CCA AAA TTT       1440
Gly Arg Lys Phe Leu Leu Gln Ala Gly Leu Lys Ala Lys Pro Lys Phe
465                 470                 475                 480

ACA TTA GGA AAA CGA AAA GCT ACA CCC ACC ACC TCA TCT ACC TCT ACA       1488
Thr Leu Gly Lys Arg Lys Ala Thr Pro Thr Thr Ser Ser Thr Ser Thr
                485                 490                 495

ACT GCT AAA CGC AAA AAA CGT AAG CTG TA                                1517
Thr Ala Lys Arg Lys Lys Arg Lys Leu
            500                 505
```

(2) INFORMATION FOR SEQ ID NO: 3:

(i) SEQUENCE CHARACTERISTICS:
        (A) LENGTH: 47 base pairs
        (B) TYPE: nucleic acid
        (C) STRANDEDNESS: single (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bovine papillomavirus (vii) IMMEDIATE SOURCE:
        (B) CLONE: BPV1 N (xi) SEQUENCE DESCRIPTION: SEQ ID NO: 3:

CCGCTGAATT CAATATGGCG TTGTGGCAAC AAGGCCAGAA GCTGTAT                    47

(2) INFORMATION FOR SEQ ID NO: 4:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
        (B) CLONE: BPV1 Y (xi) SEQUENCE DESCRIPTION: SEQ ID NO: 4:

GCGGTGGTAC CGTGCAGTTG ACTTACCTTC TGTTTTACAT TTACAGA                   47

(2) INFORMATION FOR SEQ ID NO: 5:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: HPV16 N (xi) SEQUENCE DESCRIPTION: SEQ ID NO: 5:

CCGCTAGATC TAATATGTCT CTTTGGCTGC CTAGTGAGGC C                         41

(2) INFORMATION FOR SEQ ID NO: 6:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
        (B) CLONE: HPV16 Y (xi) SEQUENCE DESCRIPTION: SEQ ID NO: 6:

GCGGTAGATC TACACTAATT CAACATACAT ACAATACTTA CAGC    44